US012751963B2

(12) United States Patent
Ploss et al.

(10) Patent No.: US 12,751,963 B2
(45) Date of Patent: Oct. 6, 2026

(54) SMALL MOLECULE INHIBITORS OF VIRAL REPLICATION

(71) Applicant: The Trustees of Princeton University, Princeton, NJ (US)

(72) Inventors: Alexander Ploss, Princeton, NJ (US); Ila Nimgaonkar, Princeton, NJ (US); Hahn Kim, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 1084 days.

(21) Appl. No.: 17/607,280

(22) PCT Filed: May 12, 2020

(86) PCT No.: PCT/US2020/032449

§ 371 (c)(1),
(2) Date: Oct. 28, 2021

(87) PCT Pub. No.: WO2020/231979

PCT Pub. Date: Nov. 19, 2020

(65) Prior Publication Data

US 2022/0362276 A1 Nov. 17, 2022

Related U.S. Application Data

(60) Provisional application No. 62/911,040, filed on Oct. 4, 2019, provisional application No. 62/846,843, filed on May 13, 2019.

(51) Int. Cl.

| | |
|---|---|
| ***A61K 31/7076*** | (2006.01) |
| ***A61K 31/12*** | (2006.01) |
| ***A61K 31/192*** | (2006.01) |
| ***A61K 31/343*** | (2006.01) |
| ***A61K 31/352*** | (2006.01) |
| ***A61K 31/395*** | (2006.01) |
| ***A61K 31/40*** | (2006.01) |
| ***A61K 31/415*** | (2006.01) |
| ***A61K 31/4155*** | (2006.01) |
| ***A61K 31/4196*** | (2006.01) |
| ***A61K 31/42*** | (2006.01) |
| ***A61K 31/422*** | (2006.01) |
| ***A61K 31/426*** | (2006.01) |
| ***A61K 31/428*** | (2006.01) |
| ***A61K 31/4406*** | (2006.01) |
| ***A61K 31/4453*** | (2006.01) |
| ***A61K 31/505*** | (2006.01) |
| ***A61K 31/5375*** | (2006.01) |
| ***A61K 31/5377*** | (2006.01) |
| ***A61P 31/14*** | (2006.01) |

(52) U.S. Cl.

CPC .......... *A61K 31/7076* (2013.01); *A61K 31/12* (2013.01); *A61K 31/192* (2013.01); *A61K 31/343* (2013.01); *A61K 31/352* (2013.01); *A61K 31/395* (2013.01); *A61K 31/40* (2013.01); *A61K 31/415* (2013.01); *A61K 31/4155* (2013.01); *A61K 31/4196* (2013.01); *A61K 31/42* (2013.01); *A61K 31/422* (2013.01); *A61K 31/426* (2013.01); *A61K 31/428* (2013.01); *A61K 31/4406* (2013.01); *A61K 31/4453* (2013.01); *A61K 31/505* (2013.01); *A61K 31/5375* (2013.01); *A61K 31/5377* (2013.01); *A61P 31/14* (2018.01)

(58) Field of Classification Search

CPC .... A61K 31/192; A61K 31/12; A61K 31/343; A61K 31/352; A61K 31/351; A61P 31/14

See application file for complete search history.

(56) References Cited

U.S. PATENT DOCUMENTS 6,995,283 B2 * 2/2006 Chan .................... C07C 311/51 560/13
8,450,310 B2 5/2013 Drysdale et al.
(Continued)

FOREIGN PATENT DOCUMENTS

WO 2018/057773 A1 3/2018

OTHER PUBLICATIONS

Notification Concerning Transmittal of International Preliminary Report on Patentability for International Application No. PCT/US2020/032449, entitled: "Small Molecule Inhibitors of Viral Replication," mailed Nov. 25, 2021.
(Continued)

*Primary Examiner* — Pancham Bakshi
(74) *Attorney, Agent, or Firm* — Hamilton, Brook, Smith & Reynolds, P.C.

(57) ABSTRACT

Provided herein are methods involving a compound of the following structural formula: (I) or a pharmaceutically acceptable salt thereof, wherein values for the variables are as described herein. For example, methods for inhibiting replication of a virus, treating a viral infection, inhibiting heat shock protein 90 and treating a heat shock protein 90-mediated disease or condition using a compound of Structural Formula I are provided.

(I)

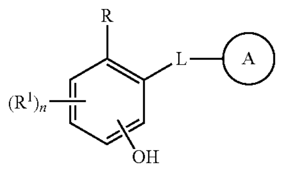

16 Claims, 42 Drawing Sheets

Specification includes a Sequence Listing.

(56) References Cited

U.S. PATENT DOCUMENTS

| | | | | |
|---|---|---|---|---|
| 9,408,826 B2 * | 8/2016 | Iadonato | A61P 31/12 | |
| 2018/0021269 A1 * | 1/2018 | Qin | A61P 31/22 | 514/675 |

OTHER PUBLICATIONS

Chan, J.H. et al., "Novel Benzophenones as Non-nucleoside Reverse Transcriptase Inhibitors of HIV-1," J Med Chem, vol. 47; 1175-1182 (2004).
Li, W. et al., "Plant Phenolic Compounds as Potential Lead Compounds in Functional Foods for Antiviral Drug Discovery," Bentham Science Publishers, vol. 21; 1847-1860 (2017).
Nakagawa, S. et al., "Hsp90 inhibitors suppress HCV replication in replicon cells and humanized liver mice," Biochemical and Biophysical Research Communication, vol. 353; 882-888 (2007).
Notification of Transmittal of the International Search Report and the Written Opinion of International Application No. PCT/US2020/032449, entitled: "Small Molecule Inhibitors of Viral Replication," mailed Sep. 1, 2020.
Benhamou Y, Tubiana R, Thibault V. Tenofovir disoproxil fumarate in patients with HIV and lamivudine-resistant hepatitis B virus. N Engl J Med 2003;348:177-178.
Debing Y, Gisa A, Dallmeier K, Pischke S, Bremer B, Manns M, et al. A mutation in the hepatitis E virus RNA polymerase promotes its replication and associates with ribavirin treatment failure in organ transplant recipients. Gastroenterology 2014;147:1008-1011.e1007; quiz e1015-1006.
Ding Q, Heller B, Capuccino JM, Song B, Nimgaonkar I, Hrebikova G, et al. Hepatitis E virus ORF3 is a functional ion channel required for release of infectious particles. Proc Natl Acad Sci U S A 2017;114:1147-1152.
Ding Q, Nimgaonkar I, Archer NF, Bram Y, Heller B, Schwartz RE, et al. Identification of the Intragenomic Promoter Controlling Hepatitis E Virus Subgenomic RNA Transcription. MBio 2018;9.
Fraga M, Gouttenoire J, Sahli R, Chtioui H, Marcu C, Pascual M, et al. Sofosbuvir add-on to ribavirin for chronic hepatitis E in a cirrhotic liver transplant recipient: a case report. BMC Gastroenterol 2019;19:76.
Gérolami R, Moal V, Colson P. Chronic hepatitis E with cirrhosis in a kidney-transplant recipient. N Engl J Med 2008;358:859-860.
Graff J, Torian U, Nguyen H, Emerson Su. A bicistronic subgenomic mRNA encodes both the ORF2 and ORF3 proteins of hepatitis E virus. J Virol 2006;80:5919-5926.
Haagsma EB, Riezebos-Brilman A, van den Berg AP, Porte RJ, Niesters HG. Treatment of chronic hepatitis E in liver transplant recipients with pegylated interferon alpha-2b. Liver Transpl 2010;16:474-477.
Jameel S, Zafrullah M, Ozdener MH, Panda SK. Expression in animal cells and characterization of the hepatitis E virus structural proteins. J Virol 1996;70:207-216.
Kamar N, Abravanel F, Selves J, Garrouste C, Esposito L, Lavayssière L, et al. Influence of immunosuppressive therapy on the natural history of genotype 3 hepatitis-E virus infection after organ transplantation. Transplantation 2010;89:353-360.
Kamar N, Lhomme S, Abravanel F, Marion O, Peron JM, Alric L, et al. Treatment of HEV Infection in Patients with a Solid-Organ Transplant and Chronic Hepatitis. Viruses 2016;8.
Kamar N, Mallet V, Izopet J. Ribavirin for chronic hepatitis E virus infection. N Engl J Med 2014;370:2447-2448.
Kamar N, Rostaing L, Abravanel F, Garrouste C, Lhomme S, Esposito L, et al. Ribavirin therapy inhibits viral replication on patients with chronic hepatitis e virus infection. Gastroenterology 2010;139:1612-1618.
Kamar N, Selves J, Mansuy JM, Quezzani L, Péron JM, Guitard J, et al. Hepatitis E virus and chronic hepatitis in organ-transplant recipients. N Engl J Med 2008;358:811-817.
Koonin EV, Gorbalenya AE, Purdy MA, Rozanov MN, Reyes GR, Bradley DW. Computer-assisted assignment of functional domains in the nonstructural polyprotein of hepatitis E virus: delineation of an additional group of positive-strand RNA plant and animal viruses. Proc Natl Acad Sci U S A 1992;89:8259-8263.
Lin TI, Lenz O, Fanning G, Verbinnen T, Delouvroy F, Scholliers A, et al. In vitro activity and preclinical profile of TMC435350, a potent hepatitis C virus protease inhibitor. Antimicrob Agents Chemother 2009;53:1377-1385.
Magden J, Takeda N, Li T, Auvinen P, Ahola T, Miyamura T, et al. Virus-specific mRNA capping enzyme encoded by hepatitis E virus. J Virol 2001;75:6249-6255.
Malcolm BA, Liu R, Lahser F, Agrawal S, Belanger B, Butkiewicz N, et al. SCH 503034, a mechanism-based inhibitor of hepatitis C virus NS3 protease, suppresses polyprotein maturation and enhances the antiviral activity of alpha interferon in replicon cells. Antimicrob Agents Chemother 2006;50:1013-1020.
Stedman C. Sofosbuvir, a NS5B polymerase inhibitor in the treatment of hepatitis C: a review of its clinical potential. Therap Adv Gastroenterol 2014;7:131-140.
Tam AW, Smith MM, Guerra ME, Huang CC, Bradley DW, Fry KE, et al. Hepatitis E virus (HEV): molecular cloning and sequencing of the full-length viral genome. Virology 1991;185:120-131.
Todt D, Moeller N, Praditya D, Kinast V, Friesland M, Engelmann M, et al. The natural compound silvestrol inhibits hepatitis E virus (HEV) replication in vitro and in vivo. Antiviral Res 2018;157:151-158.
Tsarev SA, Emerson SU, Reyes GR, Tsareva TS, Legters LJ, Malik IA, et al. Characterization of a prototype strain of hepatitis E virus. Proc Natl Acad Sci U S A 1992;89:559-563.
Van de Garde MD, Pas SD, van der Net G, de Man RA, Osterhaus AD, Haagmans BL, et al. Hepatitis E Virus (HEV) Genotype 3 Infection of Human Liver Chimeric Mice as a Model for Chronic HEV Infection. J Virol 2016;90:4394-4401.
Van Wezel EM, de Bruijne J, Damman K, Bijmolen M, van den Berg AP, Verschuuren EAM, et al. Sofosbuvir Add-on to Ribavirin Treatment for Chronic Hepatitis E Virus Infection in Solid Organ Transplant Recipients Does Not Result in Sustained Virological Response. Open Forum Infect Dis 2019;6.

* cited by examiner

| IC50 [uM] | Kc1p6/Gluc | Sar55/Gluc | SHEV-3/Gluc | TW6196E/Gluc |
|---|---|---|---|---|
| isocotoin | 4.134±1.213 | 4.952±1.232 | 6.130 ± [v wide] | 3.056±3.844 |
| ribavirin | 14.63±1.400 | 21.26±1.358 | 5.933±[v wide] | 24.45±1.658 |

FIG. 5G

```
                    SEQUENCE LISTING


<160> NUMBER OF SEQ ID NOS: 21

<210> SEQ ID NO 1
<211> LENGTH: 41
<212> TYPE: DNA
<213> ORGANISM: Artificial Sequence
<220> FEATURE:
<223> OTHER INFORMATION: PU-O-6099 primer

<400> SEQUENCE: 1

atacgtaata cgactcacta tagaatacaa gcttatgagc g                        41


<210> SEQ ID NO 2
<211> LENGTH: 38
<212> TYPE: DNA
<213> ORGANISM: Artificial Sequence
<220> FEATURE:
<223> OTHER INFORMATION: PU-O-6100 primer

<400> SEQUENCE: 2

agtcgtatta cgtatgtgta tgatacataa ggttatgt                           38
```

<210> SEQ ID NO 3
<211> LENGTH: 33
<212> TYPE: DNA
<213> ORGANISM: Artificial Sequence
<220> FEATURE:
<223> OTHER INFORMATION: PU-O-6101 primer

<400> SEQUENCE: 3
cagaactttg actcccatcg gtccaggatt ctc 33

<210> SEQ ID NO 4
<211> LENGTH: 30
<212> TYPE: DNA
<213> ORGANISM: Artificial Sequence
<220> FEATURE:
<223> OTHER INFORMATION: PU-O-6102 primer

<400> SEQUENCE: 4
gccggtggtg actaaatgga agacgccaaa 30

<210> SEQ ID NO 5
<211> LENGTH: 16
<212> TYPE: DNA
<213> ORGANISM: Artificial Sequence
<220> FEATURE:
<223> OTHER INFORMATION: PU-O-6103 primer

<400> SEQUENCE: 5
ttagtcacca ccggcc 16

<210> SEQ ID NO 6
<211> LENGTH: 23
<212> TYPE: DNA
<213> ORGANISM: Artificial Sequence
<220> FEATURE:
<223> OTHER INFORMATION: PU-O-2783 primer

<400> SEQUENCE: 6
atgggagtca aagttctgtt tgc 23

<210> SEQ ID NO 7
<211> LENGTH: 40
<212> TYPE: DNA
<213> ORGANISM: Artificial Sequence
<220> FEATURE:
<223> OTHER INFORMATION: PU-O-5963 primer

<400> SEQUENCE: 7
cgtaggacga agttacatga ggcagcacat tcagatgtcc 40

<210> SEQ ID NO 8
<211> LENGTH: 40
<212> TYPE: DNA
<213> ORGANISM: Artificial Sequence
<220> FEATURE:
<223> OTHER INFORMATION: PU-O-5964 primer

<400> SEQUENCE: 8
ggacatctga atgtgctgcc tcatgtaact tcgtcctacg 40

<210> SEQ ID NO 9
<211> LENGTH: 39
<212> TYPE: DNA
<213> ORGANISM: Artificial Sequence
<220> FEATURE:
<223> OTHER INFORMATION: PU-O-5965 primer

<400> SEQUENCE: 9
ctgtttgtga tttccttcga aggttgacga acgttgcgc 39

<210> SEQ ID NO 10
<211> LENGTH: 39
<212> TYPE: DNA
<213> ORGANISM: Artificial Sequence
<220> FEATURE:
<223> OTHER INFORMATION: PU-O-5966 primer

<400> SEQUENCE: 10
gcgcaacgtt cgtcaacctt cgaaggaaat cacaaacag 39

<210> SEQ ID NO 11
<211> LENGTH: 34
<212> TYPE: DNA
<213> ORGANISM: Artificial Sequence
<220> FEATURE:
<223> OTHER INFORMATION: PU-O-6433 primer

<400> SEQUENCE: 11
gaaagtcgcg ggtaaatcct gctgttttat gcgg 34

<210> SEQ ID NO 12
<211> LENGTH: 34
<212> TYPE: DNA
<213> ORGANISM: Artificial Sequence
<220> FEATURE:
<223> OTHER INFORMATION: PU-O-6434 primer

<400> SEQUENCE: 12
ccgcataaaa cagcaggatt tacccgcgac tttc 34

<210> SEQ ID NO 13
<211> LENGTH: 18
<212> TYPE: DNA
<213> ORGANISM: Artificial Sequence
<220> FEATURE:
<223> OTHER INFORMATION: Forward primer for HEV RNA quantification

<400> SEQUENCE: 13
ggtggtttct ggggtgac 18

<210> SEQ ID NO 14
<211> LENGTH: 18
<212> TYPE: DNA
<213> ORGANISM: Artificial Sequence
<220> FEATURE:
<223> OTHER INFORMATION: Reverse primer for HEV RNA quantification

<400> SEQUENCE: 14
aggggttggt tggatgaa 18

<210> SEQ ID NO 15
<211> LENGTH: 18
<212> TYPE: DNA
<213> ORGANISM: Artificial Sequence
<220> FEATURE:
<223> OTHER INFORMATION: FAM-BHQ probe primer

<400> SEQUENCE: 15
tgattctcag cccttcgc 18

<210> SEQ ID NO 16

<211> LENGTH: 23
<212> TYPE: DNA
<213> ORGANISM: Artificial Sequence
<220> FEATURE:
<223> OTHER INFORMATION: HSP90AA1-F primer

<400> SEQUENCE: 16
cataacgatg atgagcagta cgc 23

<210> SEQ ID NO 17
<211> LENGTH: 21
<212> TYPE: DNA
<213> ORGANISM: Artificial Sequence
<220> FEATURE:
<223> OTHER INFORMATION: HSP90AA1-R primer

<400> SEQUENCE: 17
gacccatagg ttcacctgtg t 21

<210> SEQ ID NO 18
<211> LENGTH: 22
<212> TYPE: DNA
<213> ORGANISM: Artificial Sequence
<220> FEATURE:
<223> OTHER INFORMATION: HSP90AB1-F primer

<400> SEQUENCE: 18
agaaattgcc caactcatgt cc 22

<210> SEQ ID NO 19
<211> LENGTH: 23
<212> TYPE: DNA
<213> ORGANISM: Artificial Sequence
<220> FEATURE:
<223> OTHER INFORMATION: HSP90AB1-R primer

<400> SEQUENCE: 19
atcaactccc gaaggaaaat ctc 23

<210> SEQ ID NO 20
<211> LENGTH: 19
<212> TYPE: DNA
<213> ORGANISM: Artificial Sequence
<220> FEATURE:
<223> OTHER INFORMATION: GAPDH-F primer

<400> SEQUENCE: 20
gaaggtgaag gtcggagtc 19

<210> SEQ ID NO 21
<211> LENGTH: 20
<212> TYPE: DNA
<213> ORGANISM: Artificial Sequence
<220> FEATURE:
<223> OTHER INFORMATION: GAPDH-R primer

<400> SEQUENCE: 21
gaagatggtg atgggatttc 20

SMALL MOLECULE INHIBITORS OF VIRAL REPLICATION

RELATED APPLICATIONS

This application is the U.S. National Stage of International Application No. PCT/US2020/032449, filed May 12, 2020, published in English, which claims the benefit of U.S. Provisional Application No. 62/911,040, filed on Oct. 4, 2019, and U.S. Provisional Application No. 62/846,843, filed on May 13, 2019. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 53911022002_SEQUENCELISTINGFINAL.txt; created May 4, 2020, 4.1 KB in size.

BACKGROUND

There is no approved direct-acting antiviral treatment for hepatitis E virus (HEV), which causes approximately 14 million symptomatic infections and approximately 300,000 deaths per year globally. Following infection, immunocompromised persons and pregnant women experience particularly severe clinical manifestations including liver cirrhosis and acute liver failure, respectively. Ribavirin monotherapy can be used to treat chronic hepatitis E in solid-organ transplant recipients; however, ribavirin is not safe for pregnant women and, furthermore, ribavirin-resistant HEV strains are emerging.

Accordingly, there is a need for therapies for HEV and other viral infections.

SUMMARY

Provided herein is a method of inhibiting replication of a virus (e.g., a hepatitis E virus (HEV), an HEV in a cell), comprising contacting a cell infected with the virus (e.g., an HEV, one or more HEV particles) with a compound represented by the following structural formula:

(I)

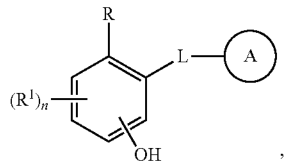

, or a pharmaceutically acceptable salt thereof, wherein:

Ring A is aryl (e.g., phenyl) or heteroaryl (e.g., oxazolyl, pyridinyl, benzothiazolyl, thiazolyl, pyrazolyl or benzofuranyl), and is optionally substituted with one or more substituents independently selected from halo, hydroxy, alkyl, haloalkyl, alkoxy, haloalkoxy, $—(CH_2)_{0-2}$-aryl, $—(CH_2)_{0-2}$-heteroaryl, $—(CH_2)_{0-2}$-cycloalkyl, or $—(CH_2)_{0-2}$-heterocyclyl, carboxy or $—O(CH_2)_mO—$;

m is 1, 2, 3, 4 or 5 (e.g., 1, 2 or 3);

L is $—C(O)(CH_2)_p—$, $—C(O)(CH_2)_p—O—$ or heteroarylene (e.g., oxazolylene, pyrimidinylene or pyrazolylene), wherein p is 0, 1 or 2 (e.g., 0 or 1), and R is hydrogen, halo, hydroxy, alkyl, haloalkyl, alkoxy, haloalkoxy, alkenoxy, alkynoxy, $—(CH_2)_{0-2}$-aryl, or $—(CH_2)_{0-2}$-heteroaryl; or L is $—C(O)(CH_2)_p—$, wherein p is 1 or 2, and R and a methylene carbon of $—C(O)(CH_2)_p—$, together with their intervening carbon atoms, form a fused ring (e.g., containing five, six, seven or eight members independently selected from carbon, oxygen, nitrogen and sulfur);

$R^1$ is halo, hydroxy, alkyl, haloalkyl, alkoxy, haloalkoxy, alkenoxy, alkynoxy, $—(CH_2)_{0-2}$-aryl, or $—(CH_2)_{0-2}$-heteroaryl; and n is 0, 1, 2 or 3, wherein the aryl and heteroaryl of R and $R^1$, and the heteroarylene of L are each optionally and independently substituted with one or more substituents selected from halo, alkyl, haloalkyl, amino, alkylamino, dialkylamino or carboxamido.

Also provided herein is a method of inhibiting replication of a virus (e.g., an HEV) comprising contacting a cell infected with the virus with a compound of Appendix 1, 1', 2, 2', 3 or 4, or a pharmaceutically acceptable salt thereof, or isocotoin, or a pharmaceutically acceptable salt thereof.

Also provided herein is a method of treating a viral infection (e.g., an HEV infection) in a subject in need thereof, comprising administering to the subject an effective amount of a compound represented by Structural Formula I, or a pharmaceutically acceptable salt thereof, wherein values for the variables in Structural Formula I are as described herein.

Also provided herein is a method of treating a viral infection (e.g., an HEV infection) in a subject in need thereof, comprising administering to the subject an effective amount of a compound of Appendix 1, 1', 2, 2', 3 or 4, or a pharmaceutically acceptable salt thereof, or isocotoin, or a pharmaceutically acceptable salt thereof.

Also provided herein is a method of inhibiting heat shock protein 90 in a cell, comprising contacting the cell with a compound represented by Structural Formula I, or a pharmaceutically acceptable salt thereof, wherein values for the variables in Structural Formula I are as described herein.

Also provided herein is a method of inhibiting heat shock protein 90 in a cell, comprising contacting the cell with a compound of Appendix 1, 1', 2, 2', 3 or 4, or a pharmaceutically acceptable salt thereof, or isocotoin, or a pharmaceutically acceptable salt thereof.

Also provided herein is a method of treating a heat shock protein 90-mediated disease or condition (e.g., an HEV infection) in a subject in need thereof, comprising administering to the subject an effective amount of a compound represented by Structural Formula I, or a pharmaceutically acceptable salt thereof, wherein values for the variable in Structural Formula I are as described herein.

Also provided herein is a method of treating a heat shock protein 90-mediated disease or condition (e.g., an HEV infection) in a subject in need thereof, comprising administering to the subject an effective amount of a compound of Appendix 1, 1', 2, 2', 3 or 4, or a pharmaceutically acceptable salt thereof, or isocotoin, or a pharmaceutically acceptable salt thereof.

Also provided herein is a compound for use in inhibiting replication of a virus (e.g., an HEV), treating a viral infection (e.g., an HEV infection), inhibiting heat shock protein 90 or treating a heat shock protein 90-mediated disease or condition, wherein the compound is described herein (e.g., a compound of Structural Formula I; a compound of Appendix 1, 1', 2, 2', 3 or 4; isocotoin, or a pharmaceutically acceptable salt of any of the foregoing). Also provided herein is use of a compound described herein (e.g., a compound of Structural Formula I; a compound of Appendix 1, 1', 2, 2', 3 or 4; isocotoin, or a pharmaceutically acceptable salt of any of the foregoing) for the manufacture of a medicament for inhibiting replication of a virus (e.g., an HEV), treating a viral infection (e.g., an HEV infection), inhibiting heat shock protein 90 or treating a heat shock protein 90-mediated disease or condition.

Compounds of Structural Formula I are effective inhibitors of viral replication in vitro. In functional assays of HEV using hepatoma cells, certain representative compounds of Structural Formula I exhibited higher potency than ribavirin, low host cytotoxicity, and pan-genotypic efficacy, suggesting that the compounds of Structural Formula I may be promising candidates for novel, direct-acting therapies against viruses, such as HEV.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 2A: The p6/BSR-2A-ZsGreen replicon genome was derived from KernowC1p6, with ORFs 2 and 3 replaced by a blasticidin resistance-conferring gene (BSR) and a ZsGreen fluorescence reporter (ZsG), with a 2A self-cleaving peptide in between. FIG. 2B: GFP channel image of Huh7 cells transfected with p6/BSR-2A-ZsGreen and selected under blasticidin pressure to generate a population highly expressing ZsGreen. FIG. 2C: Flow cytometric analysis of p6/BSR-2A-ZsGreen-transfected Huh7 cells (right; 90.2% ZsGreen positive) versus naïve Huh7 cells (left; 3.58% ZsGreen positive).

FIG. 3A: Huh7 p6/BSR-2A-ZsGreen cells were seeded into 384-well plates containing one distinct compound/well from the Princeton University Small Molecule Screening Facility. 60,536 compounds in total were screened (188 plates). Cells were seeded at a density of 8000 cells/well, with each compound diluted to a concentration of 50 μM. Four columns of each plate were used for positive (untreated Huh7 p6/BSR-2A-ZsGreen cells) and negative (naïve Huh7 cells) controls. FIG. 3B: A GFP channel image (top) and brightfield image (bottom) were taken of each well on day 4 using the Perkin Elmer Operetta High-Content Imaging System. Fluorescence in the GFP channel images were quantified using a custom Python script, and decreased fluorescence was used as a metric to select hits with putative antiviral activity. Approximately 800 hits were manually screened for cytotoxicity using the corresponding brightfield images. 37 hits were ultimately chosen for further characterization. FIG. 3C: The 37 selected hits were tested in the same 384-well format against Huh7 p6/BSR-2A-ZsGreen cells at doses from 0.78-100 μM. Fluorescence in the wells was quantified and used to generate dose titration curves for each compound. Seven compounds had IC50 values lower than that of ribavirin, for example the compound abbreviated G11. FIG. 3D: The seven compounds were tested at doses ranging from 1.5625-100 μM against the p6/Gluc replicon, in order to provide a more direct readout of activity. Two compounds, isocotoin and gitoxin, showed dose-dependent inhibition of p6/Gluc. FIG. 3E: In an ATP live-cell viability assay, gitoxin demonstrated high cytotoxicity. RLU=relative light units. Error bars indicate 1 standard deviation (SD) from mean.

FIG. 4A: Structure of isocotoin. FIG. 4B: Schematic of KernowC1p6 replicon and p6/Gluc replicon. FIG. 4C: Isocotoin inhibits p6/Gluc replication more efficiently than ribavirin in vitro. FIG. 4D: Isocotoin inhibits replication of full-length KernowC1-p6 in vitro. FIG. 4E: Schematic of T7-tagBFP-Gluc. FIG. 4F: Isocotoin and ribavirin do not inhibit translation of T7-tagBFP-Gluc. FIG. 4G: Isocotoin is non-cytotoxic to Huh7 cells up to 12.5 M. RLU=relative light units. Error bars indicate 1 SD from mean.

FIGS. 5A-5G. Isocotoin inhibits replication of genetically diverse strains of HEV. FIG. 5A: Of the 8 HEV genotypes categorized in Orthohepevirus A, genotypes 1-4 are human-tropic. FIG. 5B: Gluc-expressing replicon genomes were generated for HEV strains derived from genotypes 1, 3, and 4. Three of the original strains were isolated from human patients, and one was isolated from a swine host. FIGS. 5C-5F: Isocotoin inhibits replication of p6/Gluc (GT3), Sar55/Gluc (GT1), SHEV-3/Gluc(GT3), and TW6196E/Gluc(GT4) replicon strains. FIG. 5G: Corresponding $IC_{50}$ values for dose titration data with standard error indicated. RLU=relative light units. Error bars indicate 1 SD from mean.

FIGS. 6A-6B: Isocotoin inhibits replication of Gluc-expressing HEV, yellow fever virus 17D (YFV), and hepatitis C virus (HCV) genomes to a greater extent than ribavirin. RLU values are normalized to untreated conditions. FIG. 6C: Schematic of pACNR-FLYF-17D-Gluc-BSD-Ires construct, which is derived from pACNR/FLYF-17D (GenBank ID: AY640589). FIG. 6D: 2'C-Methyladenosine (2'CMA), a potent and specific inhibitor of HCV replication, was tested against the Glue-expressing HEV-, YFV-, and HCV-derived viruses. RLU=relative light units. All data points are mean of triplicate wells (n=3). Error bars indicate 1 SD from mean.

FIG. 7A: Schematic of suboptimal dosing experiment. FIG. 7B: p6/BSR-2A-ZsGreen]-expressing Huh7 cells serially passaged in medium containing 30 M isocotoin showed a decrease in ZsGreen expression up to passage 5, and a subsequent increase in ZsGreen expression between passages 5-10. FIG. 7C: At passage 10, the F470S point mutation was found in 2/10 colonies sequenced. An additional similar mutation F473S was found in 1/10 colonies. FIG. 7D: Replication kinetics for p6/Gluc[F470S], p6/Gluc[G1634R], p6/Gluc[Y1320H], and p6/Gluc-WT over 4 days. FIG. 7E: Schematics of viral genome and Gluc-expressing replicons. The p6/Gluc [F470S], p6/Gluc[Y1320H], and p6/Gluc[G1634R] strains are derived from p6/Gluc and contain point mutations in the PCP, RdRp, and RdRp and regions respectively. FIGS. 7F-7G: Dose titration of isocotoin and ribavirin against mutant strains. BSR=blasticidin resistance gene; BSD=blasticidin; ZsG=ZsGreen; RLU=relative light units. Error bars indicate 1 SD from mean.

FIG. 8A: First round of SAR analysis. Structurally related compounds to isocotoin show greater inhibition of p6/Gluc at the 25 M dose. FIG. 8B: Second round of SAR analysis. Structurally related compounds to isocotoin show greater inhibition of p6/Gluc at the 1.5625 μM dose. RLU=relative light units. Error bars indicate 1 SD from mean.

FIG. 10A: Second round of SAR analysis. A subset of structurally related compounds to isocotoin showed greater inhibition of p6/Gluc. One subset of compounds showed high potency but was associated with high cytotoxicity. Another subset was less effective than isocotoin and ribavirin. Data is compiled from multiple batches of experiments hence variation in control curves from isocotoin and ribavirin. FIG. 10B: Titration of highly effective compounds at lower doses. RLU=relative light units. Error bars indicate 1 SD from mean.

FIG. 11A: Schematic of cellular thermal shift assay (CETSA) workflow. FIG. 11B: Heatmaps showing CETSA data for HSP90AA1 and HSPP90AB1. Numbers in heatmaps indicate foldchange in soluble protein at indicated isocotoin concentration and heating temperature. FIG. 11C: AUY-922, STA-9090, VER-50589, and 17-AAG are potent inhibitors of HEV [p6/Gluc strain] replication. FIG. 11D: Treatment with HSP90-specific siRNA results in a 69% reduction in HSP90 protein levels at 72 h post-transfection. HSP90 bands are normalized to β-actin band intensity for each lane. FIG. 11E: Treatment with HSP90-specific siRNA results in 54% reduction in HSP90a and 74% reduction in HSP900 mRNA levels. Data are combined from two repeat experiments and normalized to cellular GAPDH levels. FIG. 11F: Treatment with HSP90-specific siRNA results in reduced viral replication of HEVΔORF2/3[Gluc] as measured via *Gaussia luciferase* secretion 3 days post transfection. *Gaussia luciferase* levels were decreased 51% as compared to mock-transfected cells and 36% as compared to cells treated with negative control, seed sequence-matched siRNA. Data are combined from two repeat experiments and normalized to viral replication levels in cells treated with transfection reagent. FIG. 11G: Hypothesized general mechanism for isocotoin-mediated inhibition of pORF1 folding.

FIG. 12A: Approximately 75 commercially available compounds with structural similarities to isocotoin were screened in successive rounds to correlate functional groups with biological activity, and to identify compounds with higher potency than isocotoin. Dose titration assays were conducted in 96-well format for all 75 compounds against the p6/Gluc replicon. Six selected compounds are shown above, with columns indicating luciferase activity at the approximate 15 μM dose. The most potent analogs identified were AUY-922 and VER-50589, which are known HSP90 inhibitors. FIG. 12B: ATP-based live cell assay shows that known HSP90 inhibitors 17-AAG, VER-50589, AUY-922, and STA-9090 are inhibitors of cell growth.

FIG. 14A: Western blot indicating expression of HSP90α/β 72 h post-treatment with transfection reagents only (Mock), seed sequence-matched negative control siRNA ((−)siRNA), or HSP90 siRNA. FIG. 14B: 8-bit image of Western blot used for band quantification. FIG. 14C: Profile plot showing density peaks and raw quantification values for bands in FIG. 14B. FIG. 14D: Treatment with HSP90-specific siRNA results in reduced viral replication of HEVΔORF2/3[Gluc] as measured via *Gaussia luciferase* secretion on days 1-4 post-transfection. RLU=relative light units. n=12 wells per data point. Error bars indicate 1 SD from mean.

FIG. 15A: Human albumin levels were measured in serum to indicate engraftment levels. FIG. 15B: Eight mice were injected with stool filtrate from HEV-infected rhesus macaques to establish chronic infection. Weight of the mice post-infection as percentage of baseline. FIG. 15C: Viral titers in stool pellets collected from the mice. L.O.D.=limit of detection. FIG. 15D: Six mice were treated with isocotoin for seven days at a 50 mg/kg dose injected daily intraperitoneally. FIG. 15E: Analysis of viral RNA extracted from stool pellets before (blue) and after (red) treatment. RT-qPCR was performed in duplicate.

DETAILED DESCRIPTION

Figure 1:
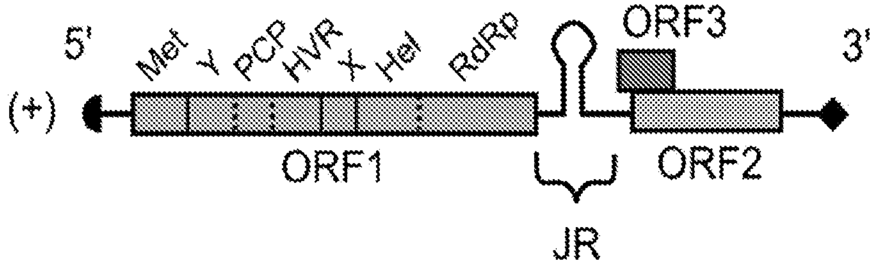
FIG. 1. Genomic organization of HEV, a single-stranded positive sense RNA virus.

A description of example embodiments follows.

Definitions

Compounds described herein include those described generally, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the relevant contents of which are incorporated herein by reference.

Unless specified otherwise within this specification, the nomenclature used in this specification generally follows the examples and rules stated in Nomenclature of Organic Chemistry, Sections A, B, C, D, E, F, and H, Pergamon Press, Oxford, 1979, which is incorporated by reference herein for its chemical structure names and rules on naming chemical structures. Optionally, a name of a compound may be generated using a chemical naming program (e.g., CHEMDRAW®, version 17.0.0.206, PerkinElmer Informatics, Inc.).

"Alkyl" refers to a saturated, aliphatic, branched or straight-chain, monovalent, hydrocarbon radical having from one to 25 (e.g., from one to 20, from one to 15, from one to 10, from one to five) carbon atoms. When there is an indication of the number of carbon atoms in an alkyl group, the alkyl group has the indicated number of carbon atoms. Thus, "$(C_1-C_5)$alkyl" means a radical having from 1-5 carbon atoms in a linear or branched arrangement. Examples of alkyl groups include methyl, ethyl, n-propyl, isopropyl, n-butyl, isobutyl, sec-butyl, t-butyl, n-pentyl, isopentyl, neopentyl, 2-methylpentyl, n-hexyl, and the like.

"Alkoxy" refers to an alkyl radical attached through an oxygen linking atom, wherein alkyl is as described herein. Examples of alkoxy include, but are not limited to, methoxy, ethoxy, propoxy, isopropoxy, and the like.

"Alkenyl" refers to an aliphatic, branched or straight-chain, monovalent, hydrocarbon radical having at least one carbon-carbon double bond and from two to 25 (e.g., from two to 20, from two to 15, from two to 10, from two to five) carbon atoms. When there is an indication of the number of carbon atoms in an alkenyl group, the alkenyl group has the indicated number of carbon atoms. Thus, "($C_2$-$C_5$)alkenyl" means a radical having at least one carbon-carbon double bond and from two to five carbon atoms in a linear or branched arrangement. Examples of alkenyl groups include ethenyl, 2-propenyl, 1-propenyl, 2-methyl-1-propenyl, 1-butenyl, 2-butenyl, 1-pentenyl, 2-pentenyl, 3-pentenyl, allyl, 1, 3-butadienyl, 1, 3-dipentenyl, 1,4-dipentenyl, 1-hexenyl, 1,3-hexenyl, 1,4-hexenyl, 1,3,5-trihexenyl, 2,4-dihexenyl, and the like.

"Alkenoxy" refers to an alkenyl radical attached through an oxygen linking atom, wherein alkenyl is as described herein. Examples of alkenoxy include, but are not limited to, ethenoxy, propenoxy, and the like.

"Alkynyl" refers to an aliphatic, branched or straight-chain, monovalent, hydrocarbon radical having at least one carbon-carbon triple bond and from two to 25 (e.g., from two to 20, from two to 15, from two to 10, from two to five) carbon atoms. When there is an indication of the number of carbon atoms in an alkynyl group, the alkynyl group has the indicated number of carbon atoms. Thus, "($C_2$-$C_5$)alkynyl" means a radical having at least one carbon-carbon triple bond and from two to five carbon atoms in a linear or branched arrangement. Examples of alkynyl groups include ethynyl, 1-propynyl, 2-propynyl, 1-butynyl, 2-butynyl, 2-methyl-1-butynyl, 1-pentynyl, 2-pentynyl, 3-pentynyl, 3-methyl-1-pentynyl, 2-methyl-1-pentynyl, 1-hexynyl, 2-hexynyl, 3-hexynyl, and the like.

"Alkynoxy" refers to an alkynyl radical attached through an oxygen linking atom, wherein alkynyl is as described herein. Examples of alkynoxy include, but are not limited to, ethynoxy, propynoxy, and the like.

"Amino" means —$NH_2$.

"Alkylamino" refers to —N(H)(alkyl), wherein alkyl is as described herein. Alkylamino includes, but is not limited to, methylamino and ethylamino.

"Aryl" refers to a monocyclic or polycyclic (e.g., bicyclic, tricyclic), carbocyclic, aromatic ring system having from six to 25 (e.g., from six to 20, from six to 15, from six to 10) ring atoms. When there is an indication of the number of ring atoms in an aryl group, the aryl group has the indicated number of ring atoms. Thus, "($C_6$-$C_{15}$)aryl" means an aromatic ring system having from six to 15 ring atoms. Examples of aryl include phenyl and naphthyl.

"Carboxy" refers to —COOH.

"Carboxamido" refers to —C(O)NR°R°°, wherein R° and R°° are each independently hydrogen or alkyl, wherein alkyl is as described herein. When R° and R°° are both alkyl, the alkyls can be the same or different. Carboxamido includes, but is not limited to, —C(O)$NH_2$, —C(O)N(H)($CH_2CH_3$), —C(O)N$(CH_3)_2$ and —C(O)N($CH_3$)($CH_2CH_3$).

"Cycloalkyl" refers to a saturated, aliphatic, monovalent, monocyclic or polycyclic, hydrocarbon ring radical having from three to 25 (e.g., from three to 20, from three to 15, from three to 10, from three to eight) ring atoms. When there is an indication of the number of ring atoms in a cycloalkyl group, the cycloalkyl group has the indicated number of ring atoms. Thus, "($C_3$-$C_8$)cycloalkyl" means a ring radical having from three to eight ring atoms. Cycloalkyl includes, but is not limited to, cyclopropyl, cyclobutyl, cyclopentyl, cyclohexyl, and the like.

"Dialkylamino" refers to —N$(alkyl)_2$, wherein alkyl is as described herein. Each alkyl in a dialkylamino group can be the same as, for example, in —N$(CH_3)_2$, or different as, for example, in —N($CH_3$)($CH_2CH_3$).

"Heteroaryl" refers to a monocyclic or polycyclic (e.g., bicyclic, tricyclic), aromatic, hydrocarbon ring system having from five to 25 (e.g., from five to 20, from five to 15, from five to 10, 5 or 6) ring atoms, wherein at least one carbon atom (e.g., one, two, three, four or five) in the ring system has been replaced with a heteroatom selected from nitrogen, sulfur and oxygen. When there is an indication of the number of ring atoms in a heteroaryl group, the heteroaryl group has the indicated number of ring atoms. Thus, "($C_5$-$C_{15}$)heteroaryl" means a heterocyclic aromatic ring system having from five to 15 ring atoms consisting of carbon, nitrogen, sulfur and oxygen. In some embodiments, a heteroaryl contains 1, 2, 3 or 4 (e.g., 1, 2 or 3) heteroatoms independently selected from nitrogen, sulfur and oxygen. Monocyclic heteroaryls include, but are not limited to, furan, oxazole, thiophene, triazole, triazolone, triazene, thiadiazole, oxadiazole, imidazole, isothiazole, isoxazole, pyrazole, pyridazine, pyridine, pyrazine, pyrimidine, pyrrole, tetrazole and thiazole. Bicyclic heteroaryls include, but are not limited to, indolizine, indole, isoindole, indazole, benzimidazole, benzofuran, benzothiazole, purine, quinoline, isoquinoline, cinnoline, phthalazine, quinazoline, quinoxaline, naphthyridine and pteridine.

"Heterocyclyl" refers to a saturated, aliphatic, monocyclic or polycyclic (e.g., bicyclic, tricyclic), monovalent, hydrocarbon ring system having from three to 25 (e.g., from three to 20, from three to 15, from three to 10, from three to eight) ring atoms, wherein at least one carbon atom in the ring system (e.g., one, two, three, four or five) has been replaced with a heteroatom selected from nitrogen, sulfur and oxygen. When there is an indication of the number of ring atoms in a heterocyclyl group, the heterocyclyl group has the indicated number of ring atoms. Thus, "($C_3$-$C_5$)heterocyclyl" means a heterocyclic ring system having from three to eight ring atoms consisting of carbon, nitrogen, sulfur and oxygen. A heterocyclyl can be monocyclic, fused bicyclic, bridged bicyclic or polycyclic, but is typically monocyclic. In some embodiments, a heterocyclyl contains 1, 2, 3 or 4 (e.g., 1, 2 or 3) heteroatoms independently selected from nitrogen, sulfur and oxygen. When one heteroatom is sulfur, it can be optionally mono- or di-oxygenated (i.e., —S(O)— or —$S(O)_2$, respectively). Examples of monocyclic heterocyclyls include, but are not limited to, aziridine, azetidine, pyrrolidine, piperidine, piperazine, azepane, tetrahydrofuran, tetrahydropyran, morpholine, thiomorpholine, dioxide and oxirane.

"Halogen" and "halo" are used interchangeably herein, and each refers to fluorine, chlorine, bromine, or iodine. In some embodiments, halogen is selected from fluoro, chloro or bromo.

"Haloalkyl" refers to an alkyl radical wherein at least one hydrogen of the alkyl has been replaced by a halogen, and alkyl is as described herein. "Haloalkyl" includes mono, poly, and perhaloalkyl groups, wherein each halogen is independently selected from fluorine, chlorine, bromine and iodine (e.g., fluorine, chlorine and bromine). In one aspect, haloalkyl is perhaloalkyl (e.g., perfluoroalkyl). Haloalkyl includes, but is not limited to, trifluoromethyl and pentafluoroethyl.

"Haloalkoxy" refers to a haloalkyl radical attached through an oxygen linking atom, wherein haloalkyl is as described herein. Haloalkoxy includes, but is not limited to, trifluoromethoxy.

"Hydroxy" means —OH.

Groups described herein having two or more points of attachment (e.g., divalent, trivalent, or polyvalent; typically, divalent as, for example, in the heteroarylene group designated variable L) are designated by use of the suffix, "ene." For example, divalent heteroaryl groups are heteroarylene groups, and so forth.

It is understood that substituents on the compounds of the invention can be selected by one of ordinary skill in the art to provide compounds that are chemically stable and that can be readily synthesized by techniques known in the art, as well as those methods set forth below. The term "stable," as used herein, refers to compounds that are not substantially altered when subjected to conditions to allow for their production, detection and, in certain embodiments, recovery, purification and use for one or more of the purposes disclosed herein. Combinations of substituents envisioned by this invention are preferably those that result in the formation of stable or chemically feasible compounds.

A designated group is unsubstituted, unless otherwise indicated. When the term "substituted" precedes a designated group, it means that one or more hydrogens of the designated group are replaced with a suitable substituent. Unless otherwise indicated, an "optionally substituted" group or "substituted or unsubstituted" group can have a suitable substituent at each substitutable position of the group and, when more than one position in any given structure may be substituted with more than one substituent selected from a specified group, the substituent can be the same or different at every position. Alternatively, an "optionally substituted" group or "substituted or unsubstituted" group can be unsubstituted.

Suitable substituents for an optionally substituted or substituted or unsubstituted group include, but are not limited to, halo, hydroxy, cyano, nitro, alkyl, haloalkyl, alkoxy, haloalkoxy, alkenyl, alkenoxy, alkynyl, alkynoxy, $-(CH_2)_{0-2}$aryl, $-(CH_2)_{0-2}$heteroaryl, $-(CH_2)_{0-2}$cycloalkyl, $-(CH_2)_{0-2}$heterocyclyl, carboxy, $-(CH_2)_n-$ wherein n is 1, 2, 3, 4, or 5 (e.g., 1, 2 or 3), $-O(CH_2)_mO-$ wherein m is 1, 2, 3, 4 or 5 (e.g., 1, 2 or 3), amino, alkylamino, dialkylamino or carboxamido, or oxo. In some embodiments, suitable substituents are selected from halo, hydroxy, alkyl, haloalkyl, alkoxy, haloalkoxy, $-(CH_2)_{0-2}$aryl, $-(CH_2)_{0-2}$heteroaryl, $-(CH_2)_{0-2}$cycloalkyl, $-(CH_2)_{0-2}$heterocyclyl, carboxy or $-O(CH_2)_mO-$ wherein m is 1, 2, 3, 4 or 5 (e.g., 1, 2 or 3). In some embodiments, suitable substituents are selected from halo, alkyl, haloalkyl, amino, alkylamino, dialkylamino or carboxamido. In some embodiments, suitable substituents are selected from halo, hydroxy, cyano, nitro, alkyl, haloalkyl, alkoxy, haloalkoxy, alkenyl, alkenoxy, alkynyl, alkynoxy, carboxy, $-(CH_2)_n-$ wherein n is 1, 2, 3, 4, or 5 (e.g., 1, 2 or 3), $-O(CH_2)_mO-$ wherein m is 1, 2, 3, 4 or 5 (e.g., 1, 2 or 3), amino, alkylamino, dialkylamino or carboxamido, or oxo. In embodiments, suitable substituents are selected from halo, hydroxy, cyano, nitro, alkyl, haloalkyl, alkoxy, haloalkoxy, alkenyl, alkenoxy, alkynyl, alkynoxy, $-(CH_2)_{0-2}$aryl, $-(CH_2)_{0-2}$heteroaryl, $-(CH_2)_{0-2}$cycloalkyl, $-(CH_2)_{0-2}$heterocyclyl, $-(CH_2)_n-$ wherein n is 1, 2, 3, 4, or 5 (e.g., 1, 2 or 3), $-O(CH_2)_mO-$ wherein m is 1, 2, 3, 4 or 5 (e.g., 1, 2 or 3) or carboxamido, or oxo.

As used herein, the term "pharmaceutically acceptable salt" refers to those salts which are, within the scope of sound medical judgment, suitable for use in contact with the tissues of mammals without undue toxicity, irritation, allergic response and the like, and are commensurate with a reasonable benefit/risk ratio. Pharmaceutically acceptable salts are well known in the art. For example, S. M. Berge et al. describe pharmaceutically acceptable salts in detail in J. Pharmaceutical Sciences, 1977, 66, 1-19, the relevant teachings of which are incorporated herein by reference in their entirety. Pharmaceutically acceptable salts of the compounds described herein include salts derived from suitable inorganic and organic acids, and suitable inorganic and organic bases.

Examples of pharmaceutically acceptable acid addition salts are salts of an amino group formed with inorganic acids such as hydrochloric acid, hydrobromic acid, phosphoric acid, sulfuric acid and perchloric acid, or with organic acids such as acetic acid, oxalic acid, maleic acid, tartaric acid, citric acid, succinic acid or malonic acid, or by using other methods used in the art, such as ion exchange. Other pharmaceutically acceptable acid addition salts include adipate, alginate, ascorbate, aspartate, benzenesulfonate, benzoate, bisulfate, borate, butyrate, camphorate, camphorsulfonate, cinnamate, citrate, cyclopentanepropionate, digluconate, dodecylsulfate, ethanesulfonate, formate, fumarate, glucoheptonate, glycerophosphate, gluconate, glutarate, glycolate, hemisulfate, heptanoate, hexanoate, hydroiodide, hydroxybenzoate, 2-hydroxy-ethanesulfonate, hydroxymaleate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 2-phenoxybenzoate, phenylacetate, 3-phenylpropionate, phosphate, pivalate, propionate, pyruvate, salicylate, stearate, succinate, sulfate, tartrate, thiocyanate, p-toluenesulfonate, undecanoate, valerate salts, and the like. Either the mono-, di- or tri-acid salts can be formed, and such salts can exist in either a hydrated, solvated or substantially anhydrous form.

Salts derived from appropriate bases include salts derived from inorganic bases, such as alkali metal, alkaline earth metal, and ammonium bases, and salts derived from aliphatic, alicyclic or aromatic organic amines, such as methylamine, trimethylamine and picoline, or $N^+((C_1-C_4)alkyl)_4$ salts. Representative alkali or alkaline earth metal salts include sodium, lithium, potassium, calcium, magnesium, barium and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Compounds described herein can also exist as various "solvates" or "hydrates." A "hydrate" is a compound that exists in a composition with one or more water molecules. The composition can include water in stoichiometric quantities, such as a monohydrate or a dihydrate, or can include water in random amounts. A "solvate" is similar to a hydrate, except that a solvent other than water, such as methanol, ethanol, dimethylformamide, diethyl ether, or the like replaces water. Mixtures of such solvates or hydrates can also be prepared. The source of such solvate or hydrate can be from the solvent of crystallization, inherent in the solvent of preparation or crystallization, or adventitious to such solvent.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the present disclosure include isotopes of hydrogen, carbon, nitrogen and oxygen, such as $^{2}H$, $^{3}H$, $^{11}C$, $^{13}C$, $^{14}C$ and $^{15}N$, respectively. The present disclosure includes various isotopically labeled compounds as defined herein, for example, those into which radioactive isotopes, such as $^{3}H$ and $^{14}C$, or those into which non-radioactive isotopes, such as $^{2}H$ and $^{13}C$, have been incorporated. Such isotopically labelled compounds are useful in metabolic studies (with $^{14}C$), reaction kinetic studies (with, for example, $^{2}H$ or $^{3}H$), detection or imaging techniques, such as positron emission tomography (PET) or single-photon emission computed tomography (SPECT), including drug or substrate tissue distribution assays, or in radioactive treatment of patients. Further, substitution with heavier isotopes, particularly deuterium (i.e., $^{2}H$ or D) may afford certain therapeutic advantages resulting from greater metabolic stability, for example, increased in vivo half-life or reduced dosage requirements or an improvement in therapeutic index.

Isotopically labeled compounds of the present disclosure can generally be prepared by conventional techniques known to those skilled in the art by substituting an appropriate or readily available isotopically labeled reagent for a non-isotopically labeled reagent otherwise employed. Such compounds have a variety of potential uses, e.g., as standards and reagents in determining the ability of a potential pharmaceutical compound to bind to target proteins or receptors, or for imaging compounds of this disclosure bound to biological receptors in vivo or in vitro.

Compounds disclosed herein may have asymmetric centers, chiral axes, and chiral planes (e.g., as described in: E. L. Eliel and S. H. Wilen, Stereo-chemistry of Carbon Compounds, John Wiley & Sons, New York, 1994, pages 1119-1190), and occur as racemates, racemic mixtures, or as individual diastereomers or enantiomers, with all possible isomers and mixtures thereof, including optical isomers, being included in the present invention. When a disclosed compound is depicted by structure without indicating the stereochemistry, and the compound has one chiral center, it is to be understood that the structure encompasses one enantiomer or diastereomer of the compound separated or substantially separated from the corresponding optical isomer(s), a racemic mixture of the compound and mixtures enriched in one enantiomer or diastereomer relative to its corresponding optical isomer(s).

When introducing elements disclosed herein, the articles "a," "an," "the," and "said" are intended to mean that there are one or more of the elements. The terms "comprising," "having" and "including" are intended to be open-ended, and mean that there may be additional elements other than the listed elements.

Compounds

In a first embodiment, the compound is represented by the following structural (I)

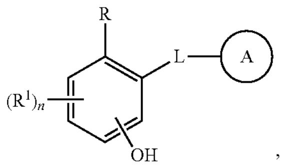

, or a pharmaceutically acceptable salt thereof, wherein:

Ring A is aryl (e.g., phenyl) or heteroaryl (e.g., oxazolyl, pyridinyl, benzothiazolyl, thiazolyl, pyrazolyl or benzofuranyl), and is optionally substituted with one or more substituents independently selected from halo, hydroxy, alkyl, haloalkyl, alkoxy, haloalkoxy, $—(CH_2)_{0-2}$-aryl, $—(CH_2)_{0-2}$-heteroaryl, $—(CH_2)_{0-2}$-cycloalkyl, $—(CH_2)_{0-2}$-heterocyclyl, carboxy or $—O(CH_2)_mO—$ (e.g., halo, hydroxy, alkyl, alkoxy, $—(CH_2)_{0-2}$-aryl, $—(CH_2)_{0-2}$-heteroaryl, $—(CH_2)_{0-2}$-cycloalkyl, $—(CH_2)_{0-2}$-heterocyclyl, carboxy or $—O(CH_2)_mO—$);

m is 1, 2, 3, 4 or 5;

L is $—C(O)(CH_2)_p—$, $—C(O)(CH_2)_p—O—$ or heteroarylene (e.g., oxazolylene, pyrimidinylene or pyrazolylene), wherein p is 0, 1 or 2 (e.g., 0 or 1), and R is hydrogen, halo, hydroxy, alkyl, haloalkyl, alkoxy, haloalkoxy, alkenoxy, alkynoxy, $—(CH_2)_{0-2}$-aryl, or $—(CH_2)_{0-2}$-heteroaryl (e.g., hydrogen, halo, hydroxy, alkyl, alkoxy, alkenoxy, alkynoxy, $—(CH_2)_{0-2}$-aryl, or $—(CH_2)_{0-2}$-heteroaryl); or L is $—C(O)(CH_2)_p—$, wherein p is 1 or 2, and R and a methylene carbon of $—C(O)(CH_2)_p—$, together with their intervening carbon atoms, form a fused ring (e.g., containing five, six, seven or eight members independently selected from carbon, oxygen, nitrogen and sulfur);

$R^1$ is halo, hydroxy, alkyl, haloalkyl, alkoxy, haloalkoxy, alkenoxy, alkynoxy, $—(CH_2)_{0-2}$-aryl, or $—(CH_2)_{0-2}$-heteroaryl (e.g., halo, hydroxy, alkyl, alkoxy, alkenoxy, alkynoxy, $—(CH_2)_{0-2}$-aryl, or $—(CH_2)_{0-2}$-heteroaryl); and n is 0, 1, 2 or 3, wherein the aryl and heteroaryl of R and $R^1$, and the heteroarylene of L are each optionally and independently substituted with one or more substituents (e.g., one, two or three substituents) selected from halo, alkyl, haloalkyl, amino, alkylamino, dialkylamino or carboxamido.

In a first aspect of the first embodiment, the compound is not AUY-922, VER-50589 or STA-9090, or a pharmaceutically acceptable salt of any of the foregoing. Values for the variables are as described in the first embodiment.

In a second aspect of the first embodiment, L is heteroarylene (e.g., $(C_5-C_6)$heteroarylene. Values for the remaining variables are as described in the first embodiment, or first aspect thereof.

In a third aspect of the first embodiment, L is oxazolylene, pyrazolylene, pyrimidinylene or triazolonylene. Values for the remaining variables are as described in the first embodiment, or first or second aspect thereof.

In a fourth aspect of the first embodiment, the heteroarylene of L is optionally substituted with one substituent selected from halo, alkyl, haloalkyl, amino, alkylamino, dialkylamino or carboxamido. Values for the variables are as described in the first embodiment, or first through third aspects thereof.

In a fifth aspect of the first embodiment, Ring A is phenyl. Values for the remaining variables are as described in the first embodiment, or first through fourth aspects thereof.

In a sixth aspect of the first embodiment, Ring A is heteroaryl (e.g., oxazolyl, pyridinyl, benzothiazolyl, thiazolyl, pyrazolyl or benzofuranyl). Values for the remaining variables are as described in the first embodiment, or first through fifth aspects thereof.

In a seventh aspect of the first embodiment, Ring A is indolyl, pyrazolyl, benzofuranyl, benzothiazolyl, or thiazolyl. Values for the remaining variables are as described in the first embodiment, or first through sixth aspects thereof.

In an eighth aspect of the first embodiment, m is 1, 2 or 3. Values for the remaining variables are as described in the first embodiment, or first through seventh aspects thereof.

In a ninth aspect of the first embodiment, n is 0, 1 or 2. Values for the remaining variables are as described in the first embodiment, or first through eighth aspects thereof.

In a tenth aspect of the first embodiment, R is hydrogen. Values for the remaining variables are as described in the first embodiment, or first through ninth aspects thereof.

In an eleventh aspect of the first embodiment, $R^1$ is halo, hydroxy, alkyl, alkoxy, alkenoxy, alkynoxy, $-(CH_2)_{0-2}$-aryl, or $-(CH_2)_{0-2}$-heteroaryl. Values for the remaining variables are as described in the first embodiment, or first through tenth aspects thereof.

A second embodiment is a compound represented by the following structural formula:

(II)

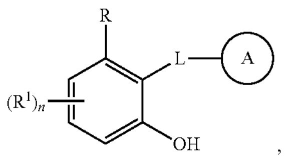

or a pharmaceutically acceptable salt thereof, wherein values for the variables are as described in the first embodiment, or any aspect thereof, or the fourth embodiment.

A third embodiment is a compound represented by the following structural formula:

(III)

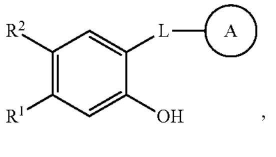

or a pharmaceutically acceptable salt thereof, wherein $R^2$ is hydrogen, halo, hydroxy, alkyl, haloalkyl, alkoxy, haloalkoxy, alkenoxy, alkynoxy, $-(CH_2)_{0-2}$-aryl, or $-(CH_2)_{0-2}$-heteroaryl. Values for the remaining variables are as described in the first embodiment, or any aspect thereof, or the fourth embodiment.

In a first aspect of the third embodiment, $R^1$ is hydroxy, alkoxy, haloalkoxy, alkenoxy or alkynoxy. Values for the remaining variables are as described in the first embodiment, or any aspect thereof, or the third or fourth embodiment.

In a second aspect of the third embodiment, $R^2$ is hydrogen, halo, alkyl or haloalkyl. Values for the remaining variables are as described in the first embodiment, or any aspect thereof, or the third embodiment, or the first aspect thereof, or the fourth embodiment.

In a fourth embodiment, the compound is represented by Structural Formula I, or a pharmaceutically acceptable salt thereof, wherein:

Ring A is substituted or unsubstituted aryl (e.g., phenyl) or substituted or unsubstituted heteroaryl (e.g., oxazolyl, pyridinyl, benzothiazolyl, thiazolyl, pyrazolyl or benzofuranyl);

L is $-C(O)(CH_2)_p-$, $-C(O)(CH_2)_p-O-$ or substituted or unsubstituted heteroarylene (e.g., oxazolylene, pyrimidinylene or pyrazolylene), wherein p is 0, 1 or 2 (e.g., 0 or 1), and R is hydrogen, halo, hydroxy, alkyl, haloalkyl, alkoxy, haloalkoxy, alkenoxy, alkynoxy, substituted or unsubstituted $-(CH_2)_{0-2}$-aryl, or substituted or unsubstituted $-(CH_2)_{0-2}$-heteroaryl; or L is $-C(O)(CH_2)_p-$, wherein p is 1 or 2, and R and a methylene carbon of $-C(O)(CH_2)_p-$, together with their intervening carbon atoms, form a substituted or unsubstituted fused ring (e.g., containing five, six, seven or eight members independently selected from carbon, oxygen, nitrogen and sulfur);

$R^1$ is halo, hydroxy, alkyl, haloalkyl, alkoxy, haloalkoxy, alkenoxy, alkynoxy, substituted or unsubstituted $-(CH_2)_{0-2}$-aryl, or substituted or unsubstituted $-(CH_2)_{0-2}$-heteroaryl; and n is 0, 1, 2 or 3. Alternative values and optional substituents for the variables are as described in the first, second or third embodiment, or any aspect thereof. Optional substituents for the variables further include those substituents described as suitable substituents herein.

Specific examples of compounds useful in the methods of the invention include any of the compounds of Appendices 1, 1', 2, 2', 3 and 4, or a pharmaceutically acceptable salt thereof, such as isocotoin, or a pharmaceutically acceptable salt thereof.

Compounds of Structural Formula I are readily obtainable by a person of ordinary skill in the art, as by chemical synthesis or through a commercial source. For example, many of the compounds of Structural Formula I and Appendices 1, 1', 2, 2', 3 and 4 are commercially available, for example, from the vendors indicated in Appendices 1, 1', 2, 2', 3 and 4.

Compositions

Also provided herein is a pharmaceutical composition comprising a compound disclosed herein (e.g., a compound of any one of Structural Formulas I, II and III; a compound of Appendix 1, 1', 2, 2', 3 or 4; isocotoin), or a pharmaceutically acceptable salt thereof, and a pharmaceutically acceptable carrier. The compositions can be used in the methods described herein, e.g., to supply a compound described herein, or a pharmaceutically acceptable salt thereof.

"Pharmaceutically acceptable carrier" refers to a non-toxic carrier or excipient that does not destroy the pharmacological activity of the agent with which it is formulated and is nontoxic when administered in doses sufficient to deliver an effective amount of the agent. Pharmaceutically acceptable carriers that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions described herein may be administered orally, parenterally (including subcutaneously, intramuscularly, intravenously, intradermally, by inhalation, topically, rectally, nasally and vaginally) or buccally, or via an implanted reservoir. The term "parenteral," as used herein, includes subcutaneous, intracutaneous, intravenous, intramuscular, intraocular, intravitreal, intra-articular, intra-arterial, intra-synovial, intrasternal, intrathecal, intralesional, intrahepatic, intraperitoneal intralesional and intracranial injection or infusion techniques. In some embodiments, provided compounds or compositions are administrable orally.

Compositions provided herein can be orally administered in any orally acceptable dosage form including, but not limited to, capsules, tablets, aqueous suspensions, dispersions and solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions and/or emulsions are required for oral use, the active ingredient can be suspended or dissolved in an oily phase and combined with emulsifying and/or suspending agents. If desired, certain sweetening, flavoring or coloring agents may also be added.

In some embodiments, an oral formulation is formulated for immediate release or sustained/delayed release.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders, such as carboxymethylcellulose, alginates, gelatin, polyvinylpyrrolidinone, sucrose, and acacia, (c) humectants such as glycerol, (d) disintegrating agents such as agar-agar, calcium carbonate, potato or tapioca starch, alginic acid, certain silicates, and sodium carbonate, (e) solution retarding agents such as paraffin, (f) absorption accelerators such as quaternary ammonium salts, (g) wetting agents, such as acetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Liquid dosage forms for oral administration include pharmaceutically acceptable emulsions, microemulsions, solutions, suspensions, syrups, and elixirs. Liquid dosage forms may contain inert diluents commonly used in the art, such as water or other solvents, solubilizing agents and emulsifiers, such as ethyl alcohol (ethanol), isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, or mixtures thereof. Besides inert diluents, the oral compositions can also include adjuvants such as wetting agents, emulsifying and suspending agents, sweetening, flavoring, coloring, perfuming, and preservative agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using excipients such as lactose or milk sugar, as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

A compound described herein, or a pharmaceutically acceptable salt thereof, can also be in micro-encapsulated form with one or more excipients, as noted above. In such solid dosage forms, the compound or pharmaceutically acceptable salt can be admixed with at least one inert diluent such as sucrose, lactose or starch. Such dosage forms can also comprise, as is normal practice, additional substances other than inert diluents, e.g., tableting lubricants and other tableting aids such a magnesium stearate and microcrystalline cellulose.

Compositions for oral administration may be designed to protect the active ingredient against degradation as it passes through the alimentary tract, for example, by an outer coating of the formulation on a tablet or capsule.

In another embodiment, a compound or pharmaceutically acceptable salt described herein can be provided in an extended (or "delayed" or "sustained") release composition. This delayed-release composition comprises the compound or pharmaceutically acceptable salt in combination with a delayed-release component. Such a composition allows targeted release of a provided agent into the lower gastrointestinal tract, for example, into the small intestine, the large intestine, the colon and/or the rectum. In certain embodiments, a delayed-release composition further comprises an enteric or pH-dependent coating, such as cellulose acetate phthalates and other phthalates (e.g., polyvinyl acetate phthalate, methacrylates (Eudragits)). Alternatively, the delayed-release composition provides controlled release to the small intestine and/or colon by the provision of pH-sensitive methacrylate coatings, pH-sensitive polymeric microspheres, or polymers which undergo degradation by hydrolysis. The delayed-release composition can be formulated with hydrophobic or gelling excipients or coatings. Colonic delivery can further be provided by coatings which are digested by bacterial enzymes such as amylose or pectin, by pH-dependent polymers, by hydrogel plugs swelling with time (Pulsincap), by time-dependent hydrogel coatings and/or by acrylic acid-linked-to-azoaromatic bonds coatings.

Compositions described herein can also be administered subcutaneously, intraperitoneally or intravenously. Compositions described herein for intravenous, subcutaneous, or intraperitoneal injection may contain an isotonic vehicle such as sodium chloride injection, Ringer's injection, dextrose injection, dextrose and sodium chloride injection, lactated Ringer's injection, or other vehicles known in the art.

Compositions described herein can also be administered in the form of suppositories for rectal administration. These can be prepared by mixing a compound or pharmaceutically acceptable salt described herein with a suitable non-irritating excipient that is solid at room temperature but liquid at rectal temperature and, therefore, will melt in the rectum to release the drug. Such materials include cocoa butter, beeswax and polyethylene glycols.

Compositions described herein can also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches can also be used.

For other topical applications, the compositions can be formulated in a suitable ointment containing the active component suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water and penetration enhancers. Alternatively, compositions can be formulated in a suitable lotion or cream containing the active agent suspended or dissolved in one or more pharmaceutically acceptable carriers. Alternatively, the composition can be formulated with a suitable lotion or cream containing the active agent suspended or dissolved in a carrier with suitable emulsifying agents. In some embodiments, suitable carriers include, but are not limited to, mineral oil, sorbitan monostearate, polysorbate 60, cetyl esters wax, cetearyl alcohol, 2-octyldodecanol, benzyl alcohol and water. In other embodiments, suitable carriers include, but are not limited to, penetration enhancers.

For ophthalmic use, compositions can be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic use, the compositions can be formulated in an ointment such as petrolatum.

Compositions can also be administered by nasal aerosol or inhalation, for example, for the treatment of asthma. Such compositions are prepared according to techniques well-known in the art of pharmaceutical formulation and can be prepared as solutions in saline, employing benzyl alcohol or other suitable preservatives, absorption promoters to enhance bioavailability, fluorocarbons, and/or other conventional solubilizing or dispersing agents. Without wishing to be bound by any particular theory, it is believed that local delivery of a composition described herein, as can be achieved by nasal aerosol or inhalation, for example, can reduce the risk of systemic consequences of the composition.

The amount of a compound described herein, or a pharmaceutically acceptable salt thereof, that can be combined with the carrier materials to produce a composition in a single dosage form will vary depending upon the host treated, the particular mode of administration and the activity of the agent employed. Preferably, compositions should be formulated so that a dosage of from about 0.01 mg/kg to about 100 mg/kg body weight/day of the compound, or pharmaceutically acceptable salt thereof, can be administered to a subject receiving the composition.

The desired dose may conveniently be administered in a single dose or as multiple doses administered at appropriate intervals such that, for example, the agent is administered 1, 2, 3, 4, 5, 6 or more times per day. The daily dose can be divided, especially when relatively large amounts are administered, or as deemed appropriate, into several, for example 2, 3, 4, 5, 6 or more, administrations.

It should also be understood that a specific dosage and treatment regimen for any particular patient will depend upon a variety of factors, including the activity of the specific agent employed, the age, body weight, general health, sex, diet, time of administration, rate of excretion, drug combination, the judgment of the treating physician and the severity of the particular disease being treated. The amount of a compound or pharmaceutically acceptable salt in the composition will also depend upon the particular compound or pharmaceutically acceptable salt in the composition.

Other pharmaceutically acceptable carriers, adjuvants and vehicles that can be used in the compositions of this invention include, but are not limited to, ion exchangers, alumina, aluminum stearate, lecithin, self-emulsifying drug delivery systems (SEDDS) such as d-α-tocopherol polyethylene glycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives can also be advantageously used to enhance delivery of agents described herein.

The compositions can be in the form of a sterile injectable preparation, for example, as a sterile injectable aqueous or oleaginous suspension. This suspension can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium. For this purpose, any bland fixed oil can be employed including synthetic mono- or diglycerides. Fatty acids, such as oleic acid and its glyceride derivatives, are useful in the preparation of injectables, as are natural pharmaceutically acceptable oils, such as olive oil or castor oil, especially in their polyoxyethylated versions. These oil solutions or suspensions can also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms can also be used for the purposes of formulation.

In some embodiments, compositions comprising a compound described herein, or a pharmaceutically acceptable salt thereof, can also include one or more other therapeutic agents (e.g., one or more other anti-viral agents, such as ribavirin), e.g., in combination.

Also provided herein is a kit comprising a compound described herein, or a pharmaceutically acceptable salt thereof, and an additional therapeutic agent(s) (e.g., an additional anti-viral agent, such as ribavirin). In one embodiment, the kit comprises an effective amount of a compound described herein, or a pharmaceutically acceptable salt thereof, to treat a disease, disorder or condition described herein, and an effective amount of an additional therapeutic agent(s) to treat the disease, disorder or condition. In some embodiments, the kit further comprises written instructions for administering the compound, or a pharmaceutically acceptable salt thereof, and the additional agent(s) to a subject to treat a disease, disorder or condition described herein.

The compositions described herein can, for example, be administered by injection, intravenously, intraarterially, intraocularly, intravitreally, subdermally, orally, buccally, nasally, transmucosally, topically, in an ophthalmic preparation, or by inhalation, with a dosage ranging from about 0.5 mg/kg to about 100 mg/kg of body weight or, alternatively, in a dosage ranging from about 1 mg/dose to about 1000 mg/dose, every 4 to 120 hours, or according to the requirements of the particular agent.

Typically, the compositions will be administered from about 1 to about 6 times per day or, alternatively, as a continuous infusion. The amount of active ingredient that can be combined with a carrier material to produce a single dosage form will vary depending upon the host treated and the particular mode of administration. A typical preparation will contain from about 1% to about 99%, e.g., from about 5% to about 95%, from about 1% to about 75%, from about 1% to about 50%, from about 1% to about 40%, from about 1% to about 30%, from about 1% to about 25%, from about 1% to about 20%, from about 5% to about 75%, from about 5% to about 50%, from about 5% to about 40%, from about 5% to about 30%, from about 5% to about 25%, from about 10% to about 75%, from about 10% to about 50%, from about 10% to about 40%, from about 10% to about 30% or from about 10% to about 25%, active compound (w/w). Alternatively, a preparation can contain from about 20% to about 80% active compound (w/w).

Doses lower or higher than those recited above may be required. Specific dosage and treatment regimens for any particular patient will depend upon a variety of factors, including the activity of the specific agent employed, the age, body weight, general health status, sex, diet, time of administration, rate of excretion, drug combination, the severity and course of the disease, condition or symptoms, the patient's disposition to the disease, condition or symptoms, and the judgment of the treating physician.

Methods

One embodiment provides a method of inhibiting replication of a virus (e.g., a positive-sense, single-stranded RNA virus; a flavivirus; a HEV), comprising contacting a cell infected with the virus (e.g., one or more viral particles) with a compound disclosed herein (e.g., a compound represented by Structural Formula (I), (II) or (III); a compound of Appendix 1, 1', 2, 2', 3 or 4; isocotoin), or a pharmaceutically acceptable salt thereof. In some aspects, the virus is a positive-sense, single-stranded RNA virus. In some aspects, the virus is an HEV. In some aspects, the virus is an HCV. In some aspects, the virus is a yellow fever virus. In some aspects, the method is performed in vitro. In some aspects, the method is performed ex vivo. In some aspects, the method is performed in vivo as, for example, when the cell is in a subject (e.g., a patient). In some aspects, the cell is a hepatocyte (e.g., a Huh7 cell), a gut epithelial cell or a central nervous system (CNS) cell. It has been shown that gut epithelial cells can be infected in vitro with HEV. See Marion, O., et al. "Hepatitis E virus replication in human intestinal cells," Gut 2020 May; 69(5):901-910, the entire contents of which are incorporated herein by reference. However, HEV's cellular tropism may also span into CNS cells. See, for example, Shi, R., et al., "Evidence of Hepatitis E virus breaking through the blood-brain barrier and replicating in the central nervous system," *J. Viral. Hepat.* 2016; 23(11):930-939, the entire contents of which are incorporated herein by reference.

A positive-sense, single-stranded RNA virus is a virus whose genetic material consists of positive-sense, single-stranded RNA. Positive-sense, single-stranded RNA viruses include the hepatitis (e.g., hepatitis C, hepatitis E) virus, flaviviruses (e.g., yellow fever virus, West Nile virus, Dengue virus, Zika virus), rhinoviruses and coronaviruses (e.g., severe acute respiratory syndrome (SARS) coronavirus, Middle East respiratory syndrome-related (MERS) coronavirus).

HEV is a positive-sense single-stranded RNA virus of the Hepeviridae family measuring approximately 7.2 kB in length. The virus contains three open reading frames (ORFs), of which ORF1 is the largest (approximately 5,100 base pairs), and encodes a number of viral proteins including a methyltransferase, putative cysteine protease (PCP) region, RNA helicase, and RNA-dependent RNA polymerase (RdRp) (FIG. 1). These proteins play critical roles in viral gene expression, transcription, and interactions with host proteins. ORF2 of HEV encodes the viral capsid protein, and ORF3 encodes a small protein essential for viral egress. During viral genomic replication, an intermediate, negative-sense RNA template is used to transcribe several-fold greater amounts of positive-sense RNA strands.

The strains of HEV affecting humans fall under the genus *Orthohepeviridae* and are primarily transmitted through contaminated drinking water or the consumption of infected pork, venison, or wild boar meat. HEV infection most commonly manifests as self-limiting, acute hepatitis in healthy individuals, typically lasting for a month. However, pregnant women and immunocompromised individuals experience more severe symptoms. Pregnant women have up to a 30% mortality rate in the third trimester from HEV infection, particularly from genotype 1 strains of the virus. Immunocompromised individuals exposed to HEV can develop chronic infection, leading to the rapid progression of liver cirrhosis in as little as two years.

Another embodiment provides a method of treating a viral infection (e.g., an HEV infection) in a subject in need thereof, comprising administering to the subject an effective amount of a compound disclosed herein (e.g., a compound represented by Structural Formula (I), (II) or (III); a compound of Appendix 1, 1', 2, 2', 3 or 4; isocotoin), or a pharmaceutically acceptable salt thereof. In some aspects, the viral infection is caused by a positive-sense, single-stranded RNA virus (e.g., a flavivirus). In some aspects, the viral infection is caused by an HEV. In some aspects, the viral infection is caused by an HCV. In some aspects, the viral infection is caused by a yellow fever virus. In some aspects, the viral infection is an acute viral infection (e.g., acute HEV infection). In some aspects, the viral infection is a chronic viral infection (e.g., chronic HEV infection).

"Treating," as used herein, refers to taking steps to deliver a therapy to a subject, such as a human, in need thereof "Treating" includes inhibiting the disease or condition (e.g., as by slowing or stopping its progression or causing regression of the disease or condition), and/or relieving the symptoms resulting from the disease or condition.

As used herein, "subject" includes humans, domestic animals, such as laboratory animals (e.g., dogs, monkeys, pigs, rats, mice, etc.), household pets (e.g., cats, dogs, rabbits, etc.) and livestock (e.g., pigs, cattle, sheep, goats, horses, etc.), and non-domestic animals. In some embodiments, a subject is a human.

A subject is "in need of" a treatment if such subject would benefit from such treatment (e.g., biologically, medically or in quality of life).

"Patient" refers to a human subject.

In some embodiments, a subject is immunocompromised. In some embodiments, a subject is pregnant.

"An effective amount" is an amount effective, at dosages and for periods of time necessary, to achieve a desired therapeutic result (e.g., treatment, healing, inhibition or amelioration of physiological response or condition, etc.). The full therapeutic effect does not necessarily occur by administration of one dose, and may occur only after administration of a series of doses. Thus, an effective amount may be administered in one or more administrations. An effective amount may vary according to factors such as disease state, age, sex, and weight of a subject, mode of administration and the ability of a therapeutic, or combination of therapeutics, to elicit a desired response in a subject. An effective amount of an agent to be administered can be determined by a clinician of ordinary skill using the guidance provided herein and other methods known in the art.

Suitable dosages can be from about 0.001 mg/kg to about 100 mg/kg, from about 0.01 mg/kg to about 100 mg/kg, from about 0.01 mg/kg to about 10 mg/kg, from about 0.01 mg/kg to about 1 mg/kg body weight per treatment, for example, administered one, two, three, four, five or six, preferably, one, two or three, times per day. Determining the dosage for a particular agent, subject and disease is well within the abilities of one of skill in the art. Preferably, the dosage does not cause or produces minimal adverse side effects.

A compound described herein, or a pharmaceutically acceptable salt thereof, or a composition described herein can be administered via a variety of routes of administration, including, for example, oral, dietary, topical, transdermal, rectal, parenteral (e.g., intra-arterial, intravenous, intramuscular, subcutaneous injection, intradermal injection), intravenous infusion and inhalation (e.g., intrabronchial, intranasal or oral inhalation, intranasal drops) routes of administration, depending on the compound and the particular disease to be treated. Administration can be local or systemic as indicated. The preferred mode of administration can vary depending on the particular compound, pharmaceutically acceptable salt or composition chosen.

Also provided herein is a method of inhibiting heat shock protein 90 in a cell, comprising contacting the cell with a compound disclosed herein (e.g., a compound represented by Structural Formula (I), (II) or (III); a compound of Appendix 1, 1', 2, 2', 3 or 4; isocotoin), or a pharmaceutically acceptable salt thereof. In some aspects, the method is performed in vitro. In some aspects, the method is performed ex vivo. In some aspects, the method is performed in vivo as, for example, when the cell is in a subject (e.g., a patient). In some aspects, the cell is a hepatocyte (e.g., a Huh7 cell).

Also provided herein is a method of treating a heat shock protein 90-mediated disease or condition in a subject in need thereof, comprising administering to the subject an effective amount of a compound disclosed herein (e.g., a compound represented by Structural Formula (I), (II) or (III); a compound of Appendix 1, 1', 2, 2', 3 or 4; isocotoin), or a pharmaceutically acceptable salt thereof. In some aspects, the heat shock protein 90-mediated disease or condition is a viral infection, such as any of the viral infections disclosed herein.

A "heat shock protein 90-mediated disease or condition" is any disease or condition directly or indirectly regulated by heat shock protein 90. Examples of heat shock protein 90-mediated diseases or conditions include cancer (e.g., solid tumors, hematological cancers), neurodegenerative diseases, inflammatory diseases or conditions and viral infections (such as the viral infections disclosed herein).

Examples of cancer treatable according to the methods described herein include Acute Lymphoblastic Leukemia (ALL); Acute Myeloid Leukemia (AML); Adrenocortical Carcinoma; Adrenocortical Carcinoma, Childhood; AIDS-Related Cancer (e.g., Kaposi Sarcoma, AIDS-Related Lymphoma, Primary CNS Lymphoma); Anal Cancer; Appendix Cancer; Astrocytomas, Childhood; Atypical Teratoid/Rhabdoid Tumor, Childhood, Central Nervous System; Basal Cell Carcinoma of the Skin; Bile Duct Cancer; Bladder Cancer; Bladder Cancer, Childhood; Bone Cancer (including Ewing Sarcoma, Osteosarcoma and Malignant Fibrous Histiocytoma); Brain Tumors/Cancer; Breast Cancer; Burkitt Lymphoma; Carcinoid Tumor (Gastrointestinal); Carcinoid Tumor, Childhood; Cardiac (Heart) Tumors, Childhood; Embryonal Tumors, Childhood; Germ Cell Tumor, Childhood; Primary CNS Lymphoma; Cervical Cancer; Childhood Cervical Cancer; Cholangiocarcinoma; Chordoma, Childhood; Chronic Lymphocytic Leukemia (CLL); Chronic Myelogenous Leukemia (CML); Chronic Myeloproliferative Neoplasms; Colorectal Cancer; Childhood Colorectal Cancer; Craniopharyngioma, Childhood; Cutaneous T-Cell Lymphoma (e.g., Mycosis Fungoides and Sezary Syndrome); Ductal Carcinoma In Situ (DCIS); Embryonal Tumors, Central Nervous System, Childhood; Endometrial Cancer (Uterine Cancer); Ependymoma, Childhood; Esophageal Cancer; Childhood Esophageal Cancer; Esthesioneuroblastoma; Ewing Sarcoma; Extracranial Germ Cell Tumor, Childhood; Extragonadal Germ Cell Tumor; Eye Cancer; Childhood Intraocular Melanoma; Intraocular Melanoma; Retinoblastoma; Fallopian Tube Cancer; Fibrous Histiocytoma of Bone, Malignant, and Osteosarcoma; Gallbladder Cancer; Gastric (Stomach) Cancer; Childhood Gastric (Stomach) Cancer; Gastrointestinal Carcinoid Tumor; Gastrointestinal Stromal Tumors (GIST); Childhood Gastrointestinal Stromal Tumors; Germ Cell Tumors; Childhood Central Nervous System Germ Cell Tumors (e.g., Childhood Extracranial Germ Cell Tumors, Extragonadal Germ Cell Tumors, Ovarian Germ Cell Tumors, Testicular Cancer); Gestational Trophoblastic Disease; Hairy Cell Leukemia; Head and Neck Cancer; Heart Tumors, Childhood; Hepatocellular (Liver) Cancer; Histiocytosis, Langerhans Cell; Hodgkin Lymphoma; Hypopharyngeal Cancer; Intraocular Melanoma; Childhood Intraocular Melanoma; Islet Cell Tumors, Pancreatic Neuroendocrine Tumors; Kaposi Sarcoma; Kidney (Renal Cell) Cancer; Langerhans Cell Histiocytosis; Laryngeal Cancer; Leukemia; Lip and Oral Cavity Cancer; Liver Cancer; Lung Cancer (Non-Small Cell and Small Cell); Childhood Lung Cancer; Lymphoma; Male Breast Cancer; Malignant Fibrous Histiocytoma of Bone and Osteosarcoma; Melanoma; Childhood Melanoma; Melanoma, Intraocular (Eye); Childhood Intraocular Melanoma; Merkel Cell Carcinoma; Mesothelioma, Malignant; Childhood Mesothelioma; Metastatic Cancer; Metastatic Squamous Neck Cancer with Occult Primary; Midline Tract Carcinoma With NUT Gene Changes; Mouth Cancer; Multiple Endocrine Neoplasia Syndromes; Multiple Myeloma/Plasma Cell Neoplasms; Mycosis Fungoides; Myelodysplastic Syndromes, Myelodysplastic/Myeloproliferative Neoplasms; Myelogenous Leukemia, Chronic (CML); Myeloid Leukemia, Acute (AML); Myeloproliferative Neoplasms, Chronic; Nasal Cavity and Paranasal Sinus Cancer; Nasopharyngeal Cancer; Neuroblastoma; Non-Hodgkin Lymphoma; Non-Small Cell Lung Cancer; Oral Cancer, Lip and Oral Cavity Cancer and Oropharyngeal Cancer; Osteosarcoma and Malignant Fibrous Histiocytoma of Bone; Ovarian Cancer; Childhood Ovarian Cancer; Pancreatic Cancer; Childhood Pancreatic Cancer; Pancreatic Neuroendocrine Tumors; Papillomatosis (Childhood Laryngeal); Paraganglioma; Childhood Paraganglioma; Paranasal Sinus and Nasal Cavity Cancer; Parathyroid Cancer; Penile Cancer; Pharyngeal Cancer; Pheochromocytoma; Childhood Pheochromocytoma; Pituitary Tumor; Plasma Cell Neoplasm/Multiple Myeloma; Pleuropulmonary Blastoma; Pregnancy and Breast Cancer; Primary Central Nervous System (CNS) Lymphoma; Primary Peritoneal Cancer; Prostate Cancer; Rectal Cancer; Recurrent Cancer; Renal Cell (Kidney) Cancer; Retinoblastoma; Rhabdomyosarcoma, Childhood; Salivary Gland Cancer; Sarcoma (e.g., Childhood Rhabdomyosarcoma, Childhood Vascular Tumors, Ewing Sarcoma, Kaposi Sarcoma, Osteosarcoma (Bone Cancer), Soft Tissue Sarcoma, Uterine Sarcoma); Sezary Syndrome; Skin Cancer; Childhood Skin Cancer; Small Cell Lung Cancer; Small Intestine Cancer; Soft Tissue Sarcoma; Squamous Cell Carcinoma of the Skin; Squamous Neck Cancer with Occult Primary, Metastatic; Stomach (Gastric) Cancer; Childhood Stomach (Gastric) Cancer; T-Cell Lymphoma, Cutaneous (e.g., Mycosis Fungoides and Sezary Syndrome); Testicular Cancer; Childhood Testicular Cancer; Throat Cancer (e.g., Nasopharyngeal Cancer, Oropharyngeal Cancer, Hypopharyngeal Cancer); Thymoma and Thymic Carcinoma; Thyroid Cancer; Transitional Cell Cancer of the Renal Pelvis and Ureter; Ureter and Renal Pelvis, Transitional Cell Cancer; Urethral Cancer; Uterine Cancer, Endometrial; Uterine Sarcoma; Vaginal Cancer; Childhood Vaginal Cancer; Vascular Tumors; Vulvar Cancer; and Wilms Tumor and Other Childhood Kidney Tumors.

Metastases of the aforementioned cancers can also be treated in accordance with the methods described herein. In some embodiments, the cancer is a metastatic cancer.

Examples of neurodegenerative diseases treatable according to the methods described herein include Alzheimer's disease, Parkinson's disease, Huntington's disease, amyotrophic lateral sclerosis, prion disease, spinocerebellar ataxia, spinal muscular atrophy and motor neuron disease.

Examples of inflammatory diseases or conditions treatable according to the methods described herein include multiple sclerosis, Goodpasture syndrome, psoriasis, ankylosing spondylitis, antiphospholipid antibody syndrome, gout, arthritis (e.g., rheumatoid arthritis), myositis, scleroderma, Sjogren's syndrome, systemic lupus erythematosus and vasculitis.

In an aspect of any of the methods disclosed herein, the compound is not AUY-922, VER-50589, STA-9090 or 17-AAG (e.g., AUY-922, VER-50589 or STA-9090), or a pharmaceutically acceptable salt of any of the foregoing.

A compound described herein, or a pharmaceutically acceptable salt thereof, can also be administered in combination with one or more other therapies (e.g., additional anti-viral agent(s), such as ribavirin). When administered in a combination therapy, the compound, or pharmaceutically acceptable salt thereof, can be administered before, after or concurrently with the other therapy (e.g., additional anti-viral agent(s)). When co-administered simultaneously (e.g., concurrently), the compound, or pharmaceutically acceptable salt thereof, and other therapy can be in separate formulations or the same formulation. Alternatively, the compound, or pharmaceutically acceptable salt thereof, and other therapy can be administered sequentially, e.g., as separate compositions, within an appropriate time frame as determined by a skilled clinician (e.g., a time sufficient to allow an overlap of the pharmaceutical effects of the therapies).

In some embodiments, a method described herein further comprises contacting the cell with an additional therapeutic agent (e.g., an additional anti-viral agent, such as ribavirin).

In some embodiments, a method described herein further comprises administering to the subject an effective amount of an additional therapeutic agent (e.g., an additional anti-viral agent, such as ribavirin).

Exemplification

Treatment options for HEV infection are limited. In patients who develop chronic hepatitis E while taking immunosuppressive drugs (e.g., after receiving organ transplantation), a reduction in the immunosuppressive regimen is first attempted. This results in clearance of the virus in one-third of patients. When this is not successful, patients are typically treated with ribavirin, a nucleoside analog and broad-spectrum antiviral, and/or pegylated IFN-α (pegIFN-α). pegIFN-α is less commonly used, since it is associated with severe side effects and can lead to transplant rejection in organ transplant recipients. Ribavirin monotherapy is 78% effective in clearing chronic HEV infection; however, it is highly teratogenic and cannot be used in pregnant patients. Furthermore, HEV strains with "fitness-enhancing" mutations have been identified in patients showing clinical resistance to ribavirin treatment. There are currently no other clinically approved drugs for hepatitis E.

Methods and compositions for inhibiting HEV are disclosed in International Publication No. WO 2018/057773, the entire contents of which are incorporated herein by reference.

Figure 2A:
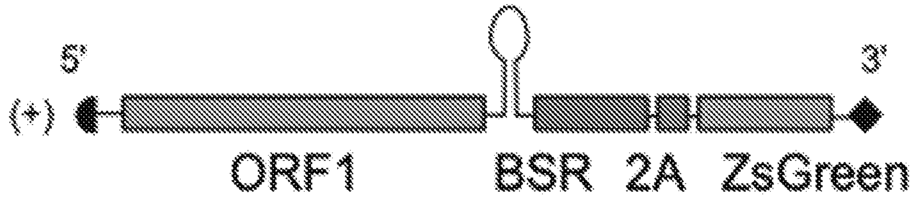
FIGS. 2A-2C. Characterization of Huh7 Kernow C1 p6-BSR/ZsGreen.
Figure 2B:
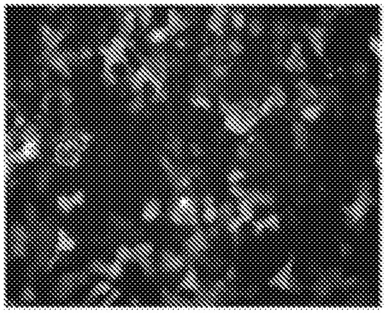
Figure 2C:
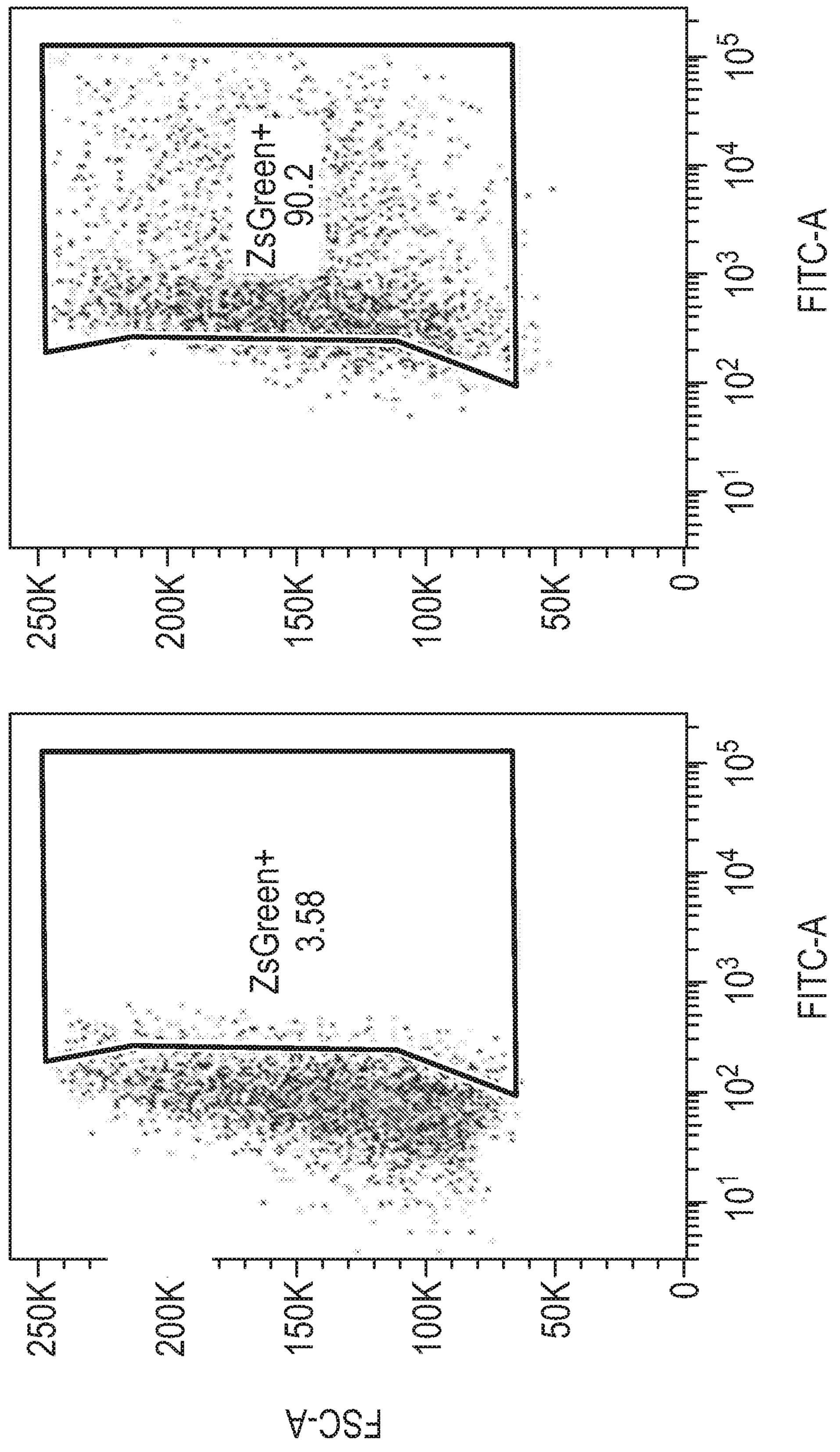
Figure 3A:
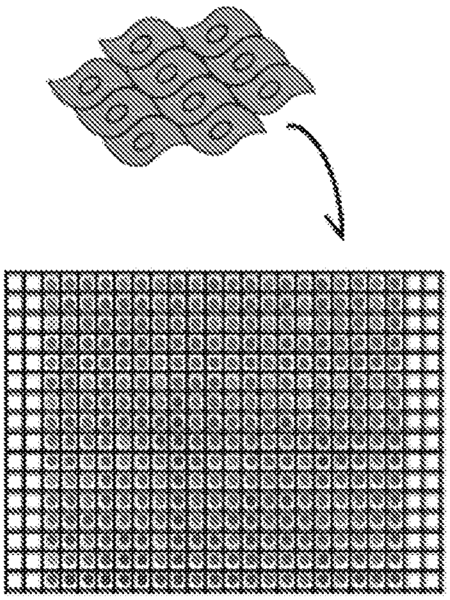
FIGS. 3A-3E. Schematic of replicon-based compound screening assay.
Figure 3B:
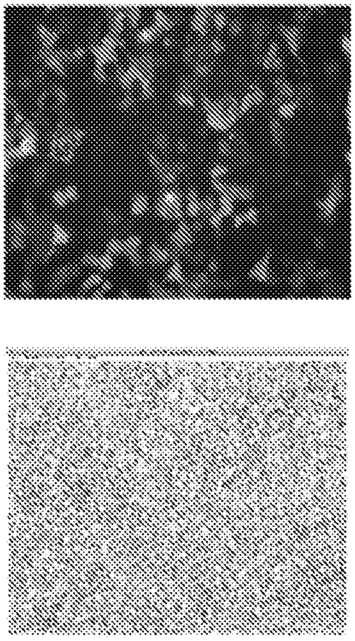
Figure 3C:
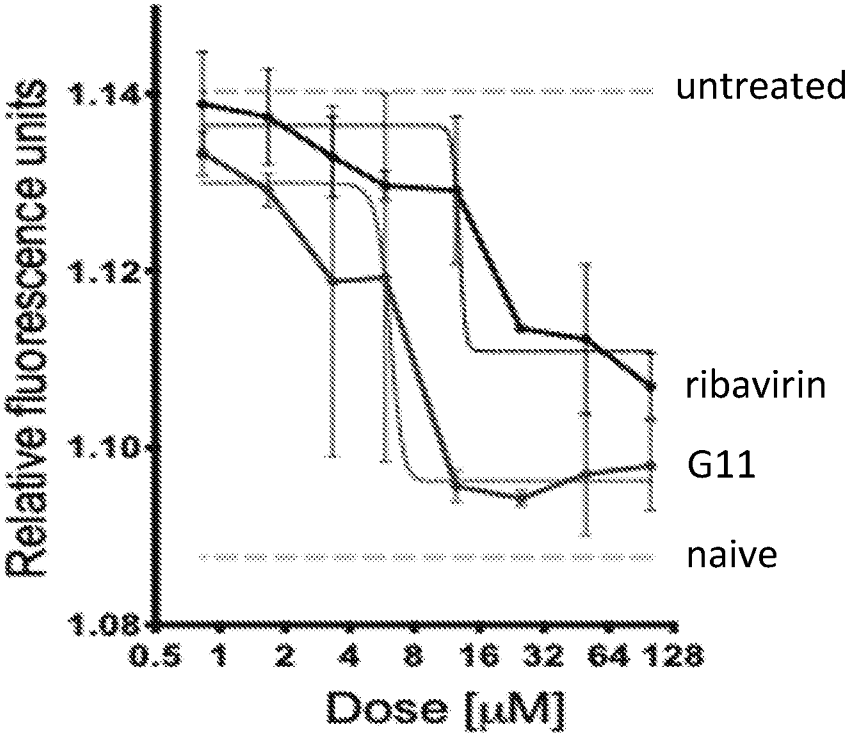
Figure 3D:
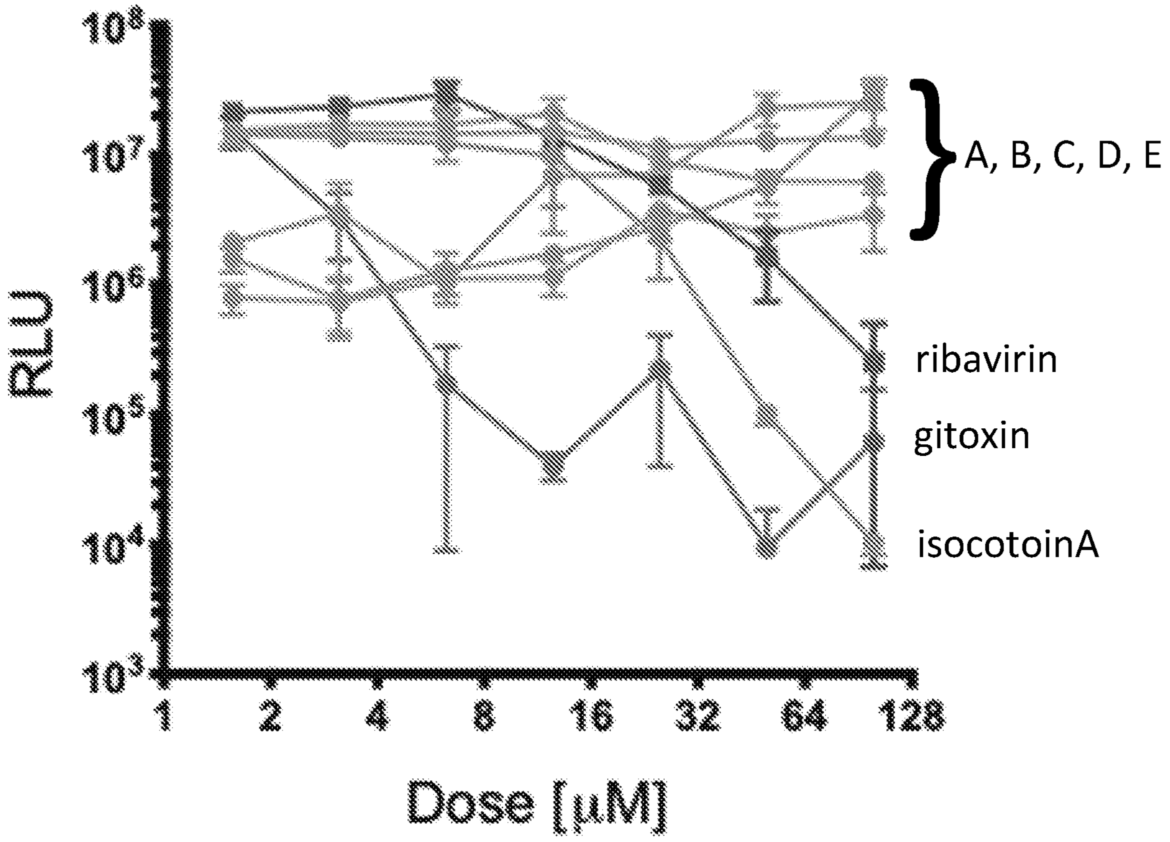
Figure 3E:
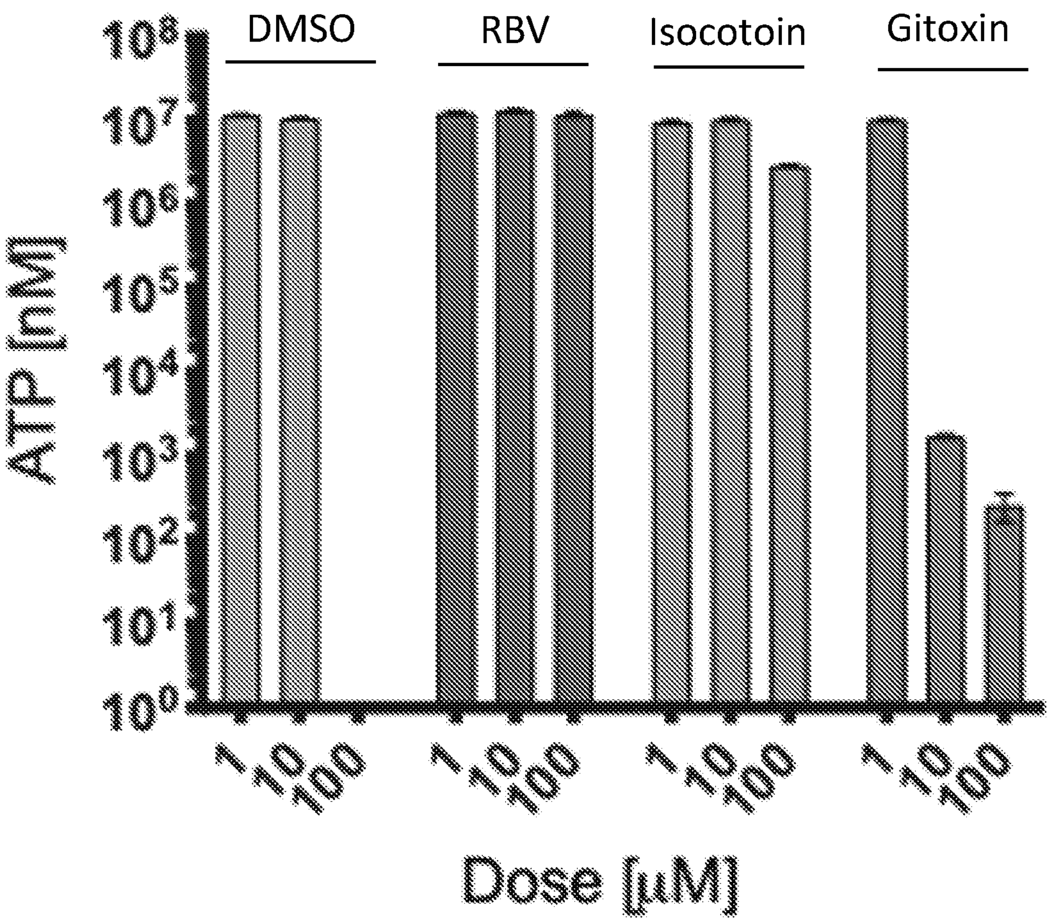

Replicon-Based High-Throughput Screening Assay to Identify Compounds Inhibiting HEV Gene Expression, Transcription, (Proteolytic Processing), Genomic Replication To identify small molecules with antiviral activity against HEV, proteins in ORF1 were targeted[14-17]. A replicon-based screening assay was used in which ORFs 2 and 3 of HEV, which encode the capsid protein and an ion channel required for viral egress respectively, were replaced in the viral genome with blasticidin resistance-conferring and ZsGreen fluorescent reporters (FIGS. 2A-2C)[18, 19]. Approximately 60,000 small molecules from the Princeton University Small Molecule Screening Center were tested against the replicon genome, with decreased fluorescence used as a readout to indicate inhibition of genomic replication (FIGS. 3A-3E).

Briefly, replicon-expressing cells were seeded in 384-well format and treated with a 50 μM dose of each compound for four days. A GFP channel image and bright-field image were taken of each well on day 4 using a Perkin Elmer Operetta High-Content Imaging System. Fluorescence levels in the GFP channel images were quantified using a custom Python script (publicly sourced at: https://github.com/aploss/PLO-CUS), and decreased fluorescence was used as a metric to select hits with putative antiviral activity. The bright-field images were used to remove false positive hits that showed decreased fluorescence due to cytotoxicity, resulting in 37 non-cytotoxic hits from the high-throughput assay. Through dose titration assays on the hits, isocotoin was identified as a promising therapeutic candidate against HEV replication.

Isocotoin Inhibits Genetically Diverse HEV Genotypes and Other (+)-Sense RNA Viruses.

Figure 4A:
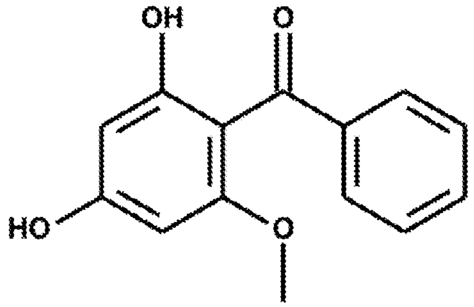
FIGS. 4A-4G. Isocotoin inhibits replication of p6/Gluc.
Figure 4B:
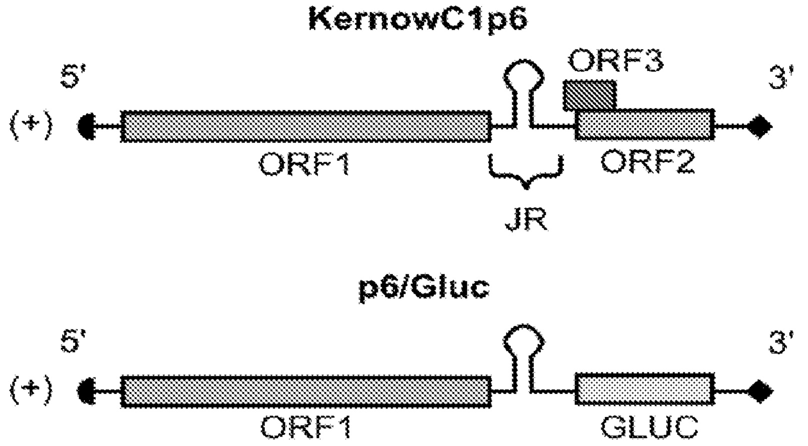
Figure 4C:
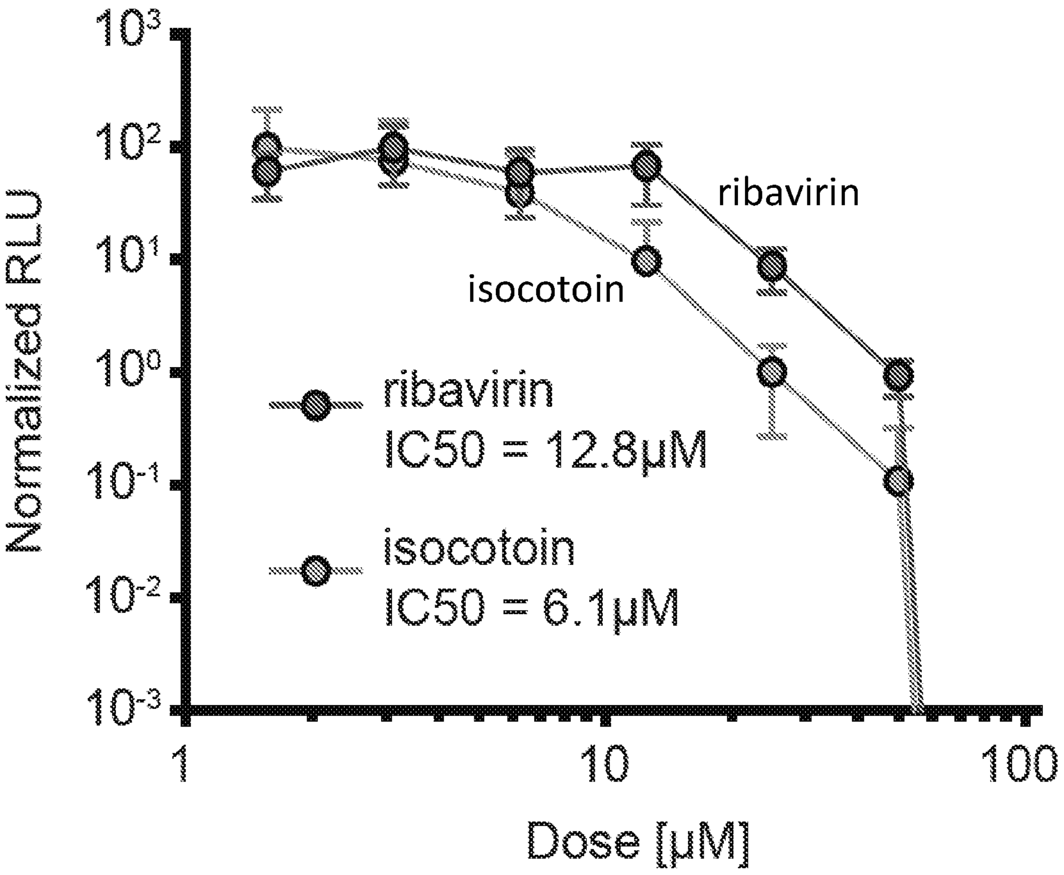
Figure 4D:
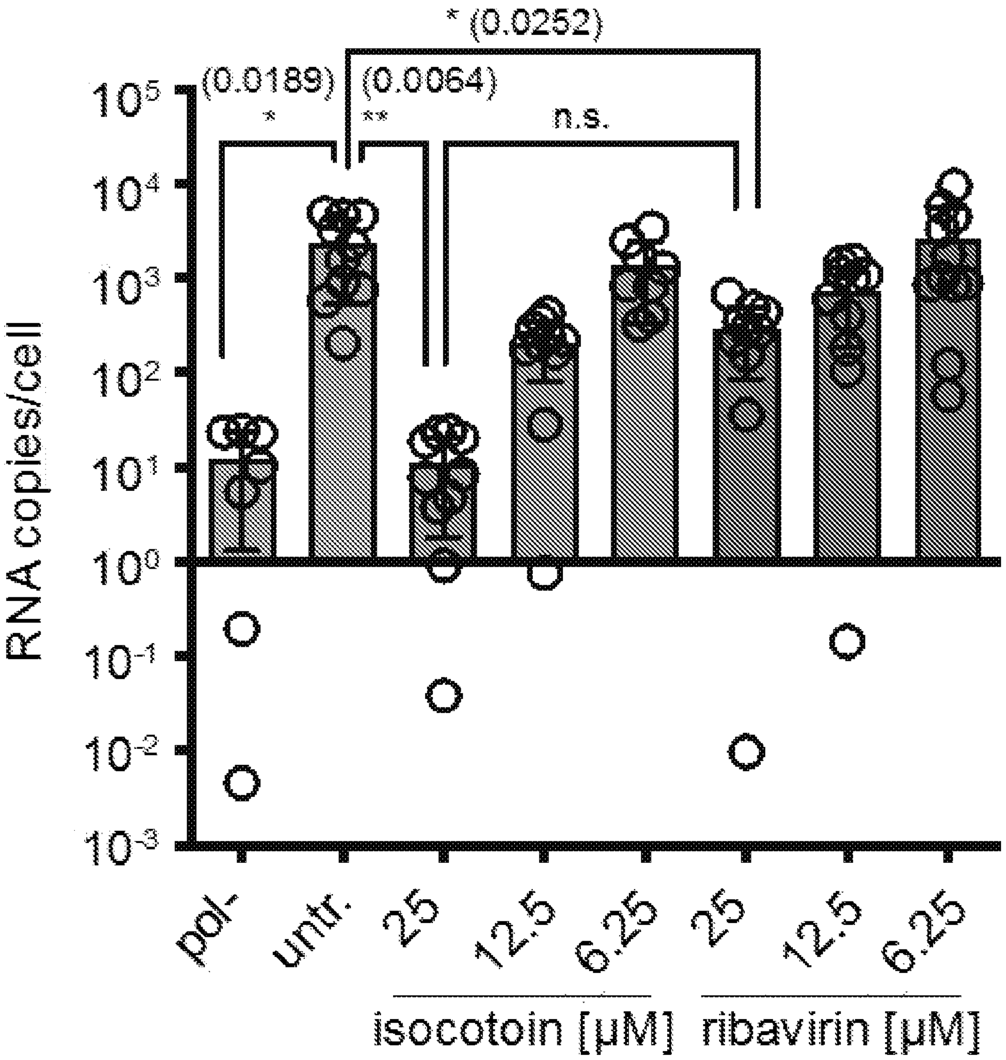

Through successive rounds of screening, isocotoin was identified as a promising therapeutic candidate against HEV (FIG. 4A). In vitro functional assays were performed using a secreted *Gaussia luciferase* (Gluc)-expressing HEV replicon derived from the KernowC1p6 HEV strain, abbreviated p6/Gluc (HEVΔORF2/3[Gluc]) (FIG. 4B), and supernatant Gluc levels were measured as a proxy for viral replication[20]. Dose titration assays, in which Huh7 hepatoma cells were transfected with p6/Gluc (HEVΔORF2/3 [Gluc]) in vitro transcribed RNA and treated with varying doses of ribavirin or isocotoin for 4 days, revealed that isocotoin exhibits an IC50 value of 6.1 μM as compared to 12.8 μM for ribavirin, the only currently available treatment for HEV infection in immunocompromised patients (FIG. 4C). RT-qPCR assays confirmed that isocotoin also inhibits the full-length KernowC1p6 in a dose-dependent manner (FIG. 4D).

Figure 4E:
Figure 4F:
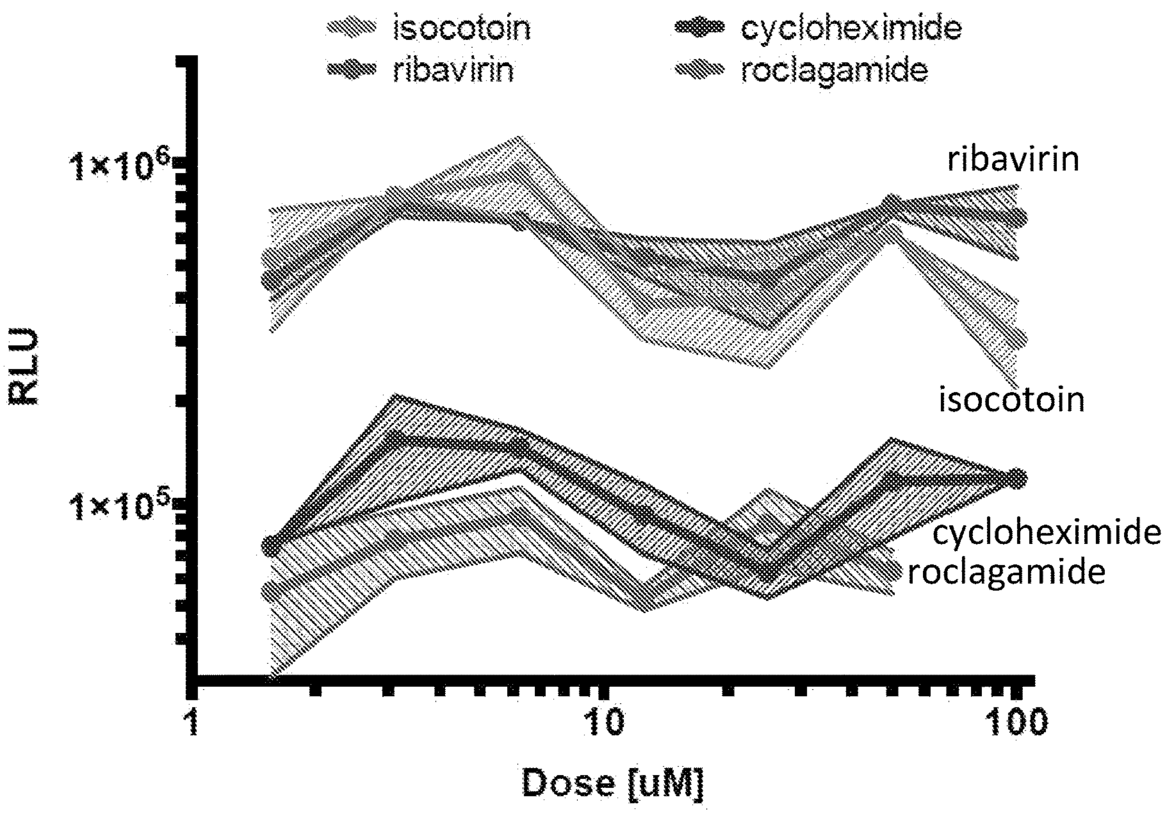

To test whether isocotoin was simply inhibiting generalized protein translation, a reporter construct was created. The reporter construct, T7-tagBFP-Gluc, contained Gluc and the fluorescent protein tagBFP, and could be in vitro-transcribed from a T7 promoter, but was devoid of any HEV-derived viral proteins (FIG. 4E). Capped tagBFP-Gluc RNA was transfected into cells that were then treated with varying doses of isocotoin for 4 days. Known translation inhibitors cycloheximide and roclagamide, an analogue of silvestrol[21], and ribavirin (RBV), which is a nucleoside analog that does not affect translation[22], were included as controls. The results indicated that whereas cycloheximide and roclagamide suppress Gluc levels ~10-fold, isocotoin did not lead to a significant decrease in Gluc levels as compared to ribavirin (FIG. 4F).

Figure 4G:
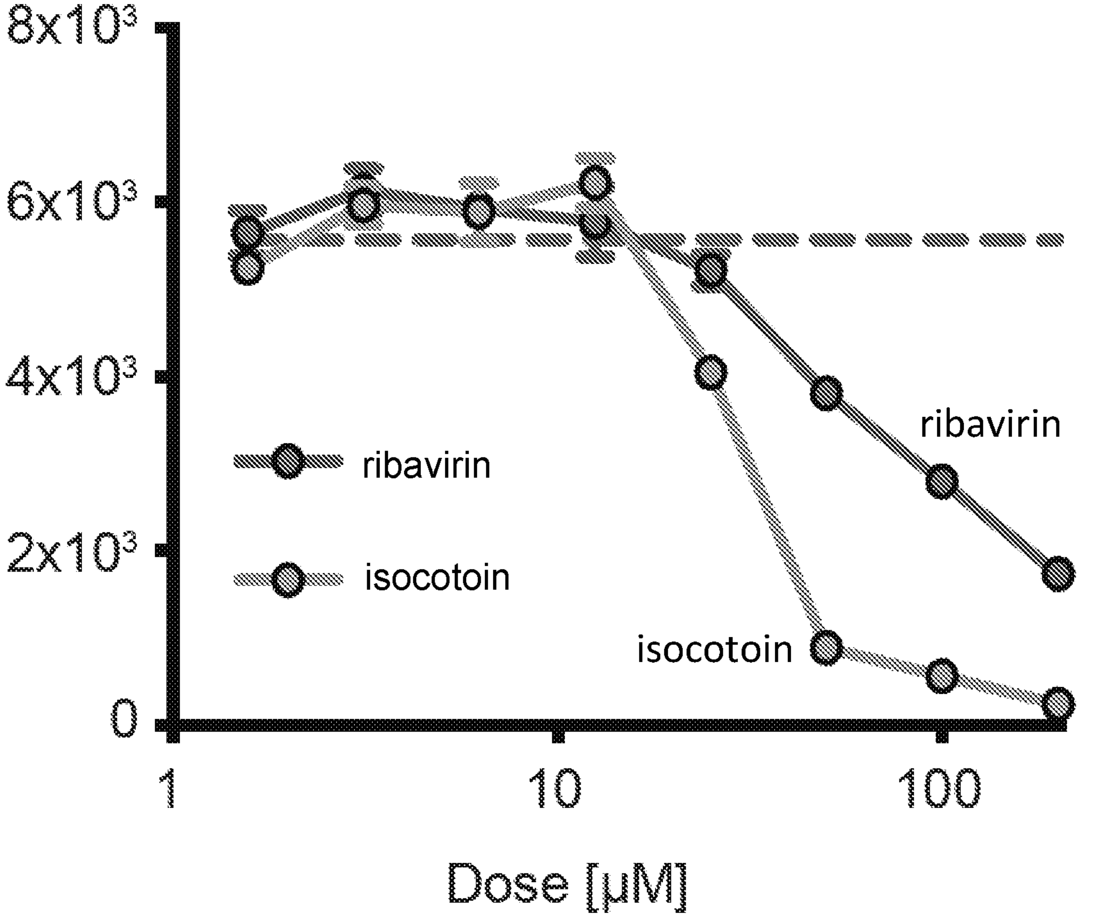

To ensure that cytotoxicity did not account for the observed reductions in replication, an ATP-based cell viability assay was performed on Huh7 cells after treatment with isocotoin or ribavirin. The results indicated that isocotoin displayed cytotoxicity at doses 25 μM and above, but not at doses up to 12.5 μM (FIG. 4G). Since isocotoin exhibits antiviral effects at doses lower than 12.5 μM (its $IC_{50}$ value is 6.1 μM), the antiviral effects at these lower doses cannot be attributed to cytotoxicity. Collectively, these data suggest that isocotoin specifically interferes with HEV replication in contrast with silvestrol, which was previously shown to inhibit HEV through general suppression of protein translation[21].

Testing Isocotoin Against Diverse HEV Genotypes

Figure 5A:
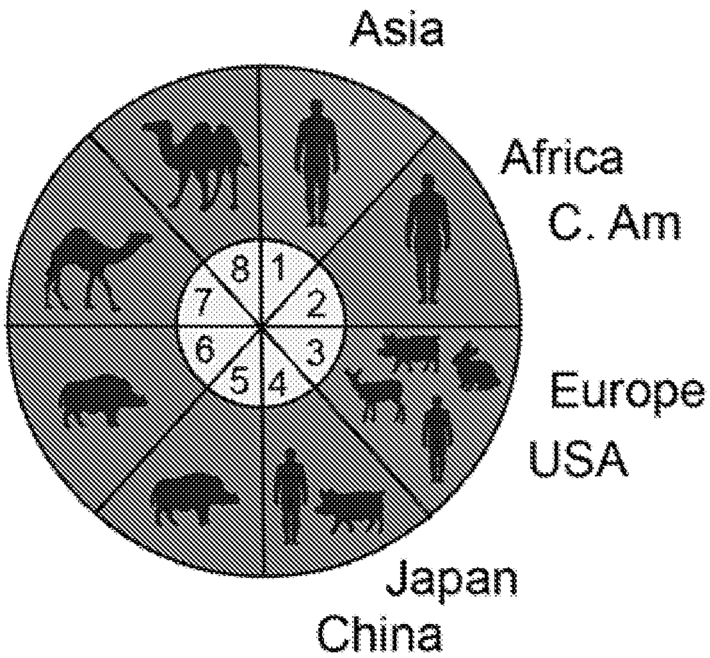
Figure 5B:
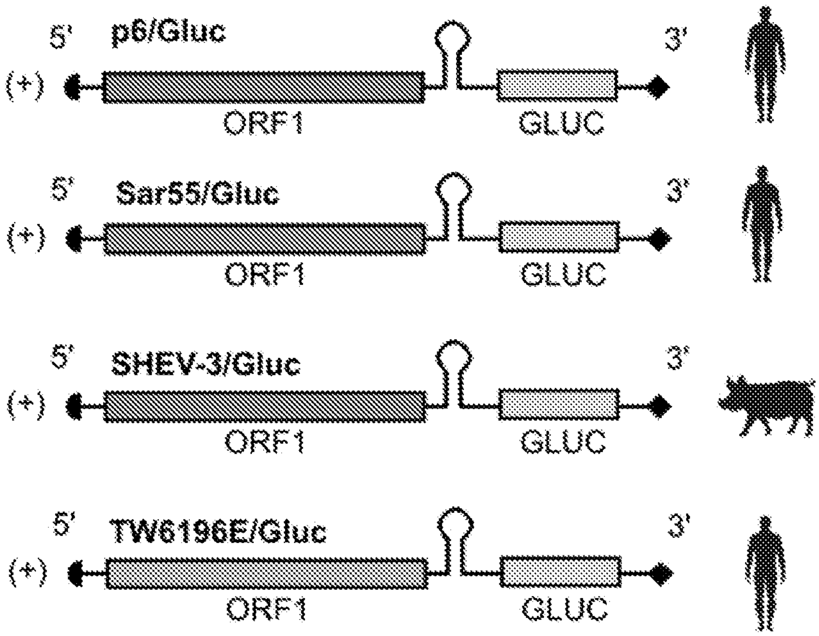
Figure 5D:
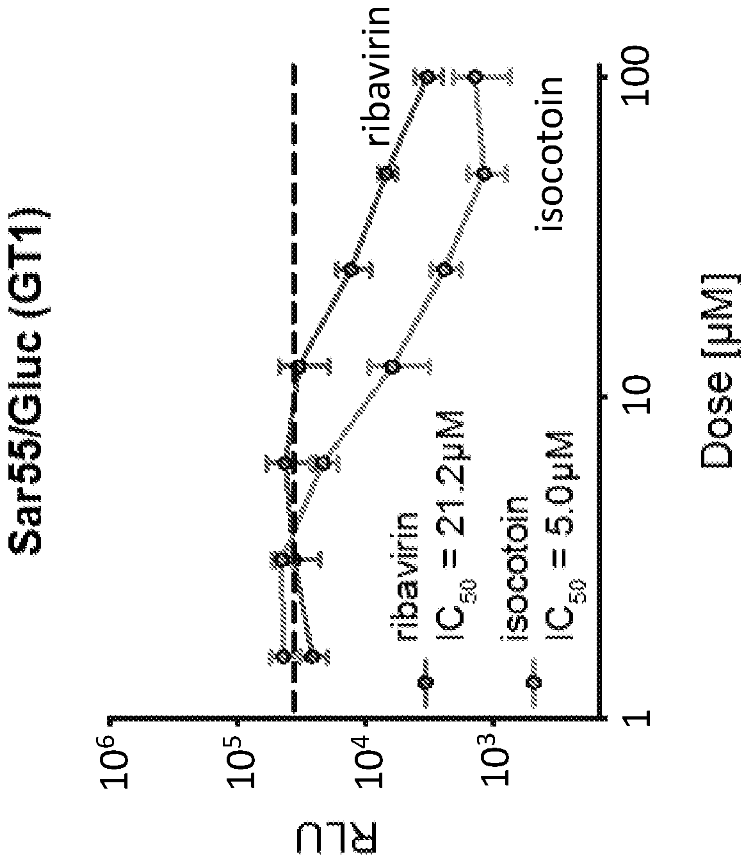
Figure 5C:
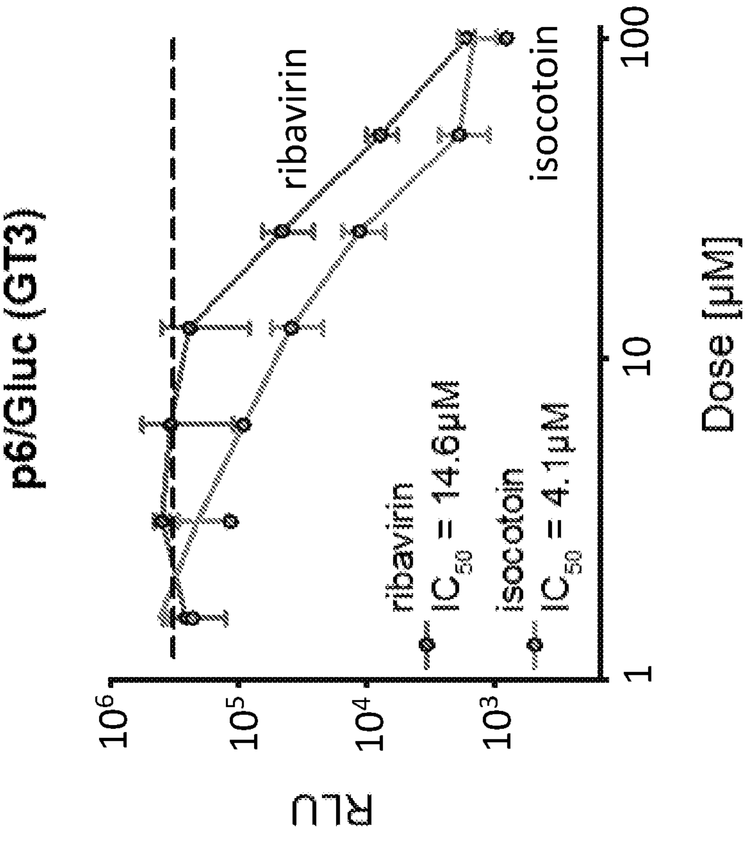
Figure 5F:
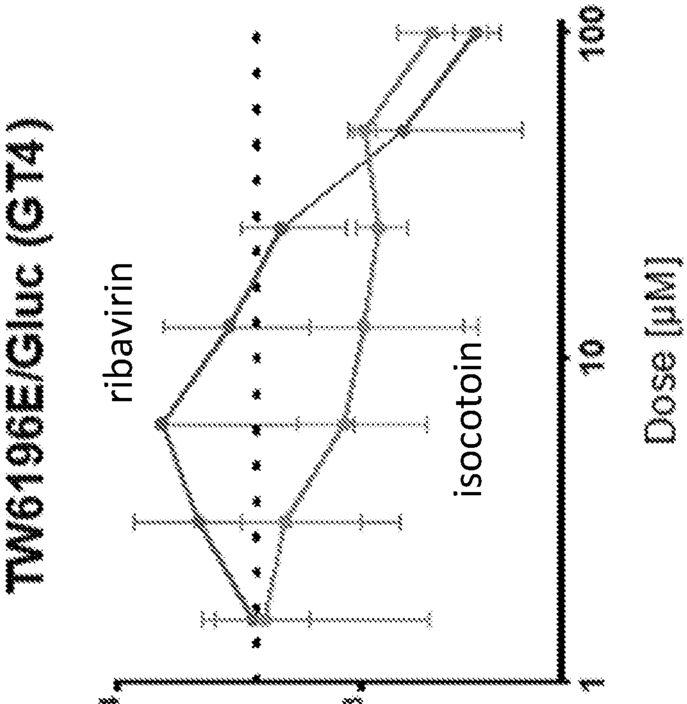
Figure 5E:
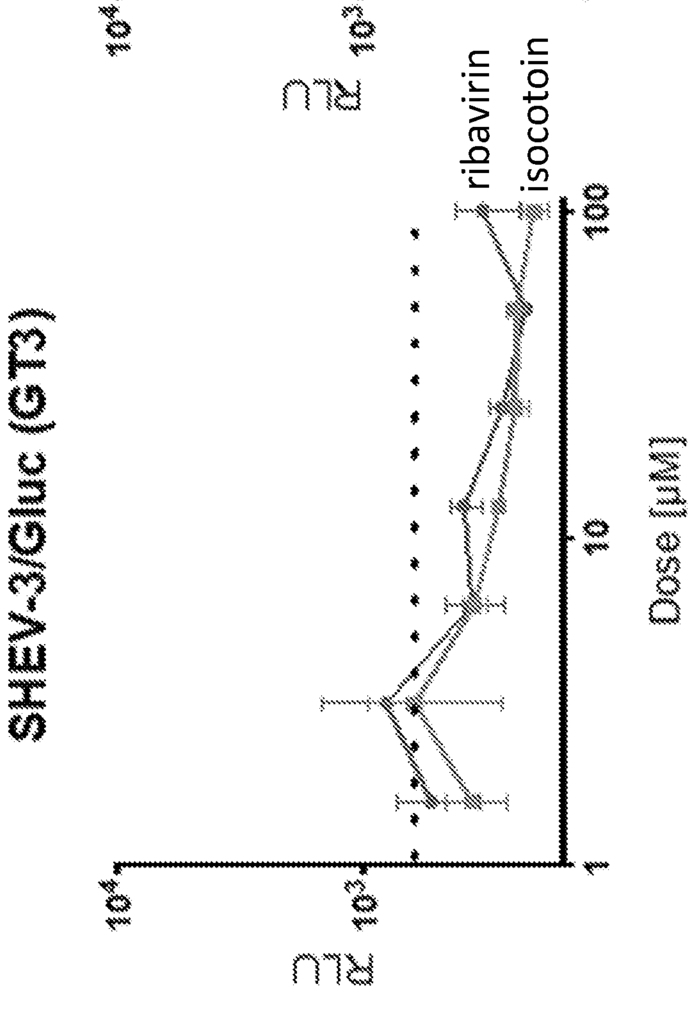

Next, it was determined whether isocotoin exhibited activity against genetically diverse HEV genotypes. At least eight genotypes of HEV (genotypes 1-8) have been identified in mammals, with genotypes 1-4 accounting for the majority of reported infections in humans (FIG. 5A)[23]. cDNAs are only currently available for genotypes 1, 3, and 4, and, very recently, 5. Of these, the KernowC1p6 (genotype 3) and Sar55 (genotype 1) strains are known to replicate robustly in cell culture systems, and are frequently used for in vitro studies. To evaluate its pan-genotypic antiviral efficacy, isocotoin was tested against Gluc-expressing replicons from the Sar55 (genotype 1), SHEV-3 (genotype 3, swine-derived), and TW6196E (genotype 4) HEV strains in addition to p6/Glue (KernowC1p6/Gluc) (named Sar55/Gluc, SHEV-3/Gluc, and TW6196E/Gluc, respectively) (FIG. 5B)[21]. Dose titration experiments against Sar55/Glue and p6/Glue (KernowC1p6/Gluc) demonstrated that isocotoin was effective against both strains and had a lower $IC_{50}$ than ribavirin (FIGS. 5C, 5D, 5G). For SHEV-3 and TW6196E, replicative capacity in cell culture is much lower, but a modest inhibitory effect was observed with isocotoin (these assays display large error due to poor replicative capacity) (FIGS. 5E, 5F).

Testing Isocotoin Against Other Positive-Sense RNA Viruses

Figure 6A:
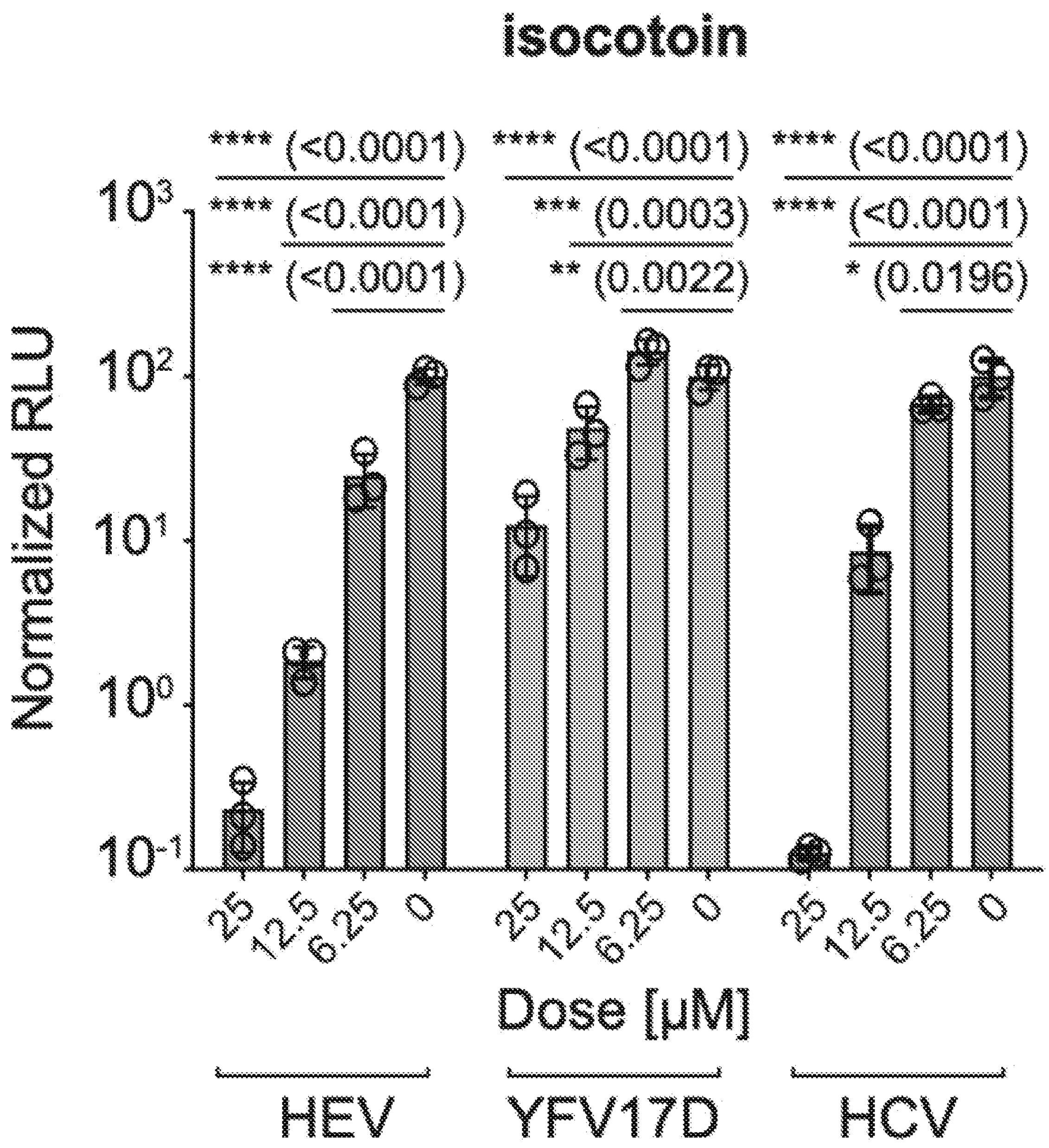
FIGS. 6A-6D. Isocotoin inhibits replication of other (+)-sense RNA viruses.
Figure 6B:
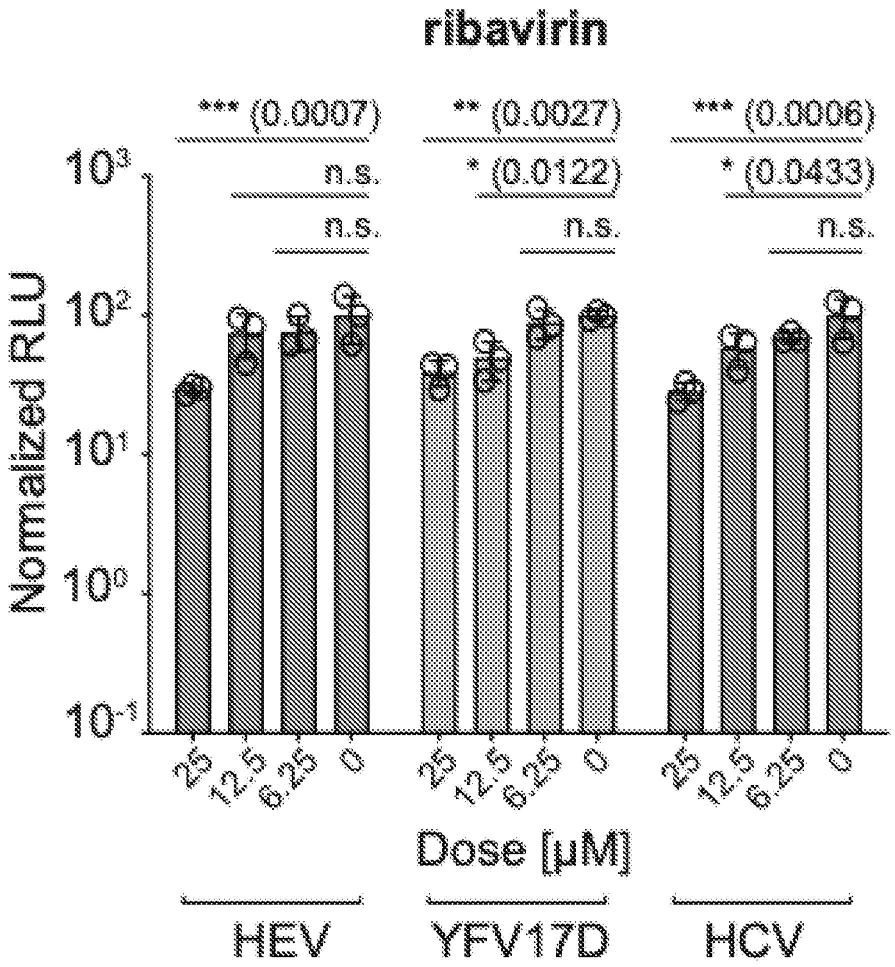
Figure 6C:
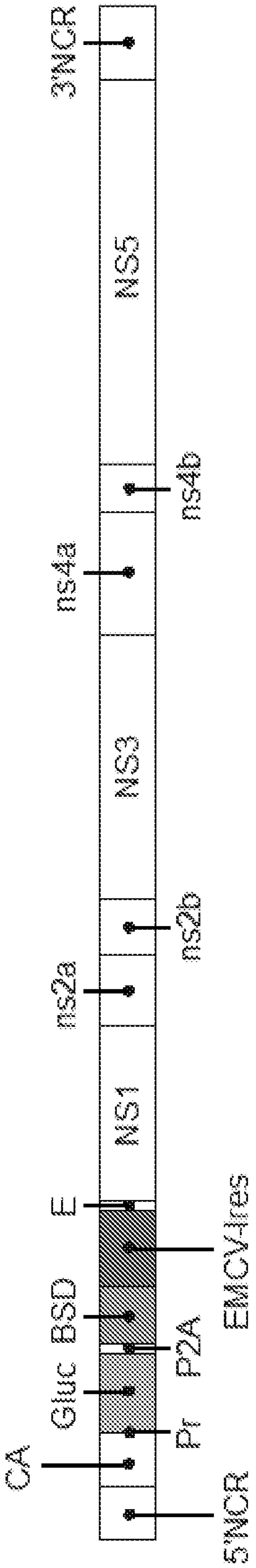
Figure 6D:
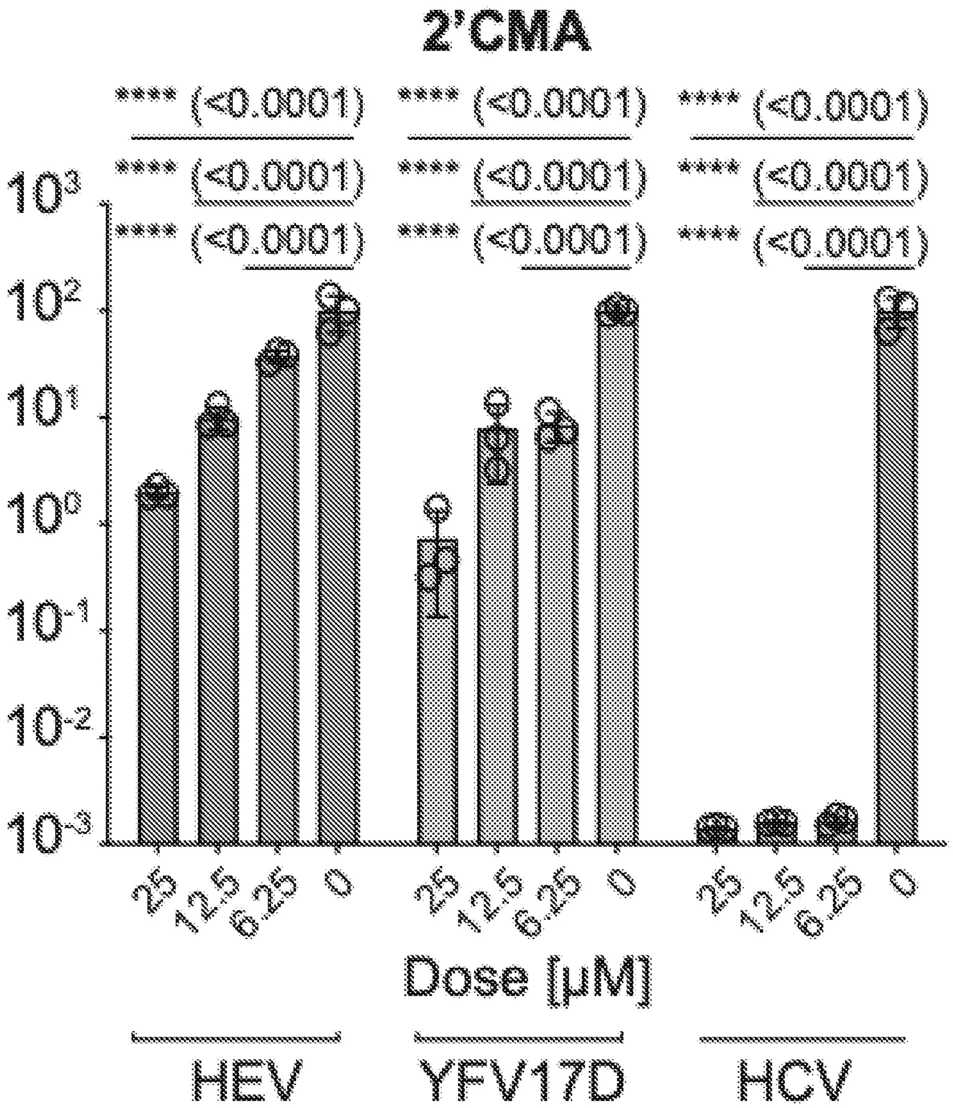

To examine whether the antiviral properties of isocotoin were specific to HEV or broadly effective against other viruses, isocotoin was tested against other positive-sense, single-stranded RNA viruses, including Glue-expressing genomes from hepatitis C virus (Jc1(p7nsGluc2A), abbreviated 'HCV') and yellow fever virus 17-D vaccine strain (YFV17D-Gluc-BSD-Ires, abbreviated 'YFV17D')[24] (FIGS. 6A, 6C, 6D). Ribavirin, a drug that used to be the standard of care for treating HCV and is still commonly used for treating HEV, and 2'-C-methyladenosine, a specific inhibitor of the HCV NS5B protein, were used as controls (FIG. 6B). While RBV had only minor inhibitory effects on any of the viruses under the experimental conditions used here, isocotoin showed dose-dependent inhibitory effects against all three viruses. Collectively, these data suggest that isocotoin operates through a common inhibitory mechanism against all three viruses tested.

Suboptimal Dosing Experiments to Identify Adaptive Mutations

Figure 7A:
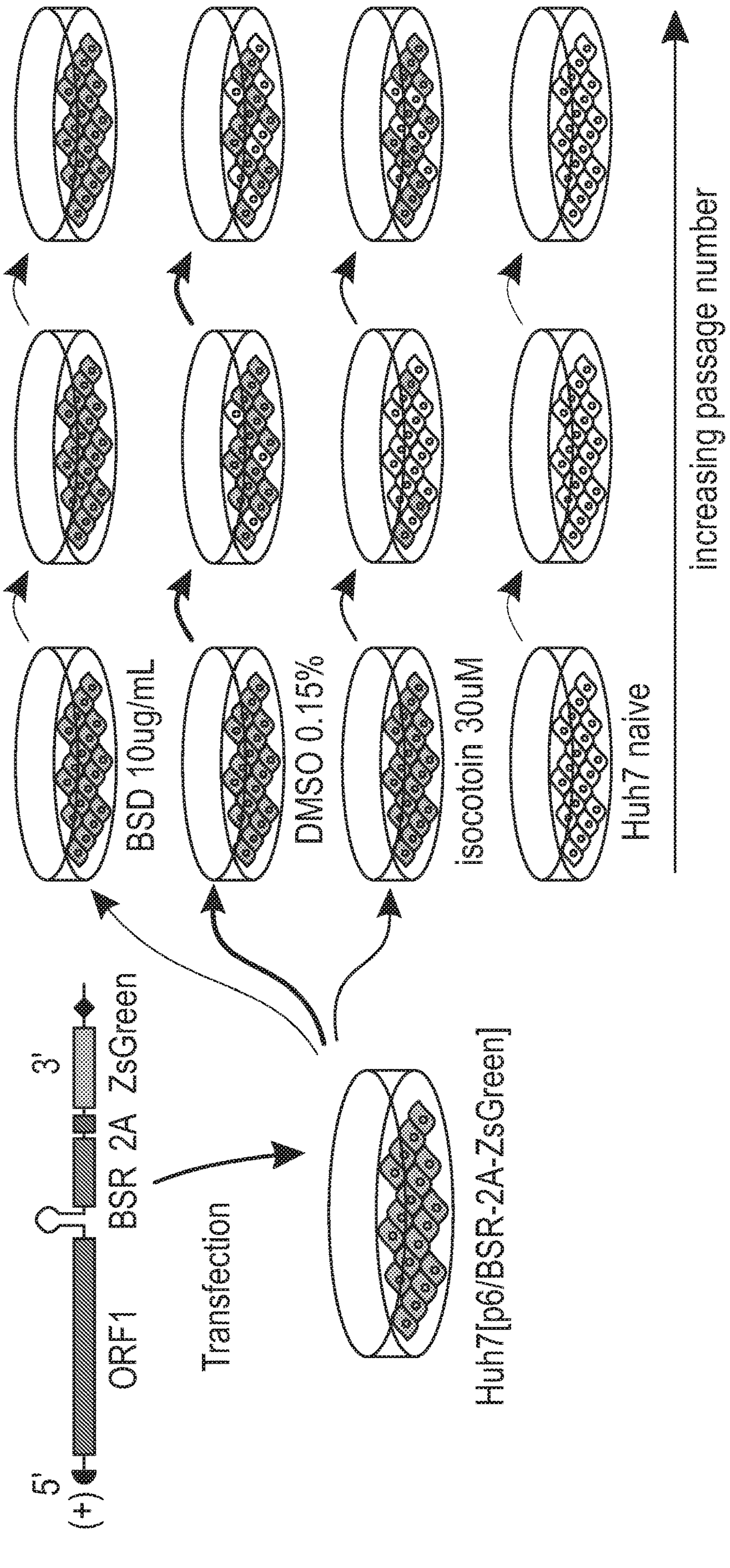
FIGS. 7A-7G. Isocotoin inhibits strains exhibiting higher replicative capacity in vitro.

To determine isocotoin's mechanism of action, suboptimal dosing experiments were performed in which HEV was passaged in the presence of sublethal doses of isocotoin for a prolonged time. The virus was expected to evolve resistance mutations to isocotoin that could be sequenced and used to identify the drug's target (FIG. 7A). For these experiments, a replicon genome derived from KernowC1p6, in which ORFs 2 and 3 were replaced with a blasticidin resistance-conferring gene (BSR) and a ZsGreen fluorescence reporter, abbreviated p6/BSR-2A-ZsGreen (FIG. 7A), was used. Cells transfected with p6/BSR-2A-ZsGreen were maintained in 30 μM isocotoin, 10 μg/mL blasticidin, or 0.15% DMSO (concentration of vehicle for isocotoin), and fluorescence levels were measured at each passage with flow cytometry. Though some toxicity was observed at the 30 μM isocotoin dose, cells were still able to grow at a reduced rate and recover from repeated passaging. Naïve Huh7 cells were included as a negative control for fluorescence.

Figure 7B:
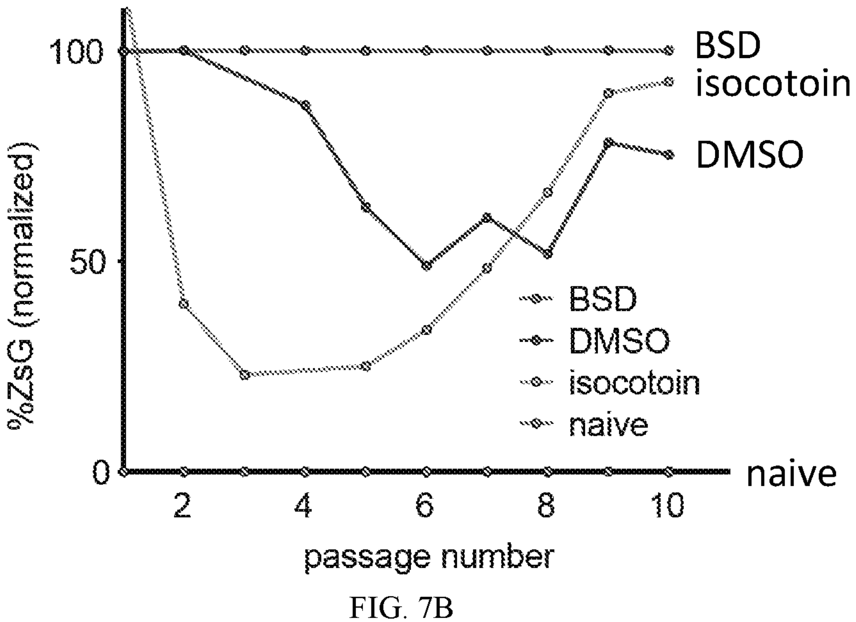

Isocotoin treatment led to a sharp decrease in ZsGreen levels during the first few passages, with a subsequent increase in ZsGreen levels starting at passage 6 (FIG. 7B). By passage 9, ZsGreen levels approached the levels seen in the positive control (cells under selection with blasticidin) (FIG. 7B). Intracellular RNA was extracted from both passage 1 and passage 10 cell lysates and reverse transcribed to produce cDNA. Overlapping segments covering ORF1 were PCR-amplified, sequenced, and aligned to identify any regions that had mutated from passage 1 to passage 10.

Figure 7C:
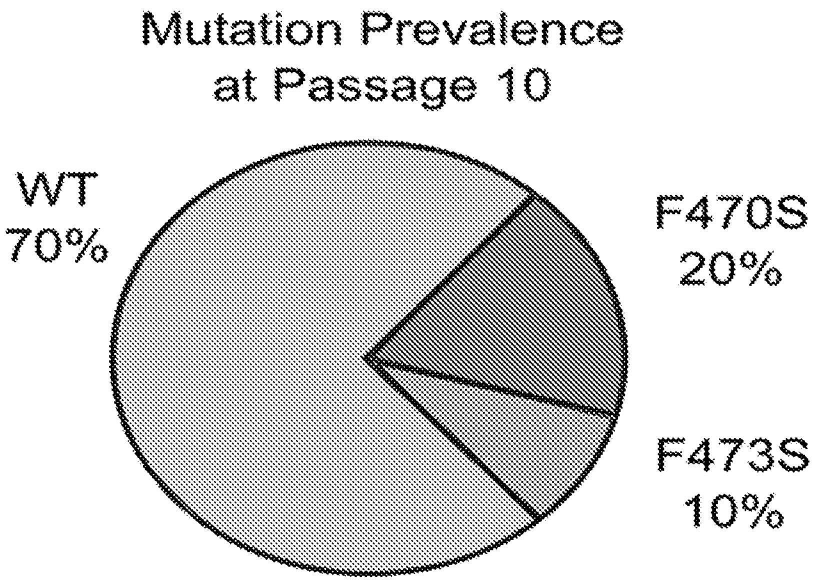

Although no dominant mutation was found, a highly conserved palindromic 'FCCF' peptide sequence located at residues 470-473 in the putative cysteine protease region was found to contain a phenylalanine to serine point mutation in 30% of the clones (FIG. 7C). The F470S and F473S single point mutations were inserted into the wild-type p6/Gluc replicon (HEVΔORF2/3[Gluc] genome), and it was observed that p6/Gluc[F470S] (HEVΔORF2/3[Gluc][F470S]) exhibited a higher replicative capacity in vitro than either the wild-type p6/Gluc strain (parental HEVΔORF2/3[Gluc]) or the p6/Gluc[F473S] (HEVΔORF2/3[Gluc][F473S]) strain, which was replication-inhibited (data not shown). These data suggested that the emergence of the F470S point mutation in passage 10 cells may have been due to the enhanced replicative capacity of this strain, and not isocotoin resistance.

Isocotoin Exhibits Inhibitory Activity Against HEV Strains Harboring Mutations Associated with Clinical Resistance to Ribavirin.

Figure 7D:
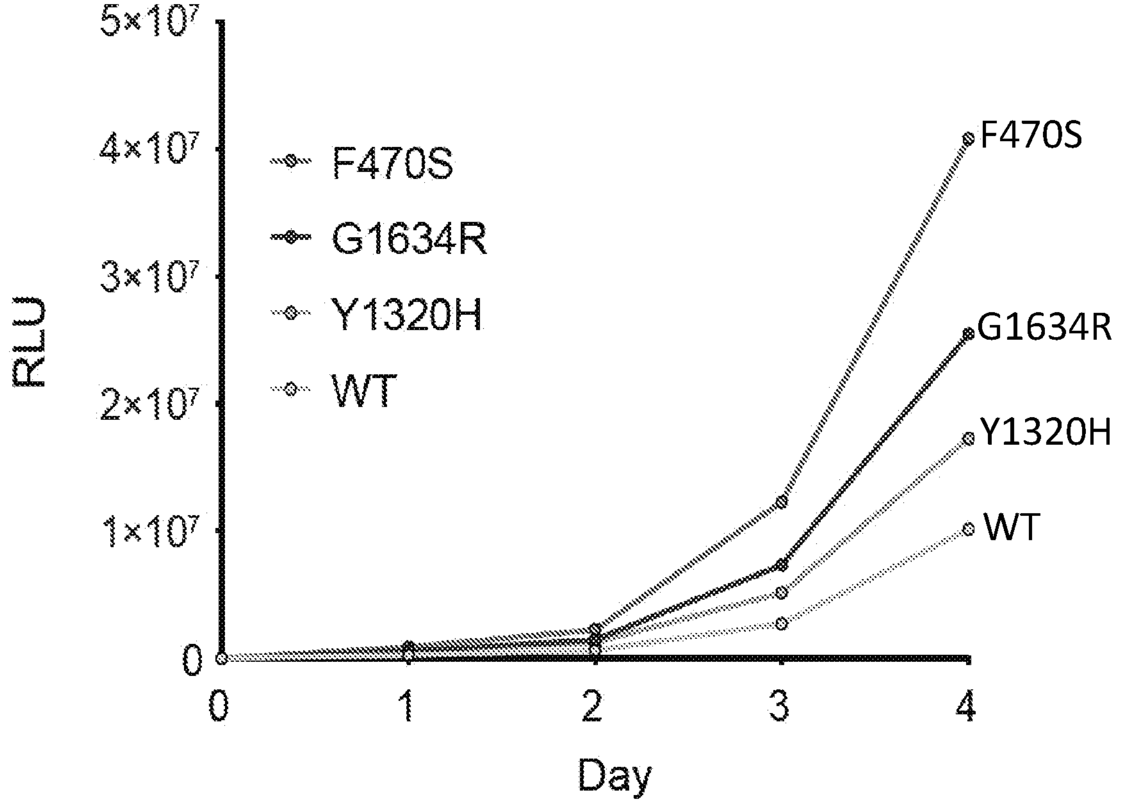
Figure 7E:
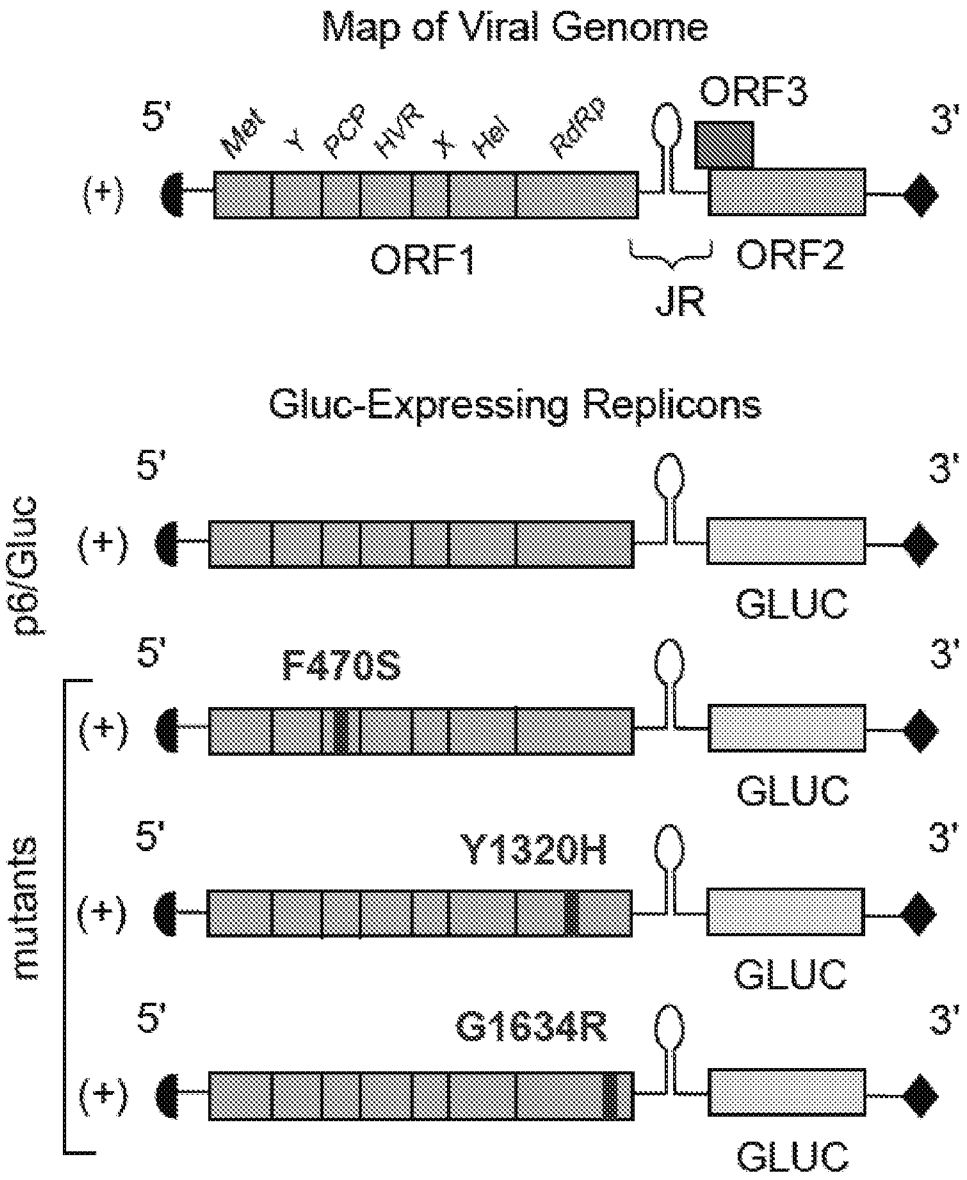
Figure 7F:
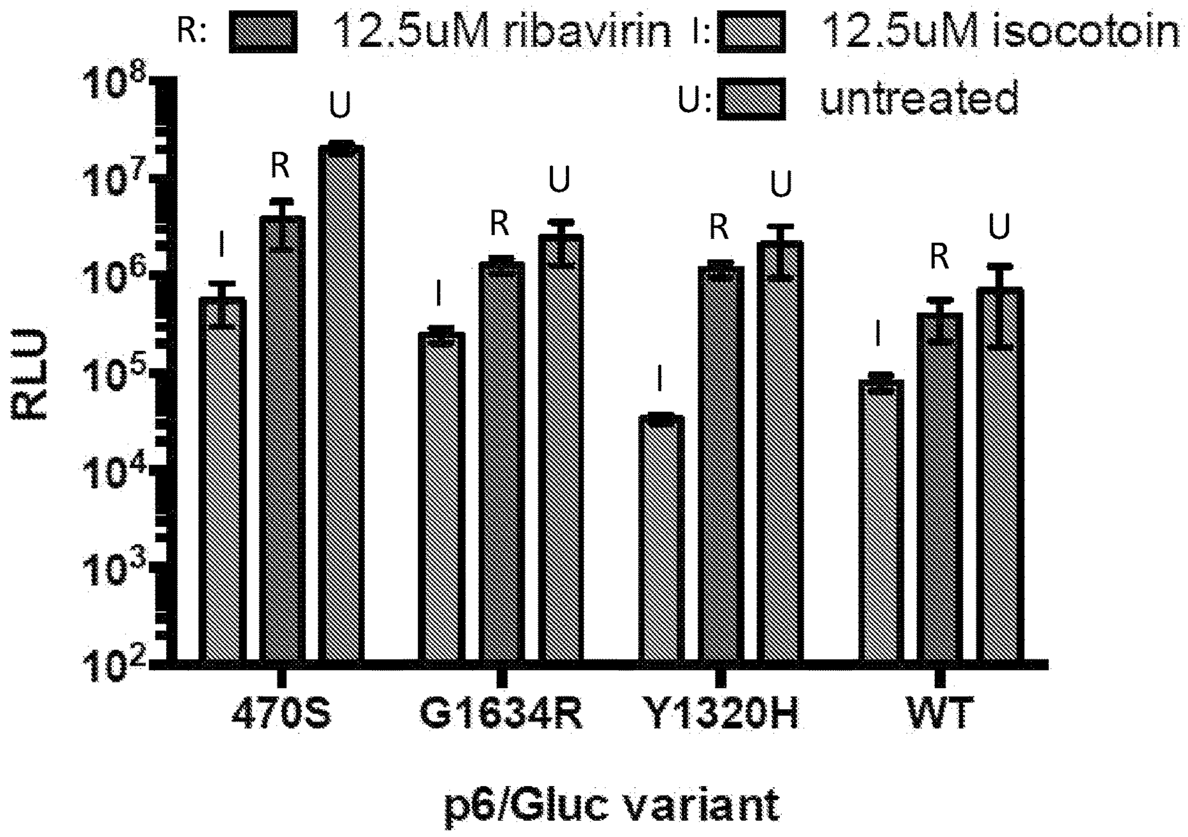
Figure 7G:
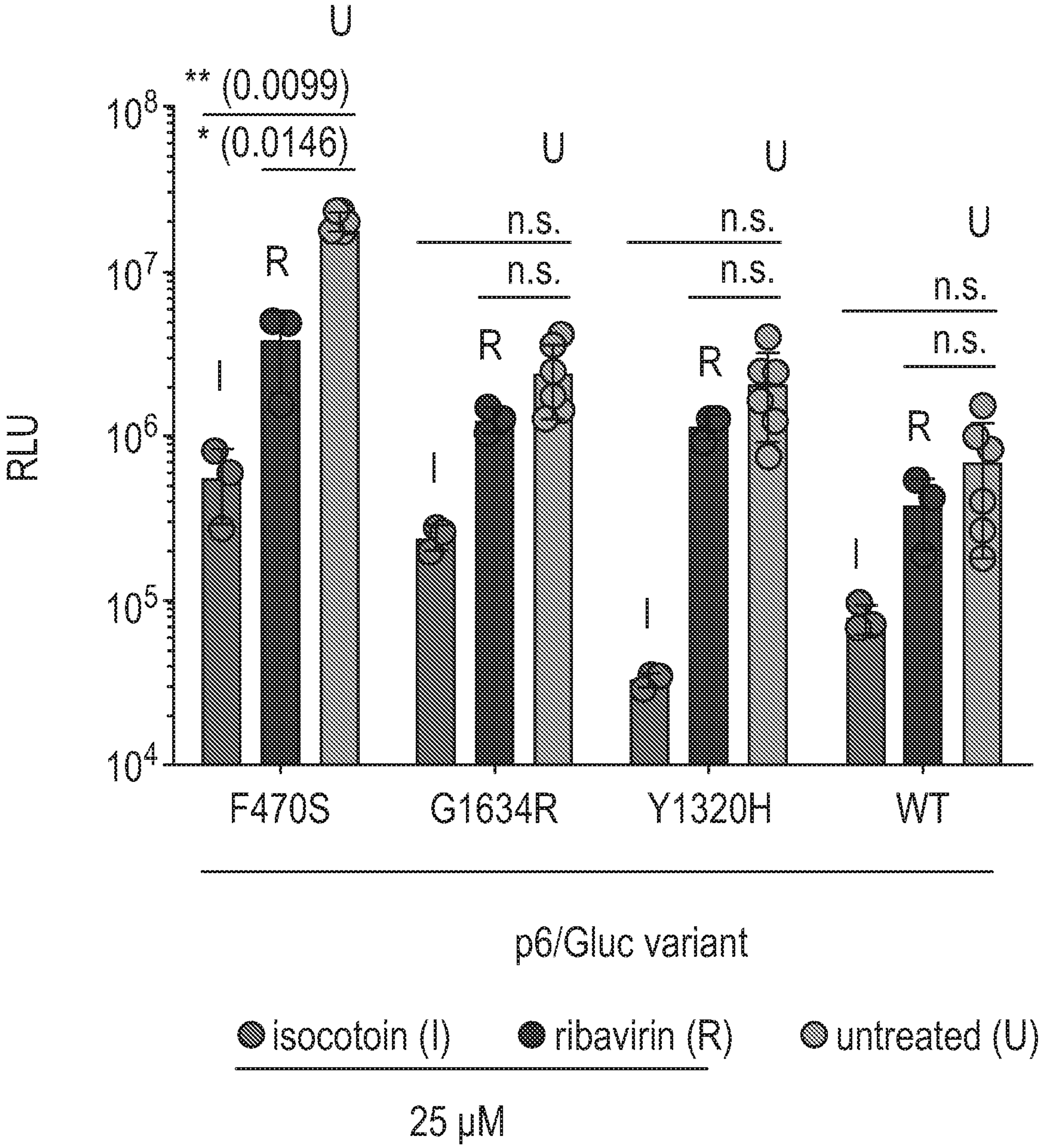

Emergence of ribavirin-resistant strain poses a significant problem for the treatment of hepatitis E. Previous studies characterizing clinically ribavirin-resistant strains in vitro had identified that G1634R and Y1320H point mutations in the RdRp region of ORF1 similarly led to enhanced replicative capacity in vitro[9, 25]. p6/Gluc[Y1320H] (HEVΔORF2/3[Gluc][Y1320H]) and p6/Gluc[G1634R] (HEVΔORF2/3[Gluc][G1634R]) mutant replicons were generated to compare their replicative capacities to that of the newly identified p6/Gluc[F470S] (HEVΔORF2/3[Gluc][F470S]) (FIG. 7E). Measurement of supernatant Gluc over 4 days post-transfection in Huh7 cells revealed that p6/Gluc[F470S](HEVΔORF2/3[Gluc][F470S]) exhibited a higher replicative capacity than both p6/Gluc[Y1320H] (HEVΔORF2/3[Gluc][Y1320H]) and p6/Gluc[G1634R] (HEVΔORF2/3[Gluc][G1634R]) (FIG. 7D). These results suggest that the F470S mutation could potentially lead to clinical ribavirin resistance through a similar mechanism as the previously identified mutant strains. All three higher-replicating strains exhibited a higher sensitivity to isocotoin than to ribavirin (FIGS. 7F, 7G).

Structure Activity Relationship Analysis Reveals Compounds Structurally Analogous to Isocotoin with Higher Potency Against HEV Replication To identify the specific functional groups within isocotoin mediating its biological activity, two rounds of structure-activity relationship (SAR) analysis were performed in which structural analogs to isocotoin were evaluated for efficacy against p6/Gluc. In these experiments, dose titration assays were performed against Huh7 cells transfected with p6/Gluc in vitro transcribed RNA. In the first round of SAR, a chemical space was identified that led to greater inhibition of HEV replication than the parent compound isocotoin (Appendices 1, 1'). In the second round of SAR, a set of compounds were chosen that explored further modifications within this chemical space that could further improve potency (Appendices 2, 2').

Figure 8A:
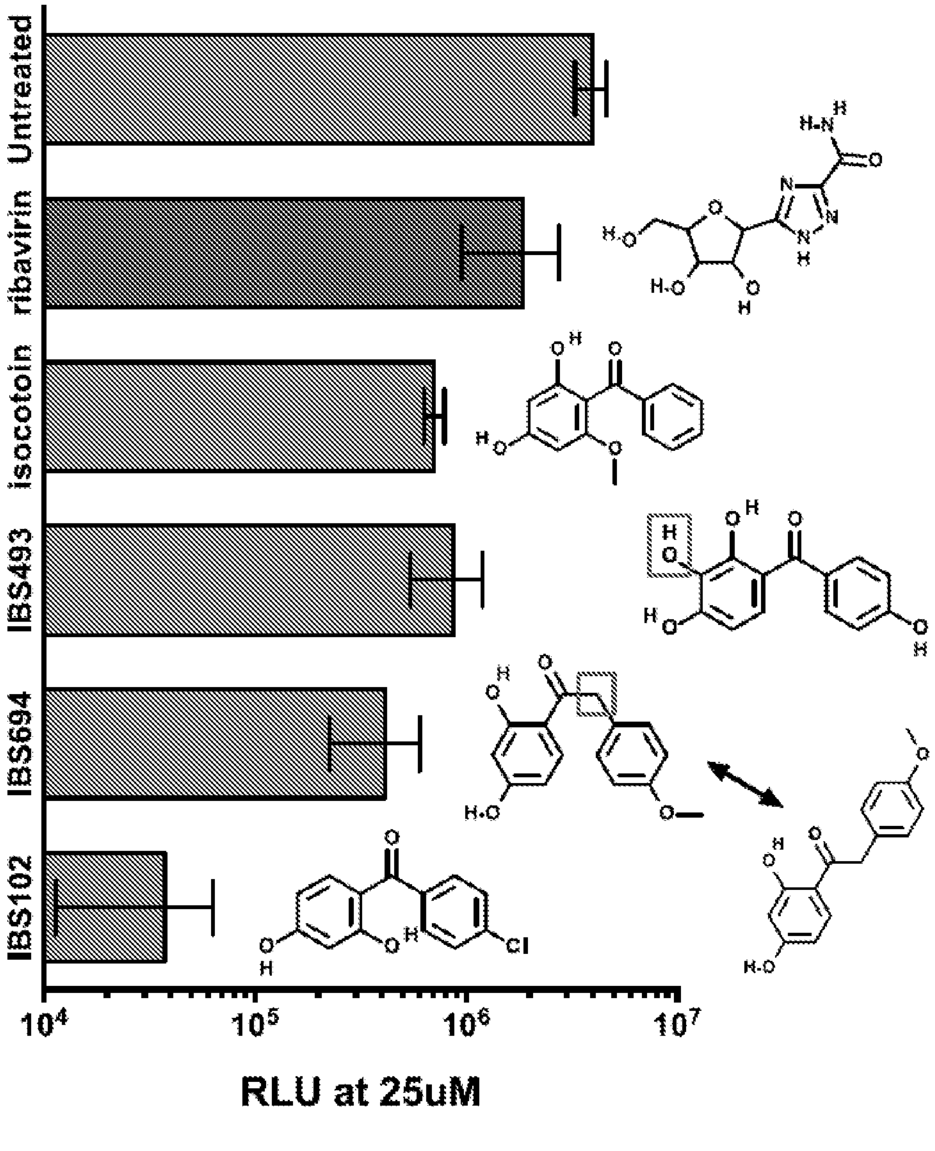
FIGS. 8A-8B. Structure-activity relationship (SAR) analysis is used to correlate functional groups with biological activity and identify compounds exhibiting higher potency against p6/Gluc.
Figure 8B:
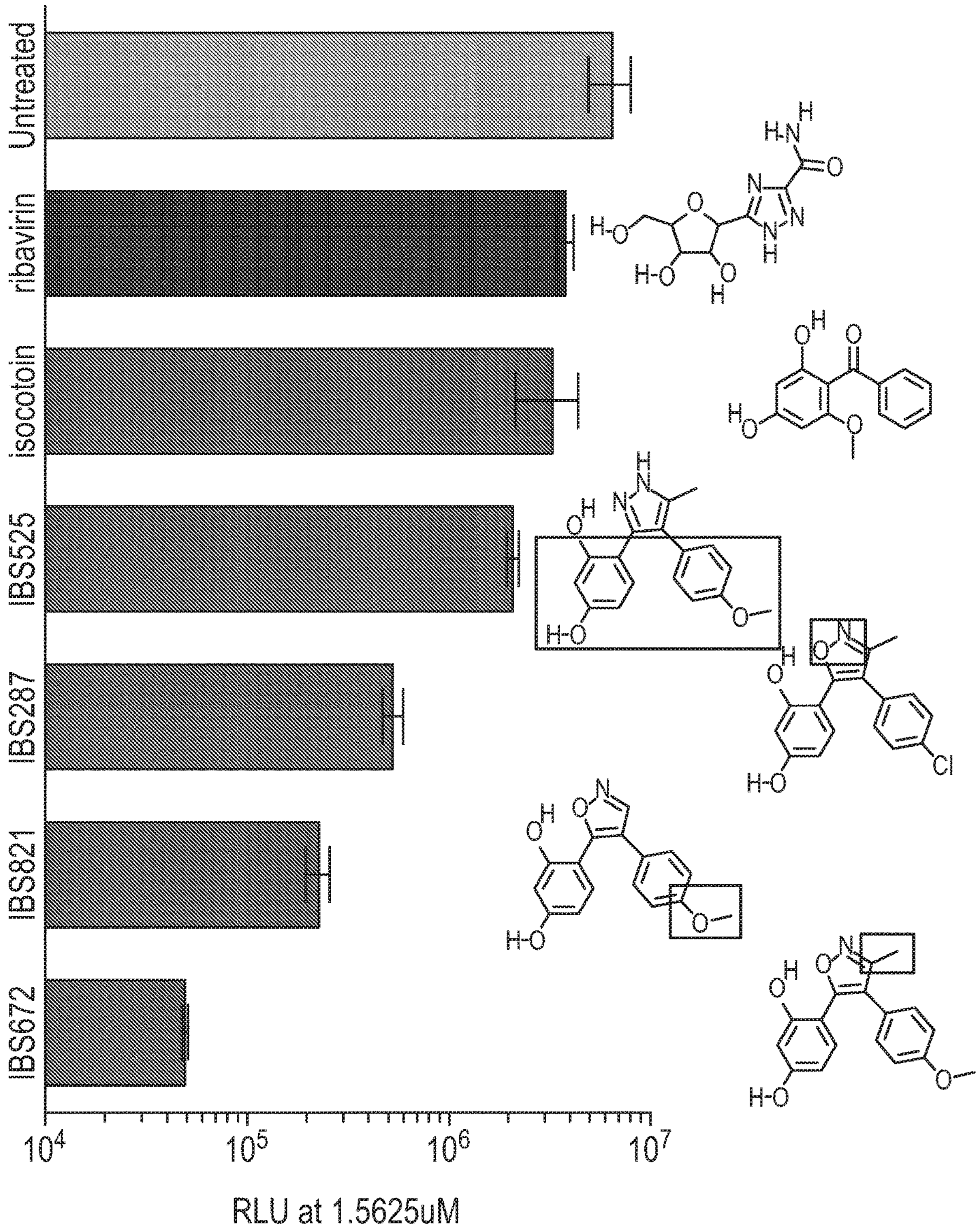
Figure 9:
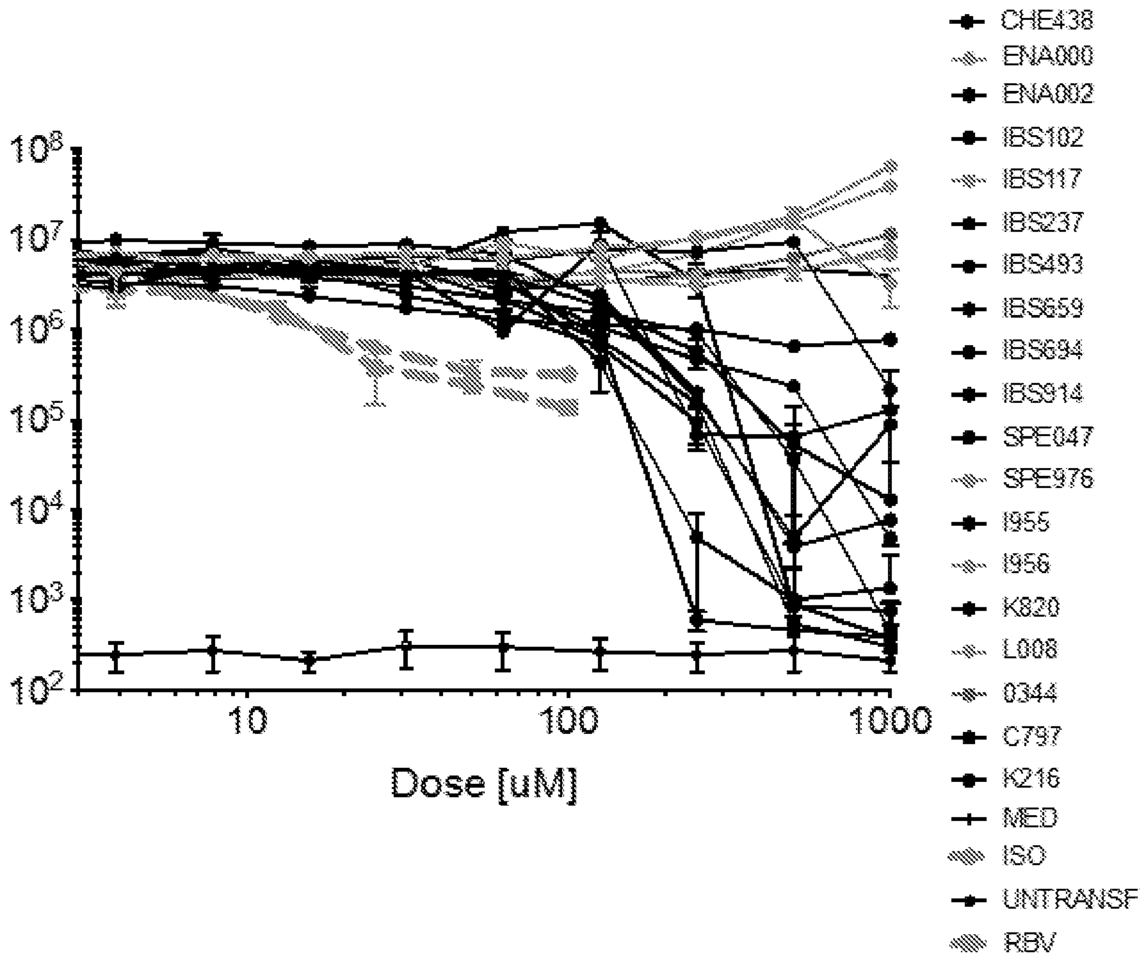
FIG. 9. Structure-activity relationship (SAR) analysis Round 1. A subset of structurally related compounds to isocotoin showed greater inhibition of p6/Gluc. Another subset showed no effect, and finally one subset is associated with a slight increase in replication levels. RLU=relative light units. Error bars indicate 1 SD from mean.
Figure 10A:
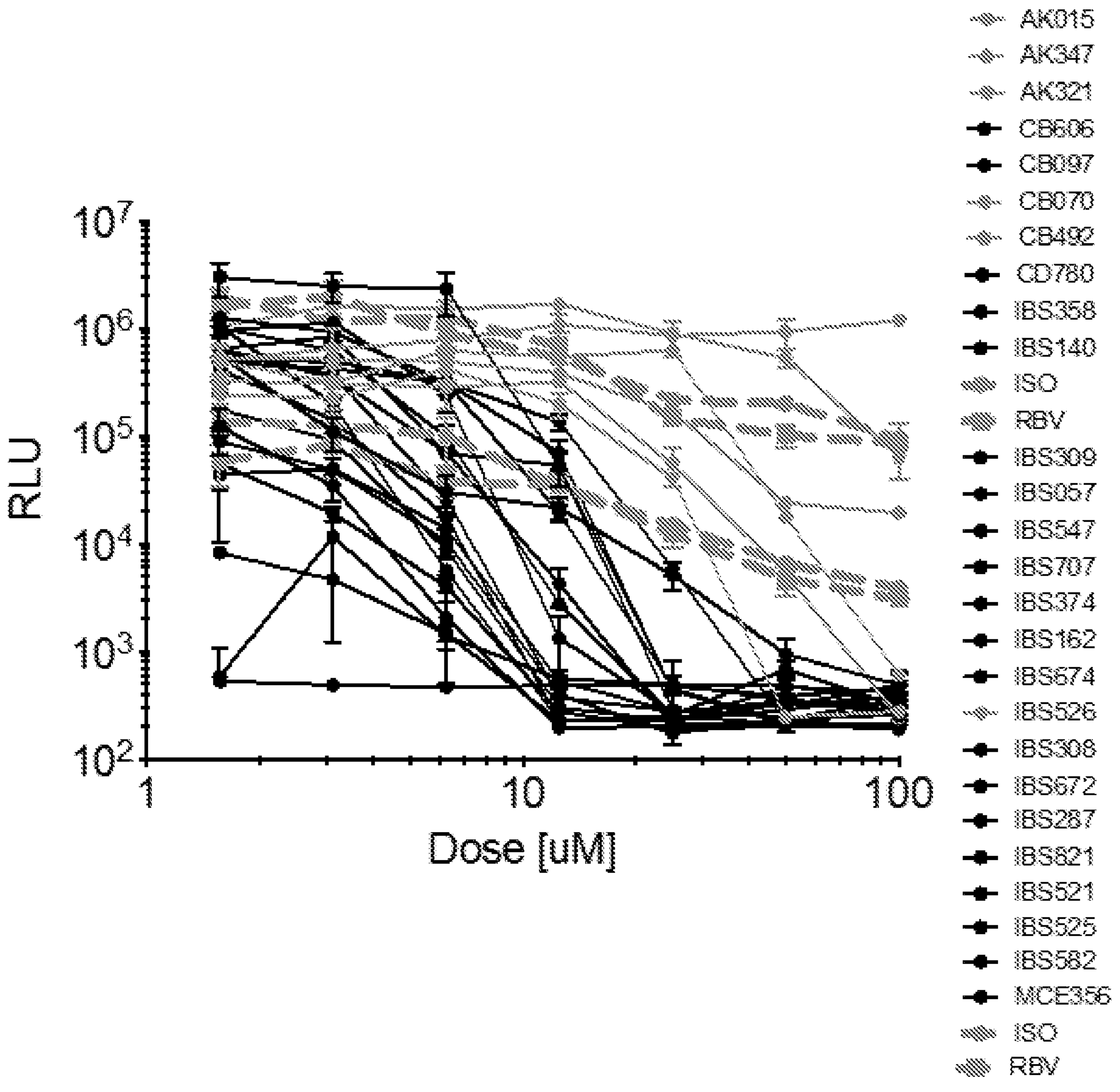
FIGS. 10A-10B. SAR analysis Round 2.
Figure 10B:
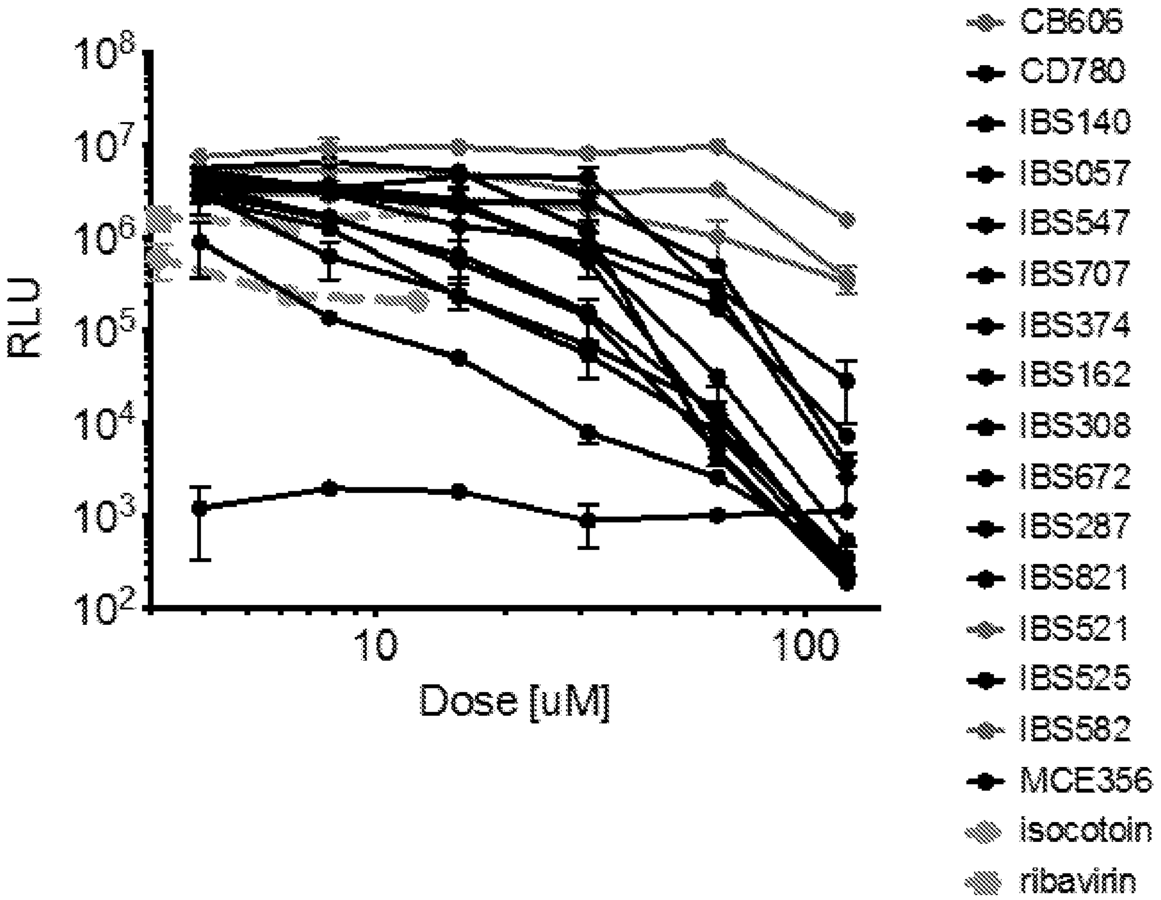

During the first round of SAR analysis, a compound was identified—IBS102—that led to an approximately 10-fold greater decrease in RLU than isocotoin at the 25 μM dose (FIG. 8A). During the second round of SAR analysis, the compound IBS672 was found to lead to an approximately 40-fold greater decrease in RLU than isocotoin at 1.5625 μM (FIG. 8B).

Isocotoin Directly Binds Heat Shock Protein 90 (HSP90)

Figure 11A:
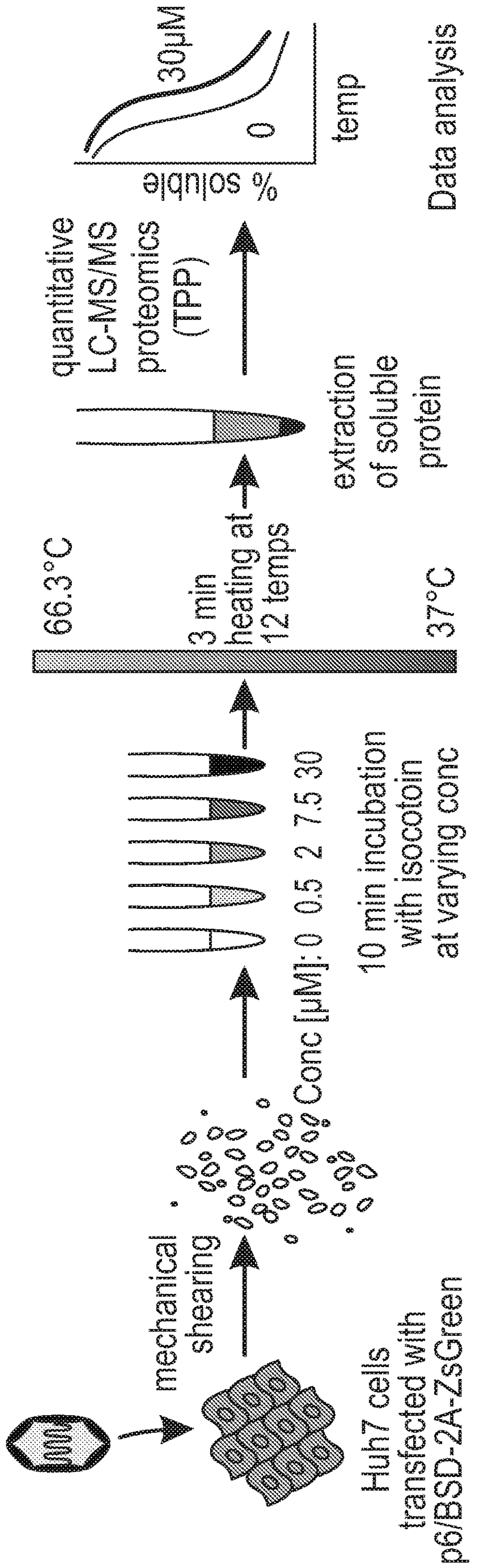
FIGS. 11A-11G. Isocotoin inhibits HEV replication through interference with HSP90.

Thermal proteome profiling was performed to identify direct binding targets of isocotoin (FIG. 11A). Briefly, this assay identifies proteins whose stability changes in the presence of the drug due to binding interactions with the drug.

Figure 11B:
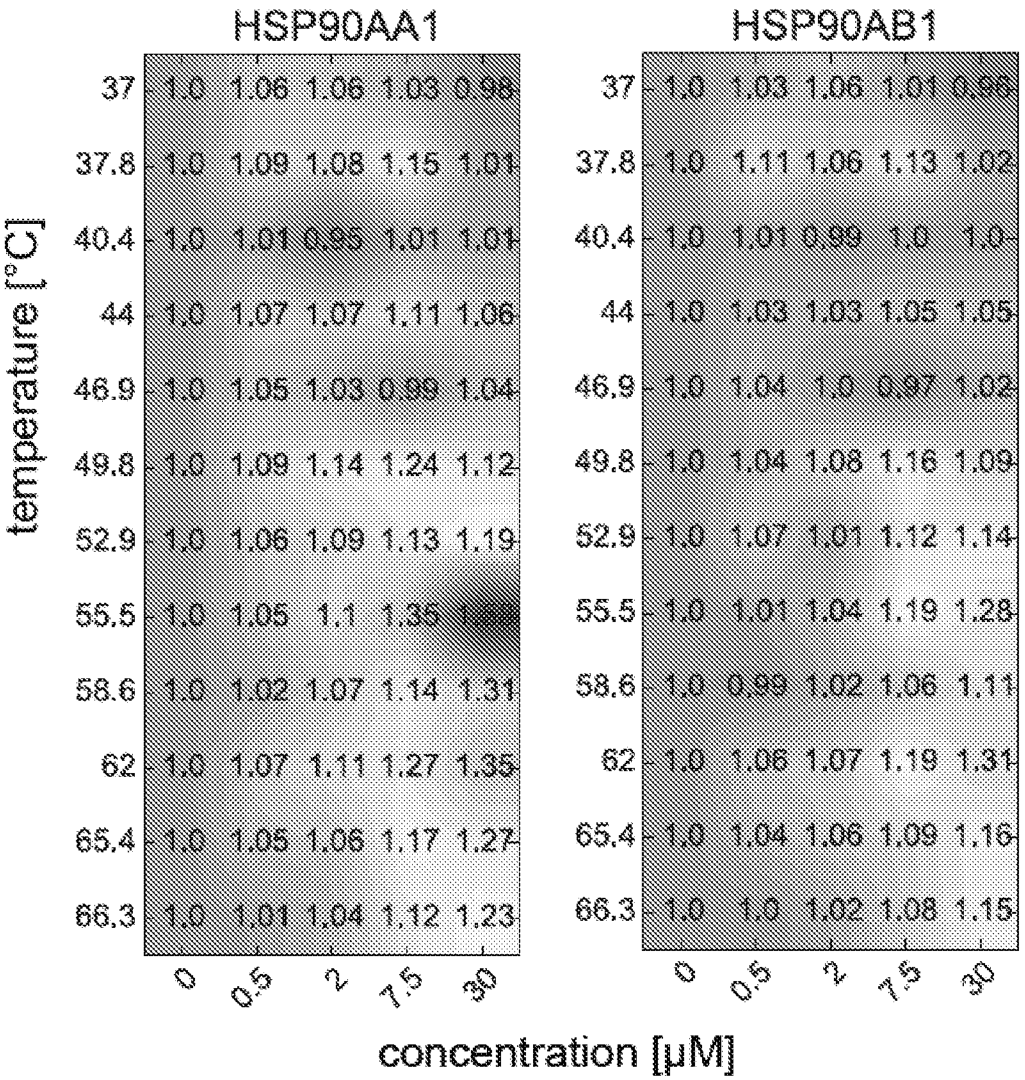

Thirty-one targets were identified exhibiting thermal stabilization in the presence of isocotoin. The hits included Hsp90α1 and Hsp90β, two Hsp90 isoforms known to play broad pro-viral roles (FIG. 11B)[26]. HSP90 are a family of conserved, abundant, and constitutively expressed molecular chaperones assisting in the maturation and localization of hundreds of cellular proteins. A diverse array of viruses, including herpes simplex viruses, simian virus 40, and HCV, rely on Hsp90 for critical functions including virus internalization, localization, and complex assembly[28-31]. Furthermore, many viruses are hyper-dependent on Hsp90 function, such that Hsp90 inhibition disproportionately impairs the viral life cycle as compared to regular host functions[26]. Hsp90 is thought to bind the HEV capsid protein for intracellular trafficking of the virus during the early stages of infection. However, since the assay described herein employed a reporter genome lacking the capsid protein gene (ORF2), it was hypothesized that Hsp90 may play an additional, yet uncharacterized role specific to HEV genomic replication[32].

Hsp90 is an Essential Host Factor for HEV Replication

Figure 11C:
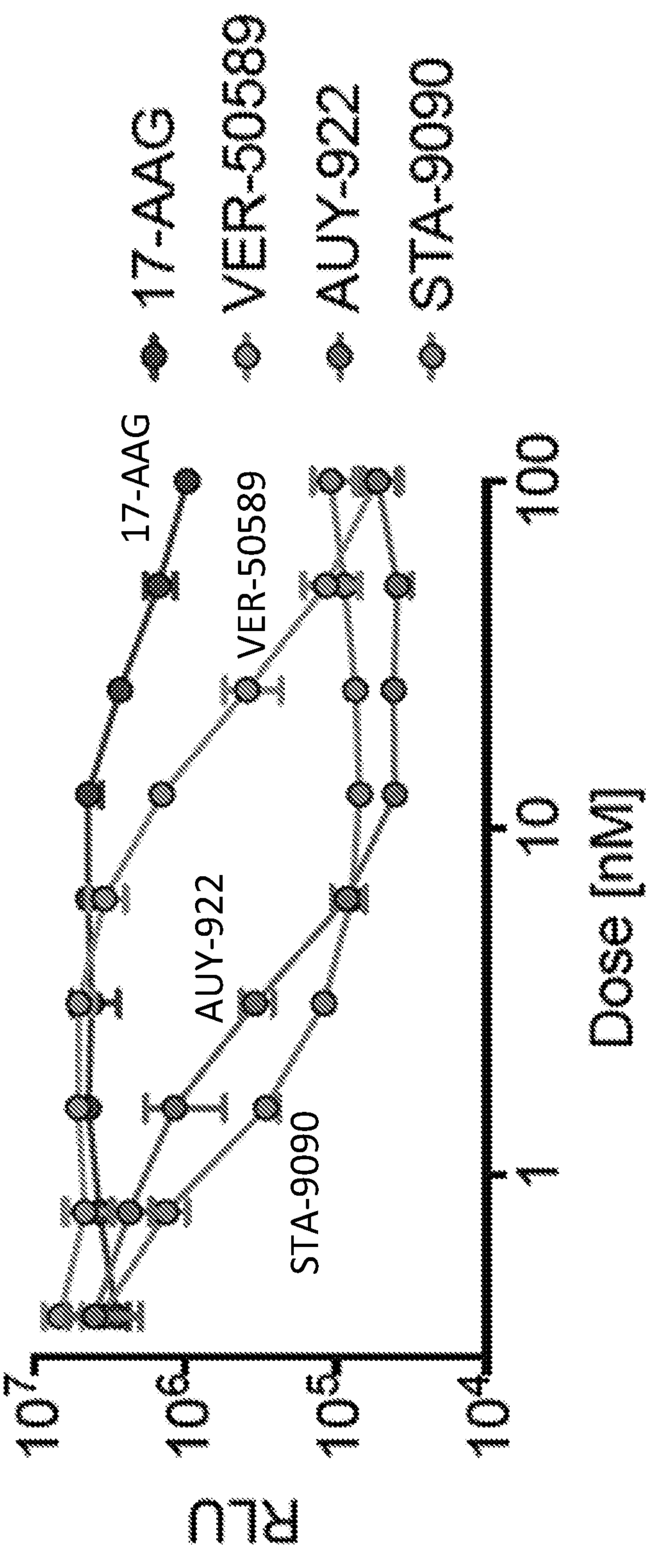
Figure 12A:
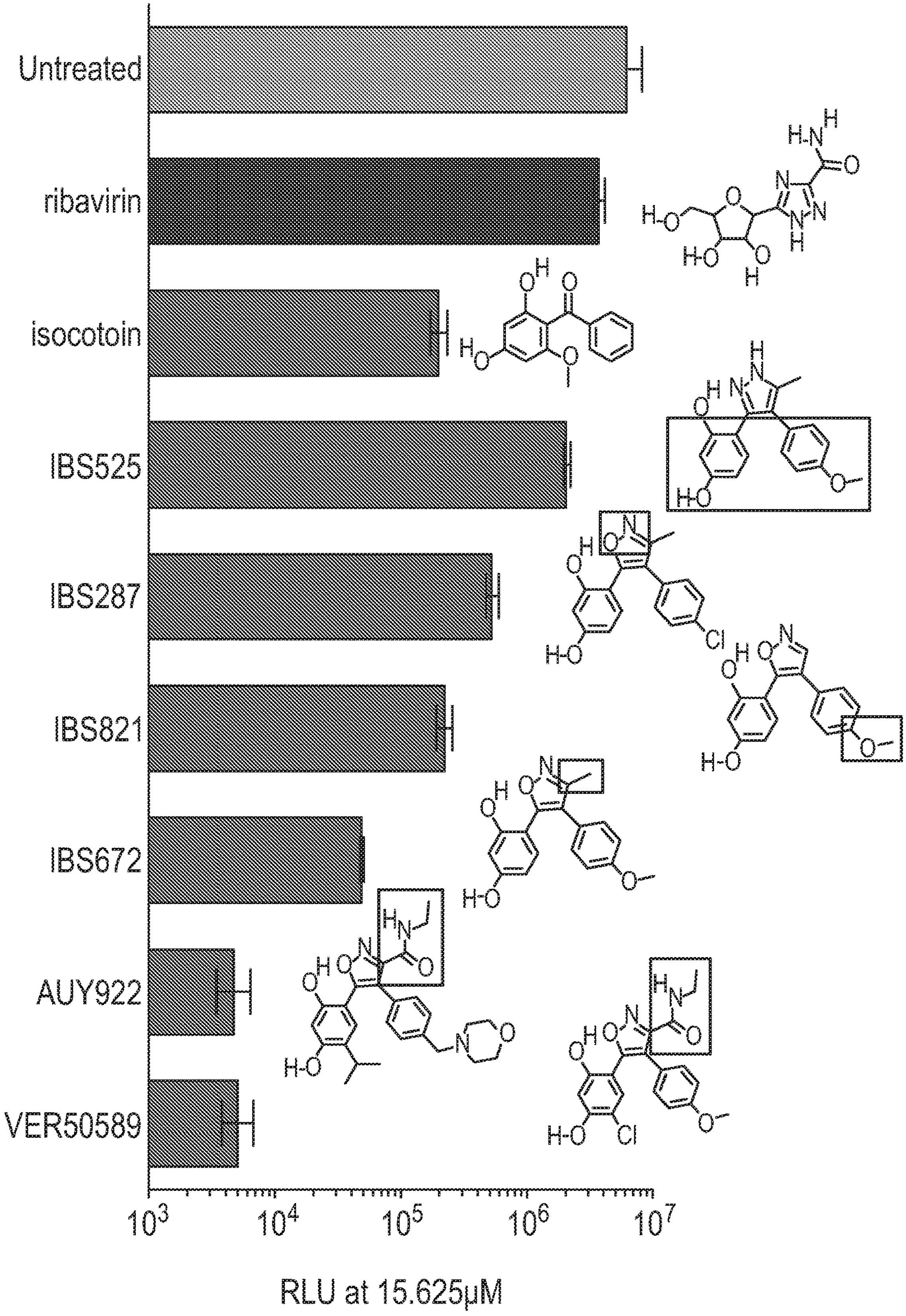
FIGS. 12A-12B. SAR Analysis Data.
Figure 12B:
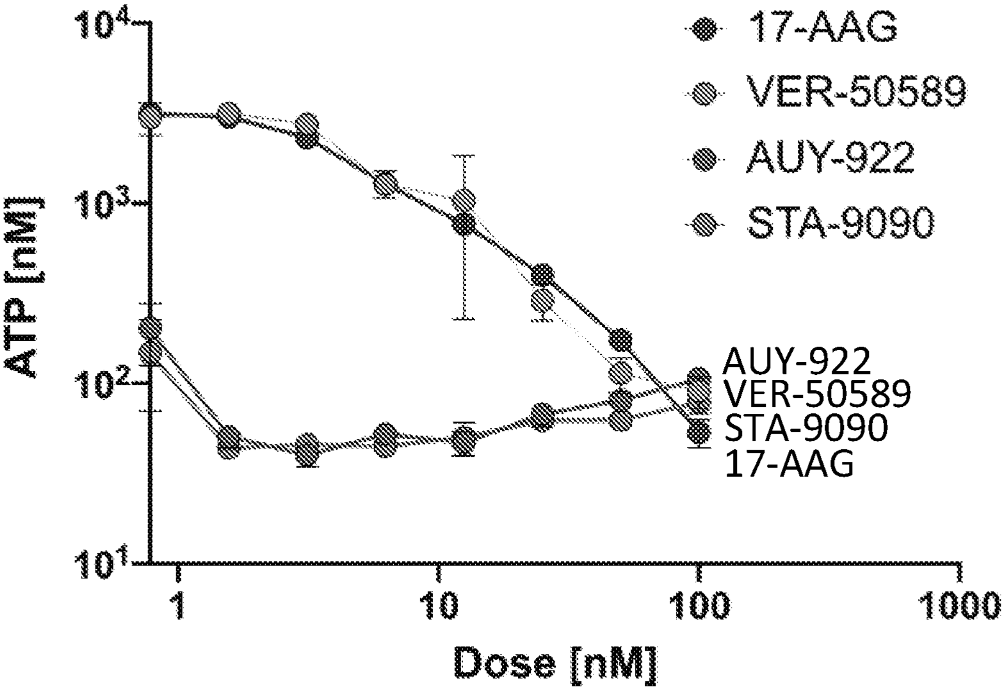
Figure 13:
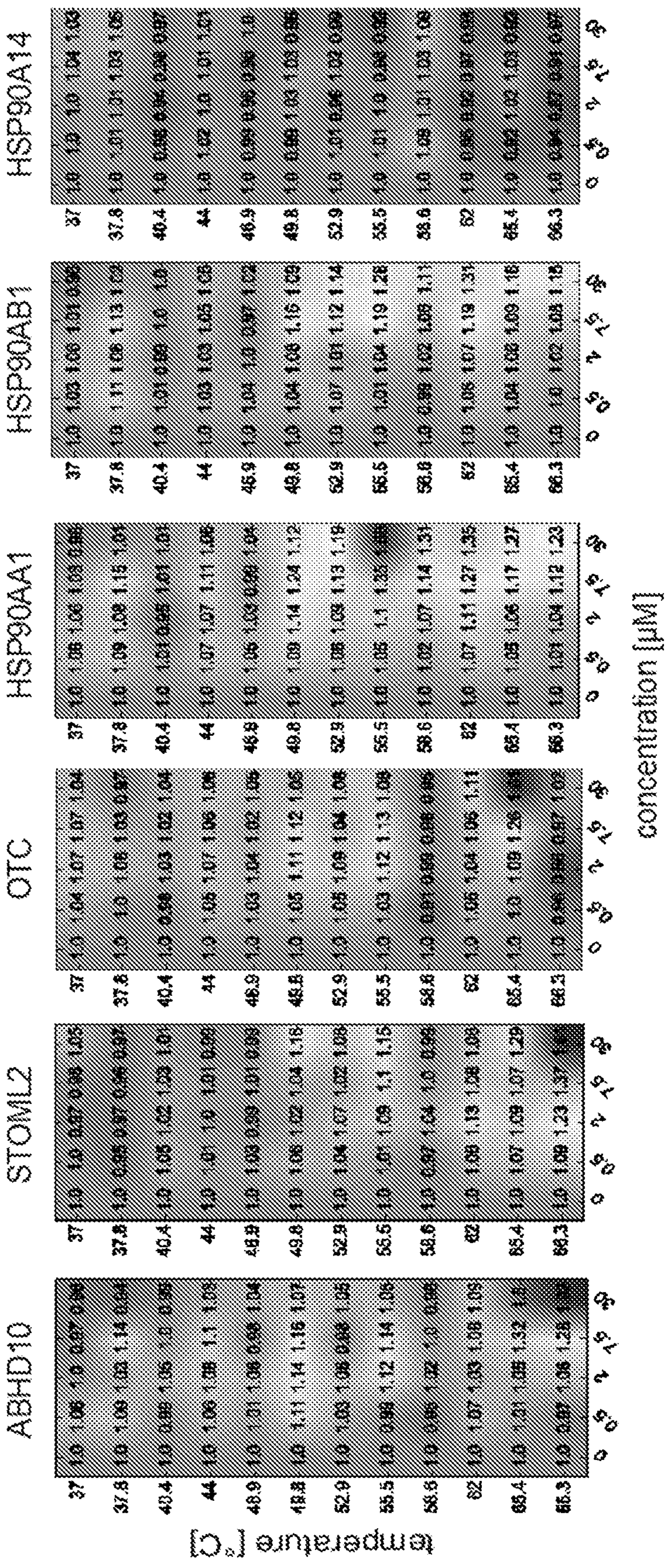
FIG. 13. Cellular Thermal Shift Assay data. Cellular thermal shift data for ABHD10, STOML2, OTC, HSP90AA1, HSP90AB1, and HSPA14. Numbers in heatmaps indicate foldchange in soluble protein at indicated isocotoin concentration and heating temperature. ABHD10, STOML2, OTC, and HSP90AA1 were among hits showing the greatest increase in soluble protein fraction upon addition of drug. HSP90AB1 showed a relatively modest, but identifiable increase. HSPA14 is shown as an example of a protein that did not produce a thermal shift.
Figure 14A:
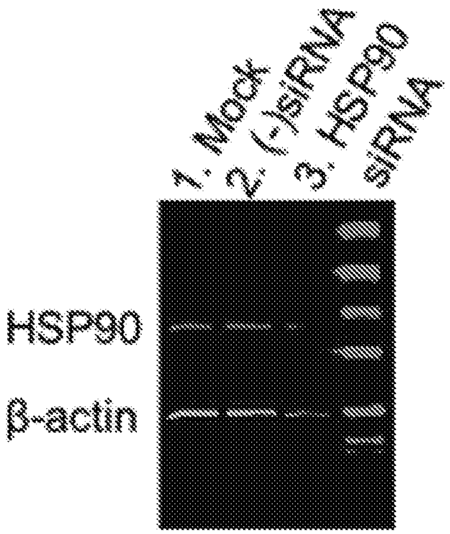
FIGS. 14A-14D. HSP90 knockdown assays.
Figure 14B:
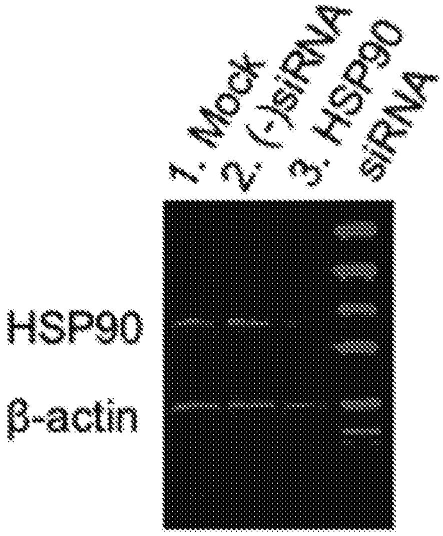
Figure 14C:
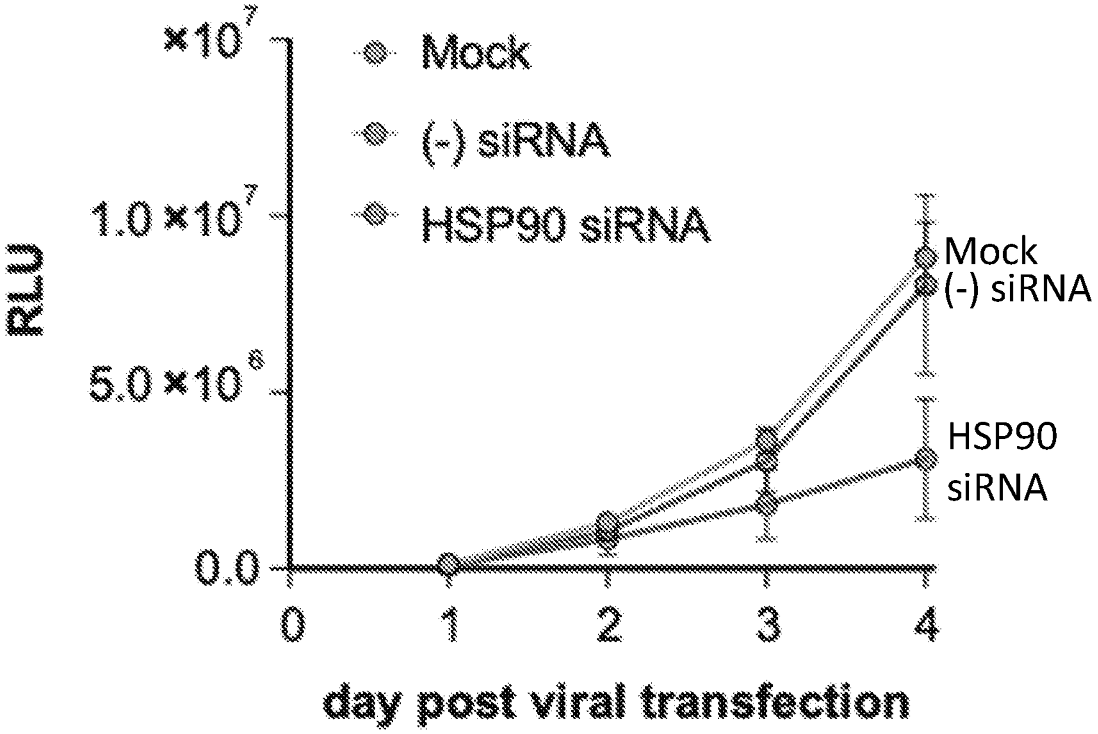
Figure 14D:
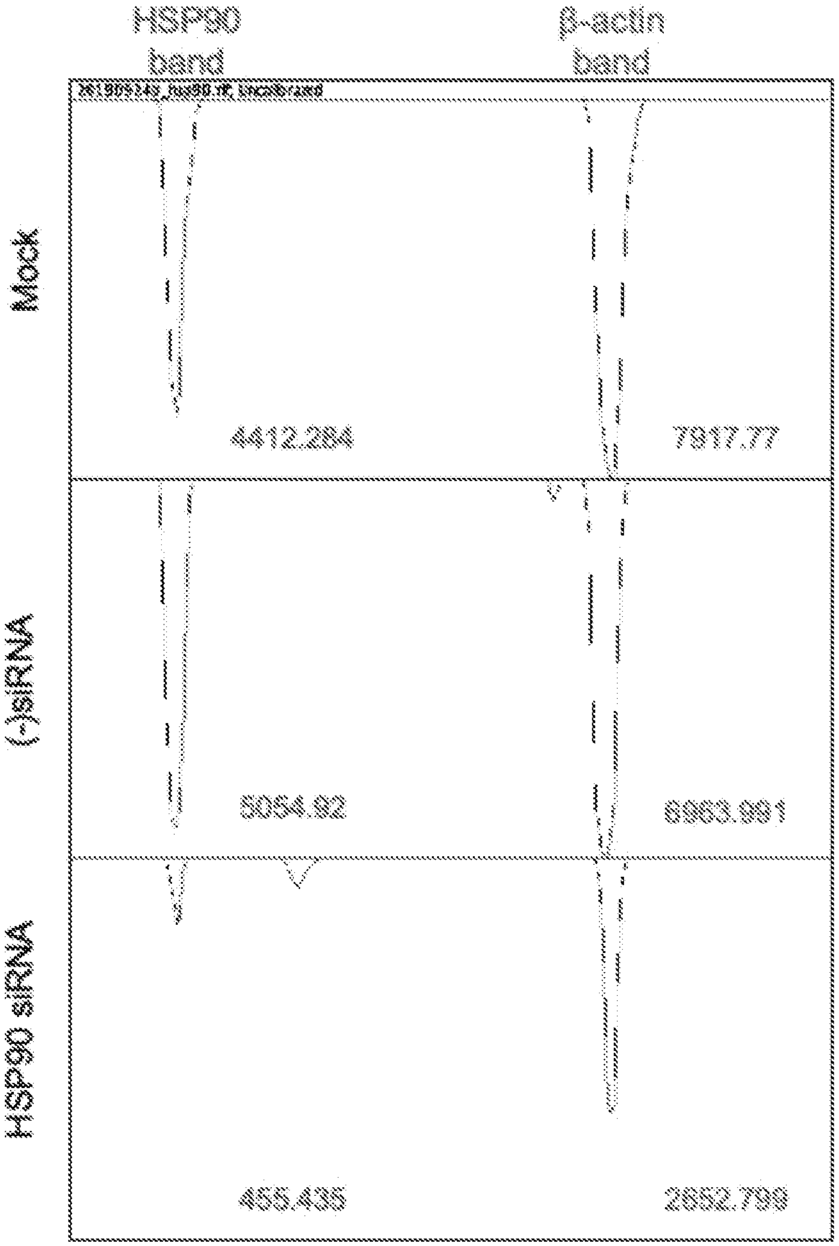

Hsp90 inhibitors, AUY-922 and VER-50589, STA-9090 and 17-AAG, were tested against HEVΔORF2/3[Gluc] replication (FIG. 11C). All four compounds inhibited HEV replication, confirming the essential role of HSP90 in viral replication (FIG. 11C). Unlike isocotoin however, the four compounds exhibited cytostatic properties inhibiting cell growth, and therefore may not be ideal therapeutic candidates for the treatment of hepatitis E (FIGS. 12A, 12B).

Figure 11D:
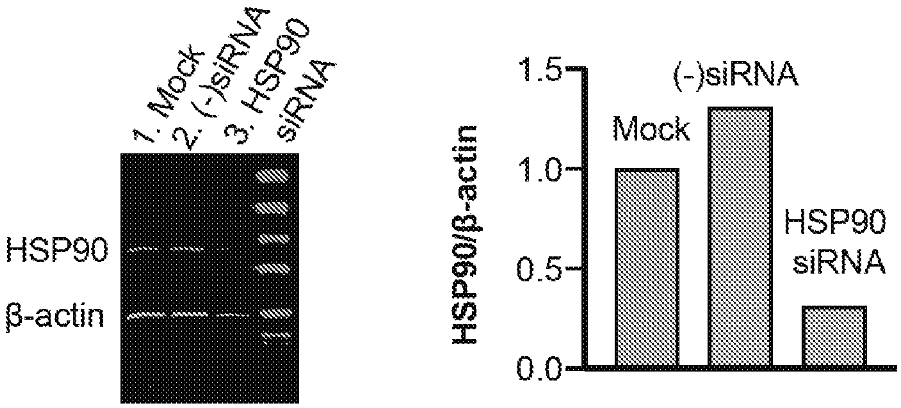
Figure 11E:
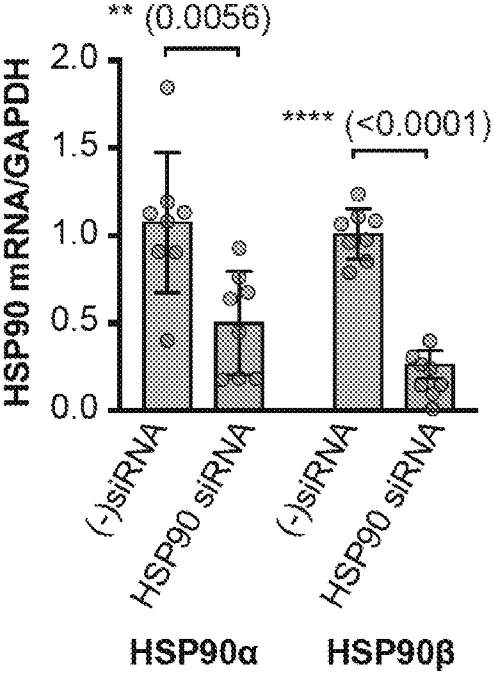
Figure 11F:
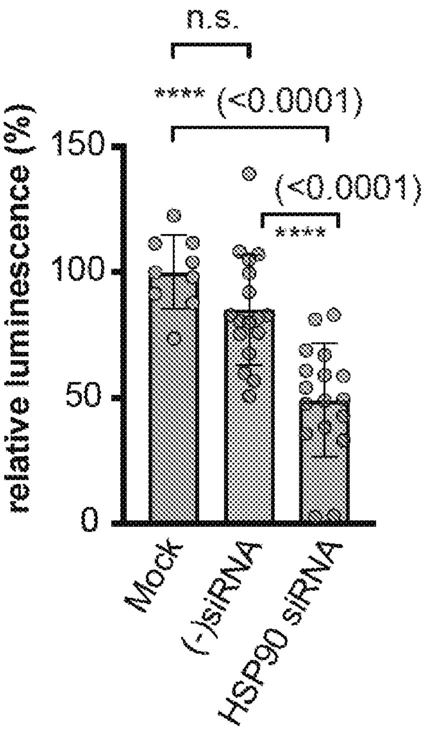
Figure 11G:
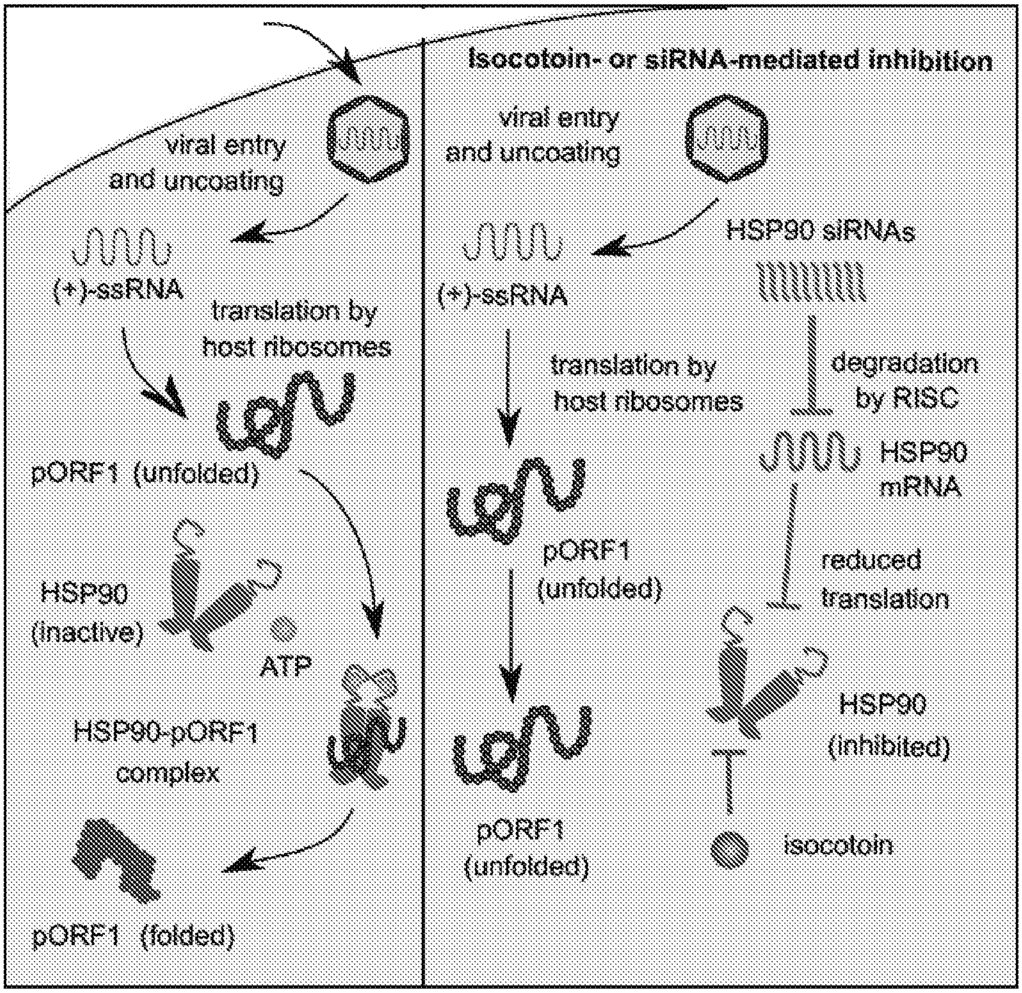

To further corroborate these data, an siRNA-mediated knockdown of Hsp90AA1 and Hsp90AB1 was performed to examine the effect on viral replication. Hsp90 protein levels were reduced 69%, and mRNA levels were reduced 54% for Hsp90AA1 and 74% for Hsp90AB1 post-siRNA transfection (FIGS. 11D, 11E). Seed sequence-matched negative control siRNAs did not demonstrate knockdown of Hsp90 protein or mRNA (FIGS. 11D, 11E). Hsp90 knockdown reduced viral replication by 51% compared to cells treated with transfection reagent only ("mock"), and by 36% compared to cells treated with seed sequence-matched negative control siRNA (FIG. 11F). The incomplete inhibition of viral replication is likely due to incomplete knockdown of HSP90, as demonstrated by Western blot.

In Vivo Functional Validation of Isocotoin

HEV can infect a wide range of hosts including primates, swine, deer, and rabbits. Mice are a small and tractable animal model; however, they are not naturally susceptible to HEV infection. Therefore, to determine whether isocotoin could exert an inhibitory effect against HEV in vivo, a human liver chimeric mouse model, which has previously been shown to be susceptible to HEV, was used. Given that most compounds identified in primary screening assays require extensive pharmacokinetic characterization and chemical modification before translation to an in vivo setting, immediate success of the compound in its current form when tested in mice was not expected.

Figure 15B:
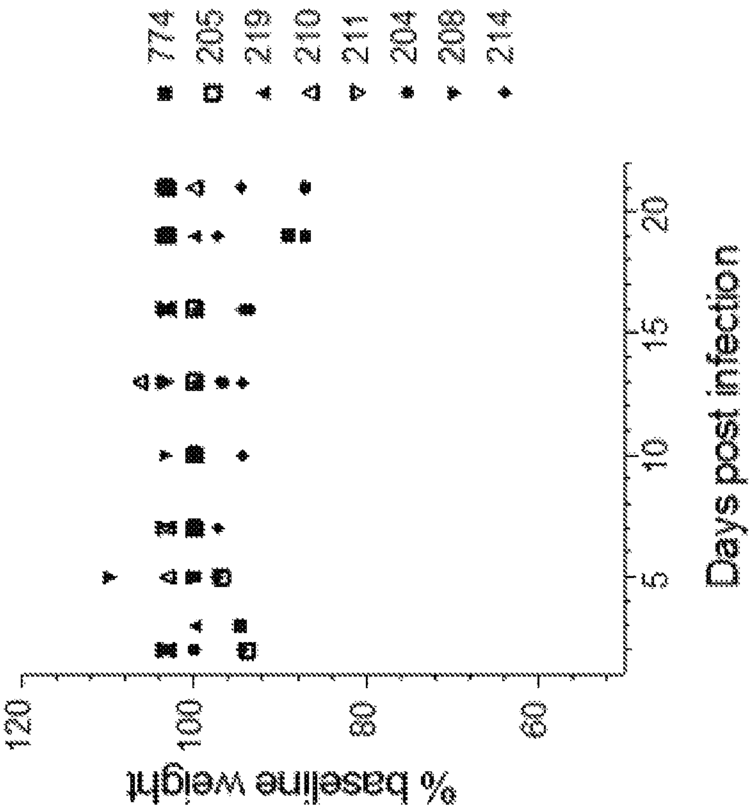
FIGS. 15A-15E. In vivo testing of isocotoin in human liver chimeric mice.
Figure 15A:
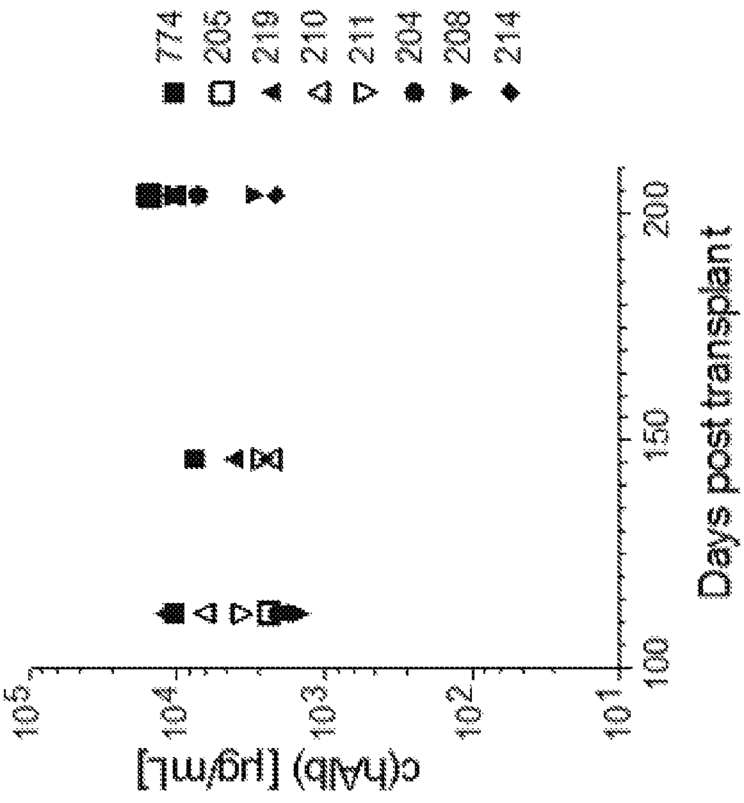
Figure 15C:
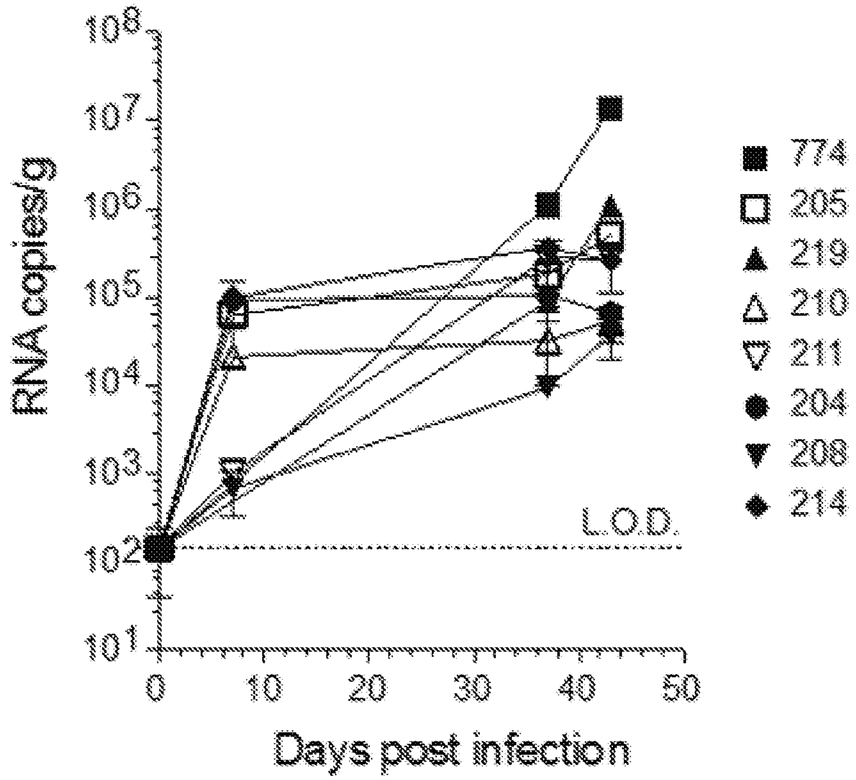

To generate human liver chimeric mice, female fumaryl acetoacetate hydrolase knockout (fah−/−), non-obese diabetic (NOD) recombinase activating gene 1 deficient (rag1−/−) interleukin 2 receptor gamma chain deficient ($il2rg^{NULL}$) (FNRG) mice were injected intrasplenically with commercially obtained human adult hepatocytes. Highly engrafted animals (human albumin concentration in the serum >2.5 mg/ml) were injected intravenously with stool filtrate from HEV-infected rhesus macaques, and viral titers were monitored in the stool and serum. Consistent with previous reports, the animals did not show any symptoms of illness during the course of infection, maintaining stable weight throughout (FIG. 15B).

To test whether isocotoin could lower viral levels in the mice, six mice were drug-treated for 7 days, at a 50 mg/kg dose, injected daily intraperitoneally. No symptoms of drug toxicity were observed in the mice at any point during the treatment. Two infected mice were maintained as untreated controls and were injected with vehicle only. Stool pellets were collected from the mice daily, and blood was drawn pre- and post-treatment. At the end of the treatment period, the mice were euthanized, and their liver tissue was harvested.

Figure 15E:
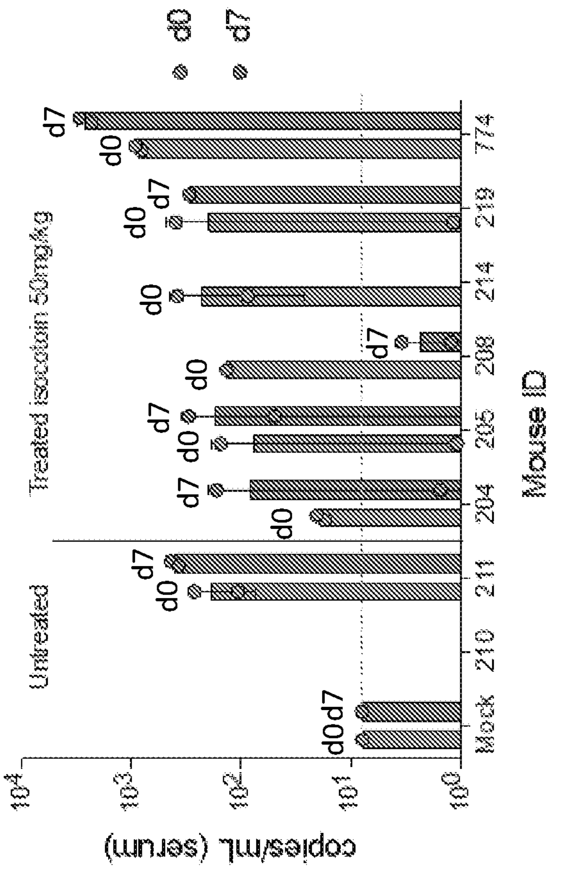
Figure 15D:
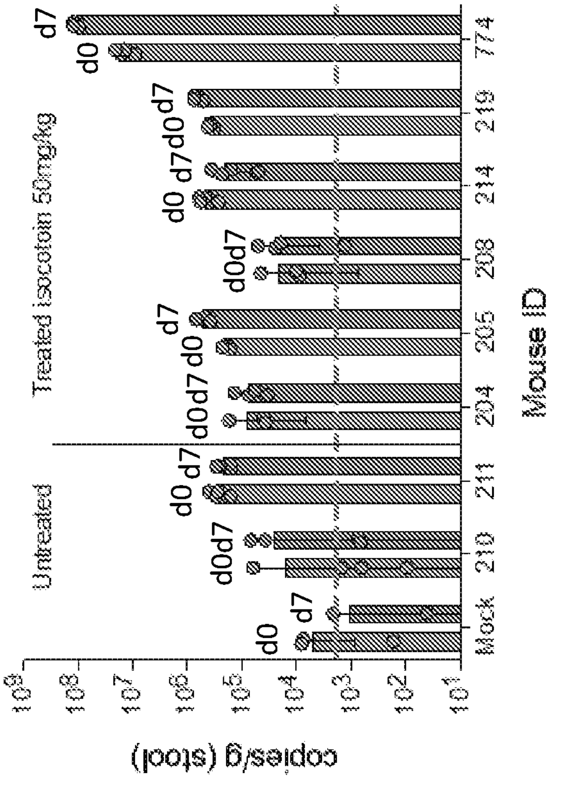

Based on analysis of viral RNA levels in stool and serum pre- and post-treatment, there was not a clear decrease in viral levels from isocotoin treatment (FIGS. 15D and 15E). However, this work is preliminary, and follow-up studies are needed to understand whether the drug is actually reaching the liver in its active form, the pharmacokinetic profile of the drug, and the optimal duration and dose of treatment.

Discussion

This study provides an important step forward in developing therapeutics against HEV infection, where there is a dire need for new treatments, especially for vulnerable patient populations such as immunocompromised individuals and pregnant women. A robust high-throughput screening platform was developed, and used to assess small molecules for inhibitory activity against HEV replication, and isocotoin was identified as a candidate using this assay. Isocotoin was shown to directly bind to two HSP90 proteins, and targeted inhibition or depletion of HSP90 proteins was shown to severely impair HEV replication. Collectively, these data provide the first evidence that HSP90 proteins play an essential role in HEV genomic replication, and suggest that HSP90 inhibitors may provide a novel therapeutic approach for treating hepatitis E. Furthermore, since HSP90 inhibitors employ a distinct mechanism of action from ribavirin, they may be effective in cases of ribavirin resistance, or as combination therapy with ribavirin.

Isocotoin was identified using the p6/BSR-2A-zsGreen replicon, a reporter genome that can be used for future high-throughput studies. A publicly sourced custom script was also developed to rapidly quantify fluorescence in large image datasets and to select promising candidate wells (https://github.com/aploss/PLOCUS). In the screening assay, only one dose (50 μM) per compound was tested. This dose was chosen based on the in vitro efficacy of ribavirin, but as a result, compounds that were effective at lower doses but cytotoxic at the 50 μM dose would not have been selected in the screening assay. However, the assay is adaptable to testing compounds at lower doses, or at multiple doses to calculate dose titrations. Therefore, this platform is a tractable tool for future screening assays against HEV replication.

Two-dimensional thermal proteome profiling (2D-TPP) was used to identify binding targets of isocotoin, towards determining its mechanism of action. The hits identified did not include any HEV viral proteins, which was consistent with the data demonstrating that isocotoin was effective against several different viruses (HCV and YFV-17D) and, therefore, unlikely to be specifically targeting an HEV protein. Though the 2D-TPP measured a relatively modest shift in stability for HSP90 proteins upon addition of isocotoin, protein complexes such as HSP90 typically show smaller thermal shifts from binding interactions due to the initial presence of many pre-existing stabilizing interactions. The assays testing other HSP90 inhibitors against HEV and measuring HEV replication in the presence of HSP90 knockdown confirm the importance of HSP90 for the viral life cycle.

Using the CellTiterGlo assay, which measures ATP levels as a proxy for viable cells, it was found that isocotoin has a similar cytotoxicity profile in vitro to ribavirin. A caveat is that the cytotoxicity assays were performed in hepatoma cell lines, which are more susceptible to HSP90 inhibition than non-tumor derived cell lines. Therefore, cytotoxicity in non-tumor liver cells may actually be lower the results reported herein. Indeed, when mice were treated for seven days with 50 mg/kg doses of isocotoin, no obvious toxicity was observed.

This study also resulted in the discovery of the F470S fitness-enhancing mutation in the putative cysteine protease (PCP) region of p6/Gluc. This mutant strain replicates more robustly in vitro than the wild-type p6/Gluc strain and two previously discovered mutant strains with fitness-enhancing mutations (G1634R and Y1320H, both in the RNA-dependent RNA polymerase region of ORF1). The PCP region of HEV, so-named due to sequence similarity with the rubella virus protease, is poorly understood, and its protease activity remains highly controversial. The discovery of a replication-enhancing mutation in this region provides a look into the important functional sites of this enigmatic domain. Due to its robust replicative capacity, the F470S strain may also prove useful for in vitro studies that require higher replication levels, such as viral production assays.

Preliminary in vivo studies, in which HEV-infected liver chimeric mice were treated with an arbitrary dose of isocotoin for seven days, did not result in a reduction in viral titers. However, as a compound that has never been used in animal studies, extensive in vivo follow-up studies are necessary to understand isocotoin's pharmacokinetic and pharmacodynamic properties, dosing, and potential adverse effects.

In conclusion, a tractable screening assay for the identification of molecules inhibiting HEV replication is disclosed, as is the first evidence that HSP90 proteins play an essential role in HEV genomic replication and may be viable therapeutic targets for treating hepatitis E.

Materials and Methods

Study design. The objective of this study was to identify small molecules with antiviral activity against proteins encoded by HEV ORF1. A high-throughput screening platform was developed to test a library of ~60,000 compounds from the Princeton University Small Molecule Screening Center against a fluorescent HEV replicon. The HEV replicon was derived from the pKernowC1p6 construct, kindly provided by Dr. Suzanne Emerson (NIAID). Images were acquired using the Operetta CLS High Content Screening System (PerkinElmer, Waltham, MA) and analyzed using a custom Python script (https://github.com/aploss/PLOCUS).

All follow-up in vitro experiments to characterize hits were conducted using Huh7 hepatoma cells, with each condition tested in at least three biological replicate wells. No data were excluded from analyses.

Cell lines and culture conditions. Huh7 cells were obtained from the American Tissue Culture Collection (ATCC). These cells were authenticated and were clear of mycoplasma contamination. All cell lines were maintained in Dulbecco's modified Eagle medium (DMEM) (Thermo Fisher) supplemented with 10% (v/v) fetal bovine serum (FBS) (Omega Scientific), 100 U/mL penicillin, and 100 mg/mL streptomycin (P/S). To generate the replicon cell line used in the high-throughput screening assay, Huh7 cells were transfected with p6/BSR-2A-ZsGreen in vitro transcribed RNA and maintained in DMEM 10% FBS, P/S supplemented with 10 µg/mL blasticidin.

Generation of T7-tagBFP-Gluc. To make the T7-TagBFP-GLuc construct, SP6-TagBFP-2A-FLuc was used as a template and the primers PU-O-6099 and PU-O-6100 were designed to partially anneal immediately upstream and downstream of the SP6 promoter. The unbound portions of PU-O-6099 and PU-O-6100 contained the T7 promoter sequence. Subsequent amplification with the Q5® High-Fidelity DNA Polymerase (New England Biolabs, Ipswich, MA) resulted in production of a linear TagBFP-FLuc intermediate construct with T7 overhangs, and ligation was then accomplished using the In-Fusion® HD Cloning Kit (Takara Bio, Mountain View, CA). Next, PCR amplification of the T7-TagBFP-2A backbone was completed using the Q5® High-Fidelity DNA Polymerase and PU-O-6101 and PU-O-6102 as the primers. Separately, amplification of the Gluc gene was accomplished in the same manner, using KernowC1-p6/Gluc as the backbone and PU-O-6103 and PU-O-2783 as the primers. The Gluc insert was then ligated to the T7-TagBFP-2A backbone using the In-Fusion® HD Cloning Kit.

TABLE 1

| Primers | | |
|---|---|---|
| PU-O-6099 | ATACGTAATACGACTCACTATAGAATACAAGCTTATGAGCG | SEQ ID NO 1 |
| PU-O-6100 | AGTCGTATTACGTATGTGTATGATACATAAGGTTATGT | SEQ ID NO 2 |
| PU-O-6101 | CAGAACTTTGACTCCCATCGGTCCAGGATTCTC | SEQ ID NO 3 |
| PU-O-6102 | GCCGGTGGTGACTAAATGGAAGACGCCAAA | SEQ ID NO 4 |
| PU-O-6103 | TTAGTCACCACCGGCC | SEQ ID NO 5 |
| PU-O-2783 | ATGGGAGTCAAAGTTCTGTTTGC | SEQ ID NO 6 |

Generation of p6/Gluc[G1634R] (KernowC1-p6/Gluc [G1634R]), p6/Gluc[Y1320H] (KernowC1-p6/Gluc [Y1320H]), and p6/Gluc[F470S] (KernowC1-p6/Gluc [F470S]) strains. To make the KernowC1-p6/Gluc[Y1320H] construct, QuikChange II XL (Agilent Technologies, Santa Clara, CA) site-directed mutagenesis was performed using KernowC1-p6/GLuc as the template and PU-O-5963 and PU-O-5964 as the primers. Successful incorporation of the mutation was confirmed with Sanger sequencing.

To make the KernowC1-p6/Gluc[G1634R] (KernowC1-p6[G1634R]) construct, QuikChange II XL (Agilent Technologies, Santa Clara, CA) site-directed mutagenesis was performed using KernowC1-p6/GLuc as the template and PU-O-5965 and PU-O-5966 as the primers. Successful incorporation of the mutation was confirmed with Sanger sequencing.

To make the KernowC1-p6/Gluc[F470S] construct, QuikChange (Stratagene) site-directed mutagenesis was performed using KernowC1-p6/Gluc as the template and PU-O— 6433 and PU-O-6434 as the primers. Successful incorporation of the mutation was confirmed with Sanger sequencing.

TABLE 2

| Primers | | |
|---|---|---|
| PU-O-5963 | CGTAGGACGAAGTTACATGAGGCAGCACATTCAGATGTCC | SEQ ID NO: 7 |
| PU-O-5964 | GGACATCTGAATGTGCTGCCTCATGTAACTTCGTCCTACG | SEQ ID NO: 8 |
| PU-O-5965 | CTGTTTGTGATTTCCTTCGAAGGTTGACGAACGTTGCGC | SEQ ID NO: 9 |
| PU-O-5966 | GCGCAACGTTCGTCAACCTTCGAAGGAAATCACAAACAG | SEQ ID NO: 10 |

TABLE 2-continued

| Primers | | |
|---|---|---|
| PU-O-6433 | GAAAGTCGCGGGTAAATCCTGCTGTTTTATGCGG | SEQ ID NO: 11 |
| PU-O-6434 | CCGCATAAAACAGCAGGATTTACCCGCGACTTTC | SEQ ID NO: 12 |

In Vitro Transcription Assay and Viral RNA Transfection. HEV KernowC1-p6, KernowC1-p6/Gluc, KernowC1-p6/Gluc[G1634R], KernowC1-p6/Gluc[Y1320H], and KernowC1-p6/Gluc[F470S] were linearized by MluI. pSAR55-Gluc was linearized by BglII, pGEM-9Zf-pSHEV3-Gluc was linearized by XbaI, and pGEM-7Zf(−)-TW6196E and pGEM-7Zf(−)-TW6196E-Gluc were linearized by SpeI. T7-tagBFP-Gluc was linearized by EcoRI. Viral capped RNAs were transcribed in vitro from linearized plasmid using HiScribe T7 antireverse cap analog (ARCA) mRNA kit (New England Biolabs, Ipswich, MA) according to the manufacturer's instructions. The in vitro transcription (IVT) reaction mixture of 20 μl was assembled by adding DNA template (1 μg), 10 μl of 2×ARCA/nucleotide triphosphate (NTP) mix and 2 μl of T7 RNA polymerase Mix. The reaction mixture was incubated at 37° C. for 3 h, and 2 μl of DNase was added to the IVT reaction mixture and incubated for 15 min at 37° C. to remove the template DNA. Then, the viral RNA was purified by LiCl precipitation. Viral RNA was transfected into Huh7 cells using TransIT-mRNA transfection reagent (Mirus Bio LLC, Madison, WI) according to the manufacturer's instructions.

Dose titration assays. Huh7 cells were seeded in a 96-well plate at a seeding density of 6,250 cells/well. The next day, the cells were transfected with 50 ng/well HEVΔORF2/3 [Gluc] IVT RNA using TransIT-mRNA transfection reagent (Mirus Bio LLC, Madison, WI) according to the instructions. Five hours post-transfection, the cells were incubated in DMEM 10% FBS 0.1% Pen/Strep medium containing isocotoin or ribavirin at the following doses: 200, 100, 50, 25, 12.5, 6.25, 3.125, 1.5625 μM. Three wells were used per dose for triplicate data. Isocotoin and ribavirin compound information is shown below. Most compounds were dissolved in DMSO, and DMSO concentration was kept constant at 0.1% in all wells.

| Structure | IUPAC Name | Vendor Information | Abbreviation |
|---|---|---|---|
| 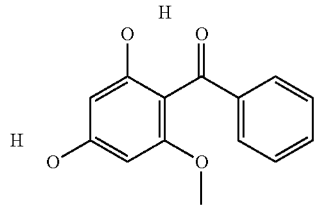 | 4-benzoyl-5-methoxybenzene-1,3-diol | MicroSource Discovery 201519 | isocotoin |
| 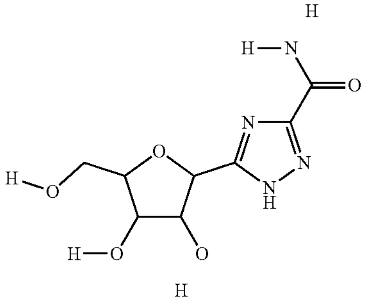 | 1-[(2R,3R,4S,5R)-3,4-dihydroxy-5-(hydroxymethyl)oxolan-2-yl]-1,2,4-triazole-3-carboxamide | Sigma R9644 | ribavirin |

*Gaussia luciferase* assays. *Gaussia luciferase* activity was determined using Luc-Pair *Renilla luciferase* HS assay kit (GeneCopoeia, Rockville, MD). Specifically, 10 μl of harvested cell culture medium was added per well of a 96-well solid white, flat-bottom polystyrene microplate (Corning, NY, USA), followed by the addition of *Renilla luciferase* assay substrate and the detection of luminescence was performed using a Berthold luminometer.

Quantification of HEV RNA by RT-qPCR Assay. Huh7 cells were seeded 42,000 cells/well in 24-well plates. One day post-seeding, the cells were transfected with 10 ng/well KernowC1p6 or KernowC1p6-GAD in vitro transcribed RNA. The next day, the medium on the cells transfected with KernowC1p6 was changed to 0.1% DMSO medium containing 25 μM, 12.5 μM, 6.25 μM, or 0 μM isocotoin. The negative control cells transfected with KernowC1p6-GAD were maintained in medium with 0.1% DMSO. The media on the cells was changed every 2 days to fresh drug-containing or DMSO-containing media. On day 6, cells were harvested and lysed in RLT buffer using 350 μL per well. Cell lysates were homogenized by pipetting 6-7 times with a needle syringe. Total RNA was extracted using BioBasic RNA MiniPreps SuperKit (Amherst, NY). RT-qPCR was performed on the samples using qScript XLT 1-Step RT-qPCR ToughMix (Quanta Bio) according to the manufacturer's instructions. In vitro transcribed KernowC1p6 RNA of known concentration was serially diluted 1:10 and included as controls to generate a standard curve to calculate absolute RNA copies/μL in the samples.

TABLE 3

| Primers for HEV RNA quantification | | |
|---|---|---|
| Forward | GGTGGTTTCTGGGGTGAC | SEQ ID NO 13 |
| Reverse | AGGGGTTGGTTGGATGAA | SEQ ID NO 14 |
| FAM-BHQ Probe | TGATTCTCAGCCCTTCGC | SEQ ID NO 15 |

Measurement of Cytotoxicity by CellTiterGlo Assay. Huh7 cells were seeded in a 96-well plate at a seeding density of 6,250 cells/well. The next day, the cells were incubated in DMEM, 10% FBS, 0.1% Pen/Strep medium containing isocotoin or ribavirin at the following doses: 200, 100, 50, 25, 12.5, 6.25, 3.125, 1.56 μM. Three wells were used per dose for triplicate data. On day 4, ATP quantity was determined using CellTiter-Glo 2.0 Assay (Promega, Madison, WI) according to the manufacturer's instructions. Readout was performed using a Berthold luminometer.

Translation Inhibition Assay. Huh7 cells were seeded at 6,250 cells per well in 96-well format. The cells were then transfected with 50 ng T7-TagBFP-Gluc in vitro transcribed RNA per well. Five hours post-transfection, transfection medium was changed to medium containing isocotoin, ribavirin, cycloheximide, or roclagamide at 6 or 7 different concentrations. DMSO concentration was kept constant in all the wells at 0.125%. For each drug dose, triplicate wells were tested. On day four post-transfection, a luciferase assay was performed on supernatant media to measure Gluc expression.

Statistics—calculation of IC50. Half maximal inhibitory concentrations were calculated by graphing dose-titration data as nonlinear curve fits with three parameters using GraphPad Prism (v8.1.2).

Replication kinetics assay. Huh7 cells were seeded in 6-well plates at $2\times10^5$ cells/wells. One day post-seeding, the cells were transfected with 1 ug/well in vitro transcribed RNA of p6/Gluc (HEVΔORF2/3[Gluc]), HEVΔORF2/3 [Gluc][F398S], p6/Gluc[F470S], p6/Gluc[G1634R] (HEVΔORF2/3[Gluc][G1634R]), or p6/Gluc[Y1320H] (HEVΔORF2/3[Gluc][Y1320H]). 50 μL supernatant was collected on each day up to day 4 and stored at −20° C. On day 4 post-transfection, a luciferase assay was performed on the supernatant collections to measure Gluc expression.

Gluc-expressing HCV and YFV-17D strains. The pACNR-FLYF-17D-Gluc-BSD-Ires construct was derived from pACNR/FLYF-17D (GenBank ID: AY640589). Briefly, a *Gaussia luciferase* (Gluc)-P2A-Blasticidin resistance gene (BSD)-EMCV Ires cassette (Gluc-P2A-BSD-Ires) was introduced downstream of the capsid protein, thereby replacing most of the PrM and E protein coding sequence. The Gluc-P2A-BSD-Ires cassette was flanked by the first six amino acids of Pr and by the 26 last amino acids of E to allow for correct Glue and NS1 protein processing. The Jc1(p7nsGluc2A) is a J6/JFH genome that includes a *Gaussia luciferase* gene inserted between p7 and NS2.

Suboptimal Dosing Assay to Identify Resistance Mutations. Huh7 cells were transfected with p6/BSR-2A-ZsGreen in vitro transcribed RNA and passaged in the presence of 10 ug/mL blasticidin to generate a population that was 85-95% positive for ZsGreen expression, measured using flow cytometry. The Huh7[p6/BSR-2A-ZsGreen] cells were then seeded in 6-well format and passaged in the presence of isocotoin, 10 ug/mL blasticidin, or 0.15% DMSO. At each passage, ⅓ of cells were analyzed with flow cytometry, ⅓ of cells were lysed in RLT buffer and stored at −80° C., and ⅓ cells were seeded in a fresh 6-well plate to continue serial passaging.

Viral Sequencing. RNA was extracted from cell lysates using the BioBasic kit according to the manufacturer's instructions. cDNA was generated using the iScript Reverse Transcriptase kit according to manufacturer's instructions. PCR fragments were amplified using Bullseye Taq polymerase in order to generate TA overhangs for TOPO cloning. Subsequently the Takara TOPO-TA cloning kit was used according to manufacturer's instructions. Sequence alignment and analysis was performed using SnapGene software.

Flow Cytometry Analysis. Expression of p6/BSR-2A-ZsGreen was analyzed by flow cytometry on a BD LSRII flow cytometer (five-laser SORP LSRII with high-throughput sampler). Huh7 cells were transfected with p6/BSR-2A-ZsGreen and passaged in DMEM 10% FBS 1% PS containing 10 μg/mL blasticidin to select for successfully transfected cells. After 3 days of transduction, cells were fixed in 4% (wt/vol) paraformaldehyde (PFA) in phosphate-buffered saline (PBS) for 15 min, followed by one wash with PBS. The efficiencies of transduction of transgenes were determined by simultaneous expression of ZsGreen. All samples were analyzed on a BD LSRII flow cytometer using FlowJo software.

Two-dimensional thermal proteome profiling (2D-TPP) in crude cell extract. Two-dimensional thermal proteome profiling was performed as previously described (PMID: 30858367). Briefly, Huh7 cells transfected with KernowC1-p6/BSR-2A-ZsGreen were selected under blasticidin pressure (10 g/mL) to generate a cell population highly expressing ORF1 proteins. The cells were lysed in cold PBS with three freeze/thaw cycles in liquid nitrogen followed by mechanical shearing. Aliquots of this crude lysate were incubated with vehicle (DMSO) or isocotoin at 0.5 μM, 2 μM, 7.5 μM or 30 μM for 10 min at 25° C. The samples were aliquoted to a PCR plate, and heated for 3 min to ten different temperatures (37° C.-66.3° C.) in a PCR machine (Agilent SureCycler 8800). The crude lysates were further treated with NP-40 and benzonase (final concentration: 0.8% NP40, 1.5 mM $MgCl_2$, 1×cOmplete protease inhibitor (Roche), 1×PhosSTOP (Roche), 250 U/ml benzonase in PBS) for 1 h at 4° C. Removal of protein aggregates was performed as previously described (PMID: 29980614), and the remaining soluble proteins were digested overnight according to a modified SP3 protocol (PMID: 25358341; PMID: 30464214). Peptides were labeled with TMT10plex (ThermoFisher Scientific), fractionated into twelve fractions under high pH conditions and analyzed with liquid chromatography coupled to tandem mass spectrometry, as previously described (PMID: 29706546). Protein identification and quantification was performed using IsobarQuant (PMID: 26379230) and Mascot 2.4 (Matrix Science) against a FASTA file with *Homo sapiens* (Proteome ID: UP000005640) and the protein sequence of ORF1 polyprotein from Hepatitis E virus (Uniprot ID: H9E9C7_HEV). Data was analyzed with the TPP package for R (PMID: 26379230).

Data availability: The mass spectrometry proteomics data have been deposited to the ProteomeXchange Consortium (http://www.proteomexchange.org) via the PRIDE partner repository with the dataset identifier PXD014485.

Plotting—heat maps. Heatmaps were plotted using Xcode (v10.2.1).

Hsp90 knockdown experiments. Pooled siRNAs targeting HSP 90α/β were purchased from Santa Cruz Biotechnology (sc-35608, Cruz Biotechnology, Dallas, TX), and seed sequence-matched siRNAs were custom designed to use as negative controls for knockdown assays (Sigma, Madison, WI)[38]. For knockdown experiments, Huh7 cells were reverse transfected with 50 nM HSP 90α/β siRNA or negative control siRNA using Dharmafect 4 Transfection Reagent (Dharmacon, Lafayette, CO) according to the manufacturer's instructions.

Transfection of HEVΔORF2/3[Gluc] following HSP90 knockdown. One day after reverse transfection with siRNA, Huh7 cells were transfected with 6.25 ng HEVΔORF2/3 [Gluc] in vitro transcribed RNA per well of a 96-well plate using TransIT-mRNA transfection reagent (Mirus Bio LLC, Madison, WI) according to the instructions. The medium on the cells was changed 5 hours post transfection. Supernatant was collected on day 3 for *Gaussia luciferase* measurement.

RTqPCR analysis. Cells were lysed on day 2 post siRNA reverse transfection using RLT buffer, and total RNA was extracted using BioBasic RNA MiniPreps SuperKit (Amherst, NY). RTqPCR analysis was performed using SYBR® Green PCR Master Mix (Thermo Fisher Scientific) and MultiScribe™ Reverse Transcriptase (Thermo Fisher Scientific) according to the manufacturer's instructions. Each sample was measured in quadruplicate wells. Results were normalized to average GAPDH housekeeping gene levels.

TABLE 4

| Primers used for RTqPCR | | |
|---|---|---|
| HSP90AA1-F | CATAACGATGATGAGCAGTACGC | SEQ ID NO 16 |
| HSP90AA1-R | GACCCATAGGTTCACCTGTGT | SEQ ID NO 17 |
| HSP90AB1-F | AGAAATTGCCCAACTCATGTCC | SEQ ID NO 18 |
| HSP90AB1-R | ATCAACTCCCGAAGGAAAATCTC | SEQ ID NO 19 |
| GAPDH-F | GAAGGTGAAGGTCGGAGTC | SEQ ID NO 20 |
| GAPDH-R | GAAGATGGTGATGGGATTTC | SEQ ID NO 21 |

ΔΔCt values were calculated to determine fold difference in HSP90α, and β RNA levels between siRNA-transfected and negative control-transfected cells.

Western blotting. Sodium dodecyl sulfate-polyacrylamide gel electrophoresis (SDS-PAGE) immunoblotting was performed as follows: After trypsinization and cell pelleting at 2,000×g for 10 min, whole-cell lysates were harvested in RIPA lysis buffer (50 mM Tris-HCl [pH 8.0], 150 mM NaCl, 1% NP-40, 0.5% sodium deoxycholate, and 0.1% SDS) supplemented with protease inhibitor cocktail (ThermoFisher Scientific, Waltham, MA). Lysates were electrophoresed in 10% polyacrylamide gels and transferred onto nitrocellulose membrane. The blots were blocked at room temperature for 30 min using 5% nonfat milk in 1×phosphate-buffered saline (PBS) containing 0.1% (v/v) Tween 20. The blots were exposed to primary antibodies (anti HSP90α/β (sc-13119, Santa Cruz Biotechnology, Dallas, TX) and anti-β-actin (13E5, Cell Signaling Technology, Danvers, MA) in 5% nonfat milk in 1×PBS containing 0.1% Tween 20 overnight. The blots were then washed in 1×PBS containing 0.1% Tween 20. Afterwards, 30 min exposure to DyLight800 and DyLight680-conjugated secondary antibodies and subsequent washes were performed as described for the primary antibodies. Membranes were visualized using the Odyssey CLx Imaging System (LI-COR Biotechnology, Lincoln, NE) and images were processed using ImageJ Version 2.0.0-rc-43/1.50e[39].

Screening Assay

Small Molecule Library. The Princeton University Small Molecule Screening Center currently has 75,000 singleton compounds as 10 mM DMSO solutions. This collection was assembled from evaluation of over 10 million commercially available compounds, with consideration to include tractable, drug-like chemical entities while maintaining maximum internal chemical diversity and remaining differentiated from compound collections at typical academic screening centers. Compounds were sourced from (including, but not limited to) Chemdiv, Chembridge, Asinex, Aldrich, Molecular Spectrum and Selleckchem. Bulk liquid and reagent handling is accomplished using the Bravo Automated Liquid Handling Platform (Agilent Technologies). Dispensing of small molecule solutions is achieved using the Echo® 550 Liquid Handler (Labcyte, San Jose, CA), a non-contact acoustic dispenser.

Screening Assay Setup. 384-well plastic tissue culture plates were seeded with 150 nL of compounds dissolved as 10 mM DMSO stock solutions using the Echo® 550 Liquid Handler. 30 μL Huh7 cells transfected with p6/BSR-2A-ZsGreen ("replicon cells") were then seeded in the wells at a density of 8,000 cells per well, using a MultiDrop Combi Reagent Dispenser (Thermo Fischer Scientific). In each plate, 64 wells were reserved for positive control untreated cells (32 wells) and for negative control, non-fluorescent naïve Huh7 cells (32 wells). After four days, transmitted light and GFP fluorescence images were taken of the wells (in total, two images per well) using the Operetta CLS High Content Screening System (PerkinElmer, Waltham, MA).

Image Analysis. A custom Python script was developed to analyze the effectiveness of different substances for inhibition of viral replication with a high throughput. This involved analyzing images of wells from 188 plates, each containing 384 wells, 32 of which were dedicated to negative controls and 32 to positive controls. Using the tail differentials in the color distribution of fluorescence images, wells similar to the negative controls were tagged. The algorithm was tuned to maximize Z-factors and thus, confidence, in determining potential matches. Finally, the program listed candidate wells in importance order, and this list was used to manually verify the visual image of the wells to eliminate cytotoxic wells.

Second-Round Screening. 37 compounds selected for second-round screening were seeded at eight concentrations in duplicate using the Echo® 550 Liquid Handler (Labcyte). Huh7 replicon cells were then seeded in the wells at 8000 cells per well using the MultiDrop Combi Reagent Dispenser (Thermo Fischer Scientific). Image acquisition was performed using the Operetta CLS High Content Screening System (PerkinElmer), and analysis was performed with the previously mentioned custom Python script. GraphPad Prism was used to plot dose titration curves and calculate IC50 values for each compound.

Structure-Activity Relationship Analysis

Compound preparation. All SAR analysis compounds (listed in Appendices 1, 1', 2, 2', 3) were ordered in powder form and dissolved in DMSO to a 10 mM concentration. 10 μL aliquots were stored at −80° C. When conducting the dose titration experiments, the compounds to be tested were thawed fresh from −80° C. and used immediately.

Dose titration assays. Huh7 cells were seeded 6,250 cells/well in a 96-well plate one day prior to treatment. The outer wells of each plate were not used as experimental wells due to increased evaporation and were instead filled with 200 μL PBS to keep the plates humidified. On the day of treatment, the cells were transfected with 50 ng/well p6/Gluc in vitro transcribed RNA using TrasIT mRNA transfection reagent (Mirus Bio LLC, Madison, WI) according to the manufacturer's instructions. Five hours later, the medium on the cells was changed to medium containing compounds to be tested at doses ranging from 0.39 μM to 100 μM. Each dose was tested in triplicate, and isocotoin and ribavirin were included as controls in all experiments. To prepare the compound-containing media, the 10 mM aliquots of compound in DMSO were thawed and dissolved in DMEM 10% FBS 0.1% Pen/Strep to make 100 μM solutions. The 100 μM solutions were then serially diluted 1:2 in DMEM 10% FBS 0.1% Pen/Strep to generate 50, 25, 12.5, 6.25, 3.125, 1.5625, 0.78125, and 0.39 μM solutions. The cells were left in 166 μL/well compound-containing media for 4 days, with a luciferase readout performed on day 4.

APPENDIX 1

SAR Analysis Round 1 Molecules

| Structure | IUPAC Name | Vendor Information | Abbreviation |
|---|---|---|---|
| 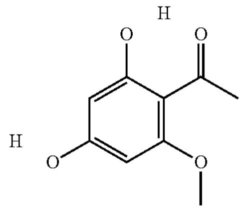 | 1-(2,4-dihydroxy-6-methoxyphenyl)ethanone | ChemFaces CFN98488 | CHE488 |
| 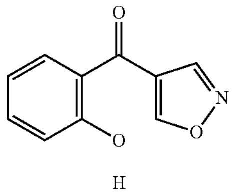 | (2-hydroxyphenyl)-(1,2-oxazol-4-yl)methanone | Enamine Z57983002 | ENA002 |
| 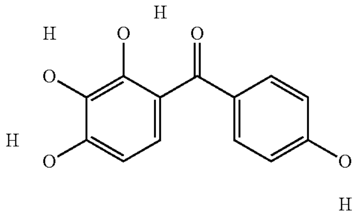 | (4-hydroxyphenyl)-(2,3,4-trihydroxyphenyl)methanone | InterBioScreen Ltd STOCK2S-11493 | IBS493 |
| 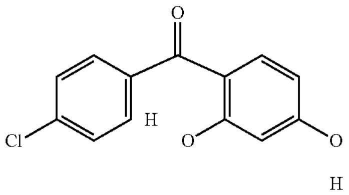 | (4-chlorophenyl)-(2,4-dihydroxyphenyl)methanone | InterBioScreen Ltd STOCK7S-53102 | IBS102 |
| 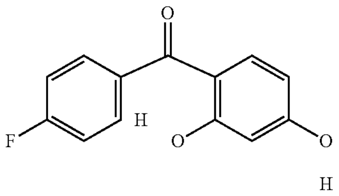 | (2,4-dihydroxyphenyl)-(4-fluorophenyl)methanone | InterBioScreen Ltd STOCK7S-53659 | IBS659 |
| 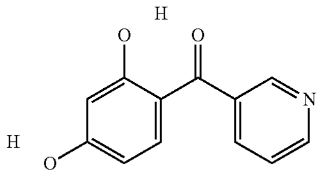 | (2,4-dihydroxyphenyl)-pyridin-3-ylmethanone | InterBioScreen Ltd STOCK6S-83914 | IBS914 |

APPENDIX 1-continued

| SAR Analysis Round 1 Molecules | | | |
|---|---|---|---|
| Structure | IUPAC Name | Vendor Information | Abbreviation |
| 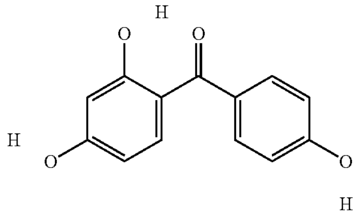 | (2,4-dihydroxyphenyl)-(4-hydroxyphenyl)methanone | InterBioScreen Ltd STOCK2S-15237 | IBS237 |
| 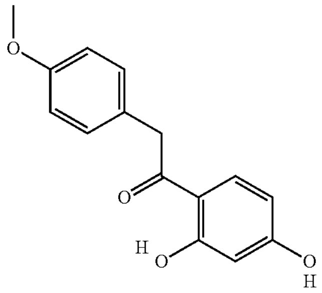 | 1-(2,4-dihydroxyphenyl)-2-(4-methoxyphenyl)ethanone | InterBioScreen Ltd STOCK5S-54694 | IBS694 |
| 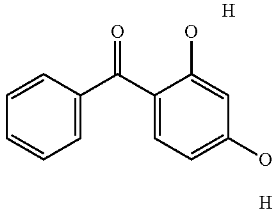 | (2,4-dihydroxyphenyl)-phenylmethanone | Specs AE-641/01968047 | SPE047 |
| 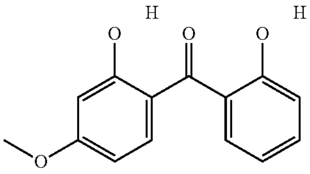 | (2-hydroxy-4-methoxyphenyl)-(2-hydroxyphenyl)methanone | AK Scientific K820 | K820 |
| 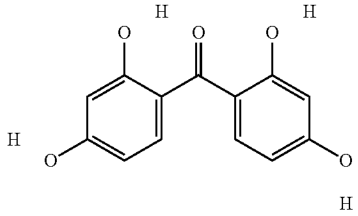 | bis(2,4-dihydroxyphenyl) methanone | AK Scientific I955 | I955 |

APPENDIX 1'

| SAR Analysis Round 1 Molecules | | | |
|---|---|---|---|
| Structure | IUPAC Name | Vendor Information | Abbreviation |
| 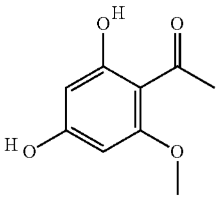 | 1-(2,4-dihydroxy-6-methoxyphenyl)ethanone | ChemFaces CFN98488 | CHE488 |

APPENDIX 1'-continued

| SAR Analysis Round 1 Molecules | | | |
|---|---|---|---|
| Structure | IUPAC Name | Vendor Information | Abbreviation |
| 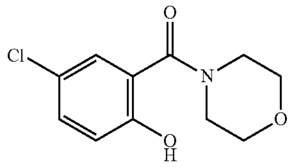 [SMILES: O=C(c1cc(Cl)ccc1O)N1CCOCC1] | (5-chloro-2-hydroxyphenyl)-morpholin-4-ylmethanone | Enamine Z68158728 | ENA728 |
| 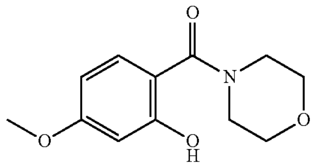 [SMILES: COc1ccc(C(=O)N2CCOCC2)c(O)c1] | (2-hydroxy-4-methoxyphenyl)-morpholin-4-ylmethanone | Enamine Z68159307 | ENA307 |
| 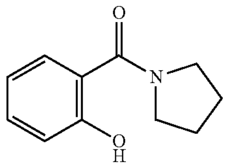 [SMILES: O=C(c1ccccc1O)N1CCCC1] | (2-hydroxyphenyl)-pyrrolidin-1-ylmethanone | Enamine Z235583000 | ENA000 |
| 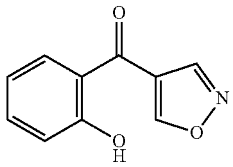 [SMILES: O=C(c1cnoc1)c1ccccc1O] | (2-hydroxyphenyl)-(1,2-oxazol-4-yl)methanone | Enamine Z57983002 | ENA002 |
| 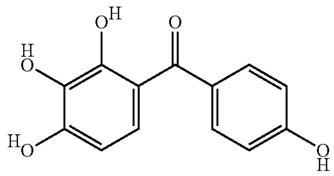 | (4-hydroxyphenyl)-(2,3,4-trihydroxyphenyl)methanone | InterBioScreen Ltd STOCK2S-11493 | IBS493 |
| 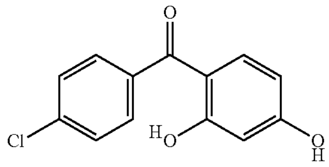 | (4-chlorophenyl)-(2,4-dihydroxyphenyl)methanone | InterBioScreen Ltd STOCK7S-53102 | IBS102 |
| 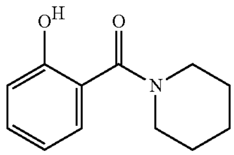 | (2-hydroxyphenyl)-piperidin-1-ylmethanone | InterBioScreen Ltd STOCK5S-49711 | IBS711 |
| 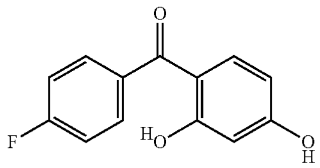 | (2,4-dihydroxyphenyl)-(4-fluorophenyl)methanone | InterBioScreen Ltd STOCK7S-53659 | IBS659 |

APPENDIX 1'-continued

| SAR Analysis Round 1 Molecules | | | |
|---|---|---|---|
| Structure | IUPAC Name | Vendor Information | Abbreviation |
| 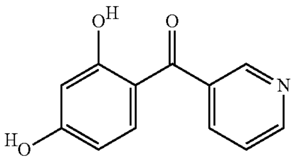 | (2,4-dihydroxyphenyl)-pyridin-3-ylmethanone | InterBioScreen Ltd STOCK6S-83914 | IBS914 |
| 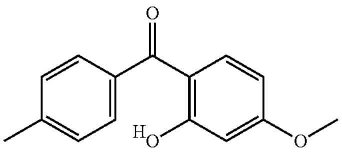 | (2-hydroxy-4-methoxyphenyl)-(4-methylphenyl)methanone | InterBioScreen Ltd STOCK6S-58266 | IBS266 |
| 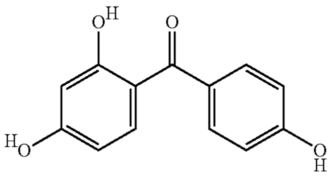 | (2,4-dihydroxyphenyl)-(4-hydroxyphenyl)methanone | InterBioScreen Ltd STOCK2S-15237 | IBS237 |
| 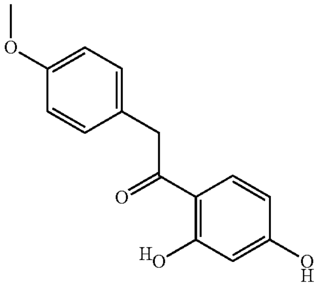 | 1-(2,4-dihydroxyphenyl)-2-(4-methoxyphenyl)ethanone | InterBioScreen Ltd STOCK5S-54694 | IBS694 |
| 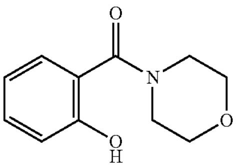 [SMILES: O=C(c1ccccc1O)N1CCOCC1] | (2-hydroxyphenyl)-morpholin-4-ylmethanone | InterBioScreen Ltd STOCK1S-59117 | IBS117 |
| 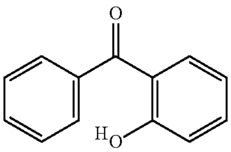 | (2-hydroxyphenyl)-phenylmethanone | Specs AE-562/43458976 | SPE976 |
| 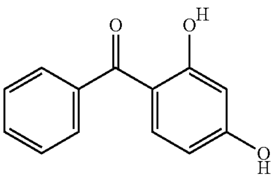 | (2,4-dihydroxyphenyl)-phenylmethanone | Specs AE-641/01968047 | SPE047 |

APPENDIX 1'-continued

| SAR Analysis Round 1 Molecules | | | |
|---|---|---|---|
| Structure | IUPAC Name | Vendor Information | Abbreviation |
| 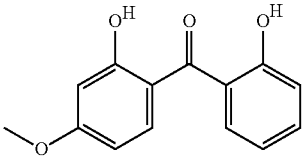 | (2-hydroxy-4-methoxyphenyl)-(2-hydroxyphenyl)methanone | AK Scientific K820 | K820 |
| 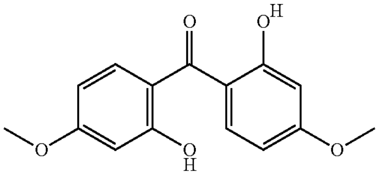 | bis(2-hydroxy-4-methoxyphenyl)methanone | AK Scientific L008 | L008 |
| 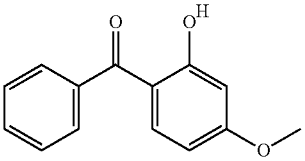 | (2-hydroxy-4-methoxyphenyl)-phenylmethanone | AK Scientific I956 | I956 |
| 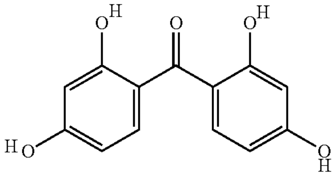 | bis(2,4-dihydroxyphenyl)methanone | AK Scientific I955 | I955 |
| 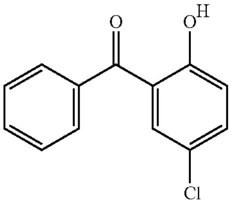 | (5-chloro-2-hydroxyphenyl)-phenylmethanone | AK Scientific O344 | O344 |

APPENDIX 2

| SAR Analysis Round 2 Molecules | | | |
|---|---|---|---|
| Structure | IUPAC Name | Vendor Information | Abbreviation |
| 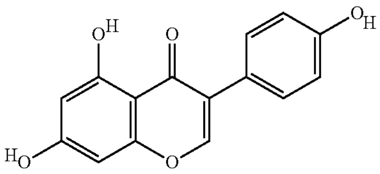 | 5,7-dihydroxy-3-(4-hydroxyphenyl)chromen-4-one | AK Scientific J10015 | AK015 |
| 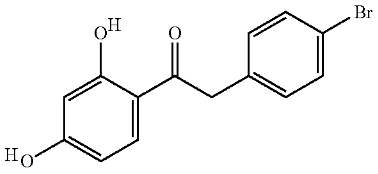 | 2-(4-bromophenyl)-1-(2,4-dihydroxyphenyl)ethanone | ChemBridge Corporation 7113606 | CB606 |

APPENDIX 2-continued

SAR Analysis Round 2 Molecules

| Structure | IUPAC Name | Vendor Information | Abbreviation |
| --- | --- | --- | --- |
| 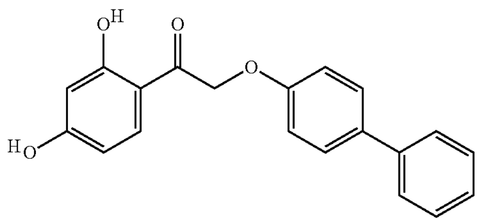 | 1-(2,4-dihydroxyphenyl)-2-(4-phenylphenoxy)ethanone | ChemBridge Corporation 6688097 | CB097 |
| 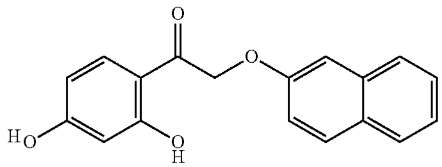 | 1-(2,4-dihydroxyphenyl)-2-naphthalen-2-yloxyethanone | ChemBridge Corporation 6686070 | CB070 |
| 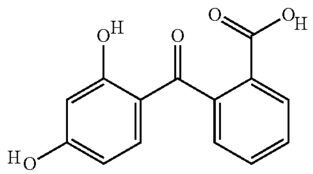 | 2-(2,4-dihydroxybenzoyl)benzoic acid | ChemBridge Corporation 5629492 | CB492 |
| 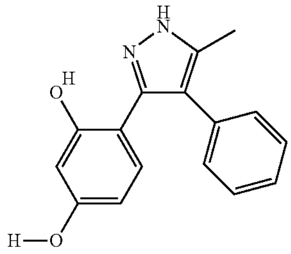 | 4-(5-methyl-4-phenyl-1H-pyrazol-3-yl)benzene-1,3-diol | InterBioScreen Ltd. STOCK4S-19358 | IBS358 |
| 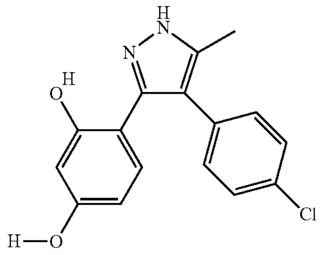 | 4-[4-(4-chlorophenyl)-5-methyl-1H-pyrazol-3-yl]benzene-1,3-diol | InterBioScreen Ltd. STOCK4S-18140 | IBS140 |
| 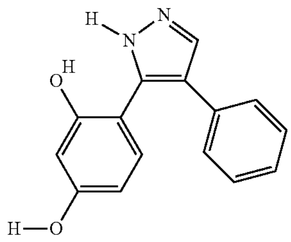 | 4-(4-phenyl-1H-pyrazol-5-yl)benzene-1,3-diol | InterBioScreen Ltd. STOCK4S-09309 | IBS309 |

APPENDIX 2-continued

SAR Analysis Round 2 Molecules

| Structure | IUPAC Name | Vendor Information | Abbreviation |
| --- | --- | --- | --- |
| 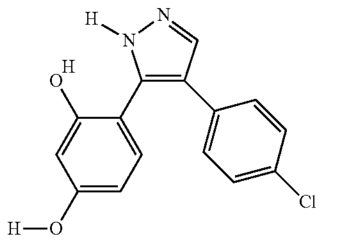 | 4-[4-(4-chlorophenyl)-1H-pyrazol-5-yl]benzene-1,3-diol | InterBioScreen Ltd. STOCK4S-25057 | IBS057 |
| 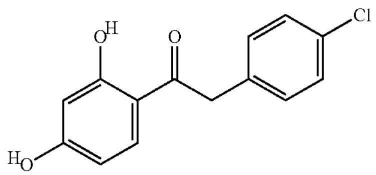 | 2-(4-chlorophenyl)-1-(2,4-dihydroxphenyl)ethanone | InterBioScreen Ltd. STOCK1S-14547 | IBS547 |
| 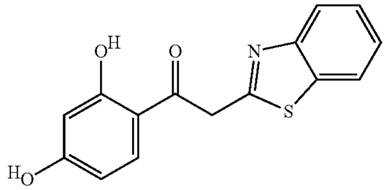 | 2-(1,3-benzothiazol-2-yl)-1-(2,4-dihydroxyphenyl)ethanone | InterBioScreen Ltd. STOCK4S-42707 | IBS707 |
| 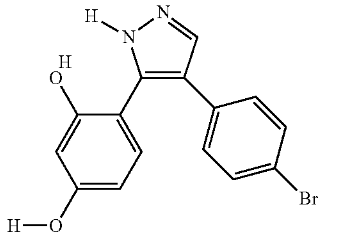 | 4-[4-(4-bromophenyl)-1H-pyrazol-5-yl]benzene-1,3-diol | InterBioScreen Ltd. STOCK3S-05374 | IBS374 |
| 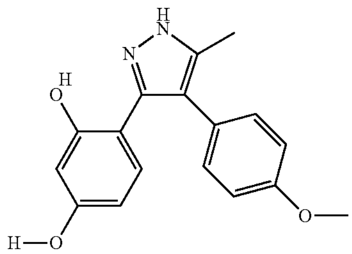 | 4-[4-(4-methoxyphenyl)-5-methyl-1H-pyrazol-3-yl]benzene-1,3-diol | InterBioScreen Ltd. STOCK3S-49162 | IBS162 |
| 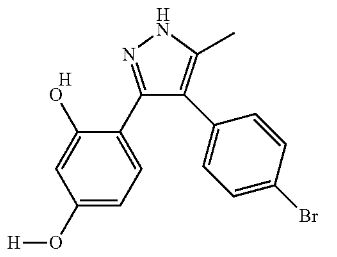 | 4-[4-(4-bromophenyl)-5-methyl-1H-pyrazol-3-yl]benzene-1,3-diol | InterBioScreen Ltd. STOCK3S-45674 | IBS674 |

APPENDIX 2-continued

SAR Analysis Round 2 Molecules

| Structure | IUPAC Name | Vendor Information | Abbreviation |
|---|---|---|---|
| 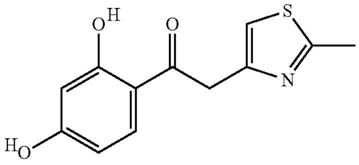 | 1-(2,4-dihydroxyphenyl)-2-(2-methyl-1,3-thiazol-4-yl)ethanone | InterBioScreen Ltd. STOCK1S-18526 | IBS526 |
| 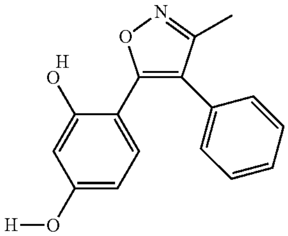 | 4-(3-methyl-4-phenyl-1,2-oxazol-5-yl)benzene-1,3-diol | InterBioScreen Ltd. STOCK6S-00308 | IBS308 |
| 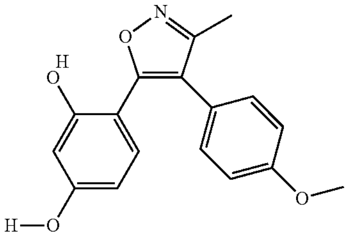 | 4-[4-(4-methoxyphenyl)-3-methyl-1,2-oxazol-5-yl]benzene-1,3-diol | InterBioScreen Ltd. STOCK5S-98672 | IBS672 |
| 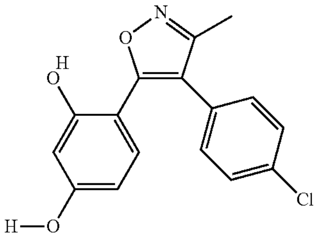 | 4-[4-(4-chlorophenyl)-3-methyl-1,2-oxazol-5-yl]benzene-1,3-diol | InterBioScreen Ltd. STOCK5S-97287 | IBS287 |
| 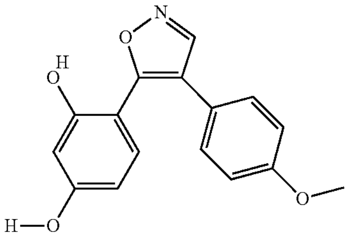 | 4-[4-(4-methoxyphenyl)-1,2-oxazol-5-yl]benzene-1,3-diol | InterBioScreen Ltd. STOCK5S-97821 | IBS821 |
| 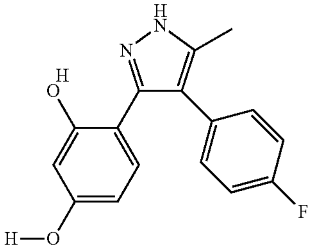 | 4-[4-(4-fluorophenyl)-5-methyl-1H-pyrazol-3-yl]benzene-1,3-diol | InterBioScreen Ltd. STOCK4S-69521 | IBS521 |

APPENDIX 2-continued

| SAR Analysis Round 2 Molecules | | | |
|---|---|---|---|
| Structure | IUPAC Name | Vendor Information | Abbreviation |
| 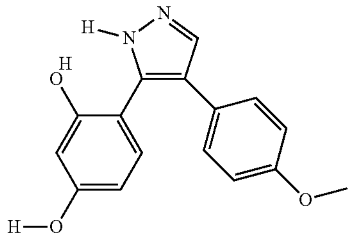 | 4-[4-(4-methoxyphenyl)-1H-pyrazol-5-yl]benzene-1,3-diol | InterBioScreen Ltd. STOCK4S-82525 | IBS525 |
| 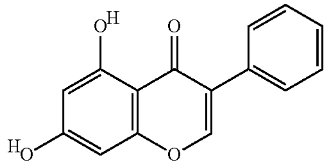 | 5,7-dihydroxy-3-phenylchromen-4-one | InterBioScreen Ltd. STOCK1N-88582 | IBS582 |

APPENDIX 2'

| SAR Analysis Round 2 Molecules | | | |
|---|---|---|---|
| Structure | IUPAC Name | Vendor Information | Abbreviation |
| 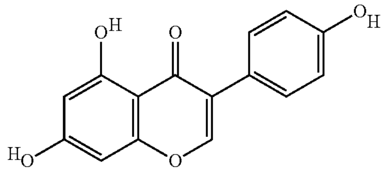 | 5,7-dihydroxy-3-(4-hydroxyphenyl)chromen-4-one | AK Scientific J10015 | AK015 |
| 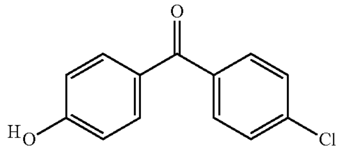 | (4-chlorophenyl)-(4-hydroxyphenyl)methanone | AK Scientific A347 | AK347 |
| 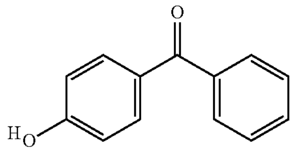 | (4-hydroxyphenyl)-phenylmethanone | AK Scientific J91321 | AK321 |
| 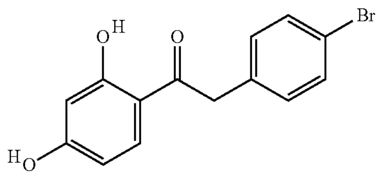 | 2-(4-bromophenyl)-1-(2,4-dihydroxyphenyl)ethanone | ChemBridge Corporation 7113606 | CB606 |

APPENDIX 2'-continued

| SAR Analysis Round 2 Molecules | | | |
|---|---|---|---|
| Structure | IUPAC Name | Vendor Information | Abbreviation |
| 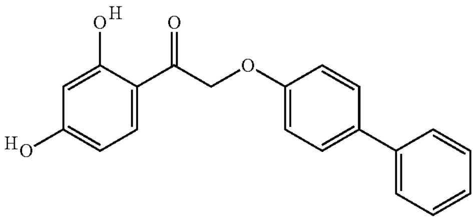 | 1-(2,4-dihydroxyphenyl)-2-(4-phenylphenoxy)ethanone | ChemBridge Corporation 6688097 | CB097 |
| 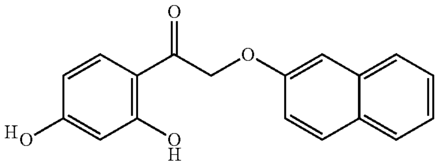 | 1-(2,4-dihydroxyphenyl)-2-naphthalen-2-yloxyethanone | ChemBridge Corporation 6686070 | CB070 |
| 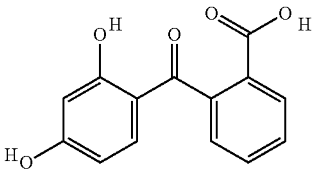 | 2-(2,4-dihydroxybenzoyl)benzoic acid | ChemBridge Corporaiton 5629492 | CB492 |
| 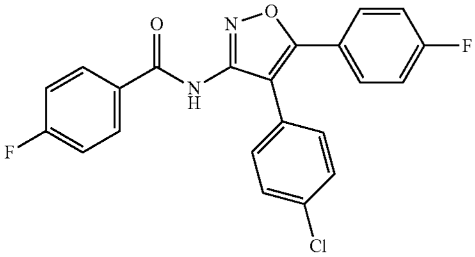 [SMILES: O=C(Nc1noc(-c2ccc(F)cc2)c1-c1ccc(Cl)cc1)c1ccc(F)cc1] | N-[4-(4-chlorophenyl)-5-(4-fluorophenyl)-1,2-oxazol-3-yl]-4-fluorobenzamide | ChemDiv, Inc. C301-7780 | CD780 |
| 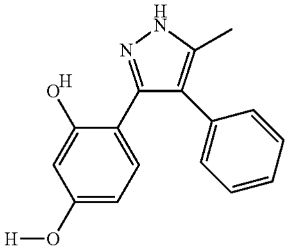 | 4-(5-methyl-4-phenyl-1H-pyrazol-3-yl)benzene-1,3-diol | InterBioScreen Ltd. STOCK4S-19358 | IBS358 |
| 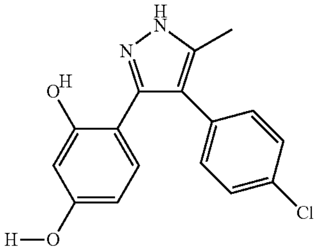 | 4-[4-(4-chlorophenyl)-5-methyl-1H-pyrazol-3-yl]benzene-1,3-diol | InterBioScreen Ltd. STOCK4S-18140 | IBS140 |

APPENDIX 2'-continued

SAR Analysis Round 2 Molecules

| Structure | IUPAC Name | Vendor Information | Abbreviation |
|---|---|---|---|
| 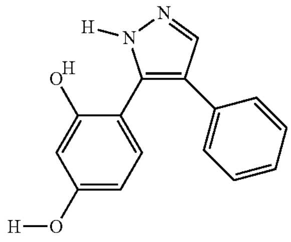 | 4-(4-phenyl-1H-pyrazol-5-yl)benzene-1,3-diol | InterBioScreen Ltd. STOCK4S-09309 | IBS309 |
| 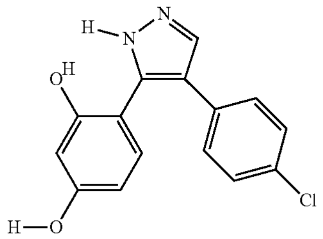 | 4-[4-(4-chlorophenyl)-1H-pyrazol-5-yl]benzene-1,3-diol | InterBioScreen Ltd. STOCK4S-25057 | IBS057 |
| 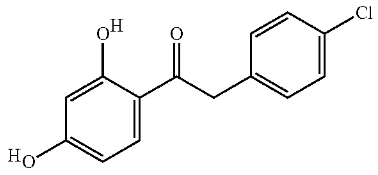 | 2-(4-chlorophenyl)-1-(2,4-dihydroxyphenyl)ethanone | InterBioScreen Ltd. STOCK1S-14547 | IBS547 |
| 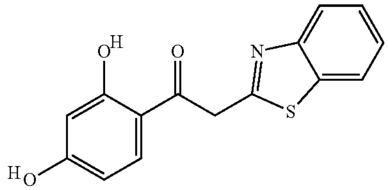 | 2-(1,3-benzothiazol-2-yl)-1-(2,4-dihydroxyphenyl)ethanone | InterBioScreen Ltd. STOCK4S-42707 | IBS707 |
| 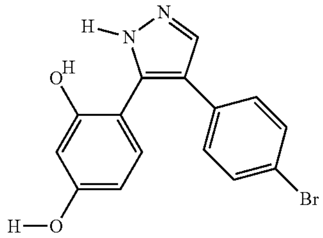 | 4-[4-(4-bromophenyl)-1H-pyrazol-5-yl]benzene-1,3-diol | InterBioScreen Ltd STOCK3S-05374 | IBS374 |
| 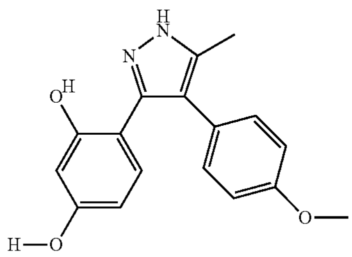 | 4-[4-(4-methoxyphenyl)-5-methyl-1H-pyrazol-3-yl]benzene-1,3-diol | InterBioScreen Ltd. STOCK3S-49162 | IBS162 |

APPENDIX 2'-continued

| SAR Analysis Round 2 Molecules | | | |
|---|---|---|---|
| Structure | IUPAC Name | Vendor Information | Abbreviation |
| 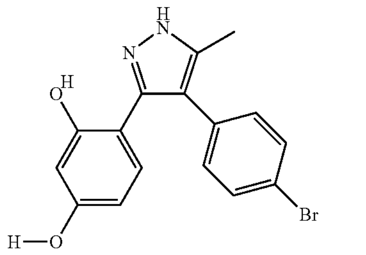 | 4-[4-(4-bromophenyl)-5-methyl-1H-pyrazol-3-yl]benzene-1,3-diol | InterBioScreen Ltd. STOCK3S-45674 | IBS674 |
| 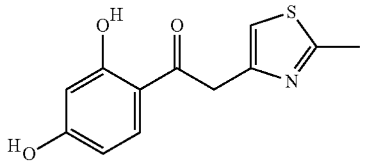 | 1-(2,4-dihydroxyphenyl)-2-(2-methyl-1,3-thiazol-4-yl)ethanone | InterBioScreen Ltd. STOCK1S-18526 | IBS526 |
| 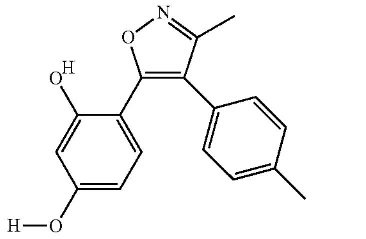 | 4-(3-methyl-4-phenyl-1,2-oxazol-5-yl)benzene-1,3-diol | InterBioScreen Ltd. STOCK6S-00308 | IBS308 |
| 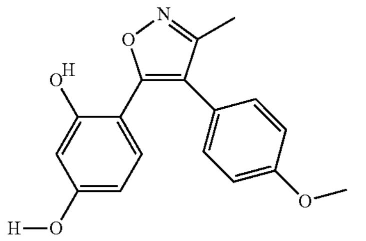 | 4-[4-(4-methoxyphenyl)-3-methyl-1,2-oxazol-5-yl]benzene-1,3-diol | InterBioScreen Ltd. STOCK5S-98672 | IBS672 |
| 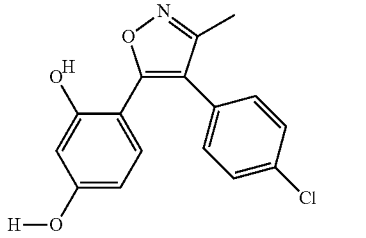 | 4-[4-(4-chlorophenyl)-3-methyl-1,2-oxazol-5-yl]benzene-1,3-diol | InterBioScreen Ltd. STOCK5S-97287 | IBS287 |
| 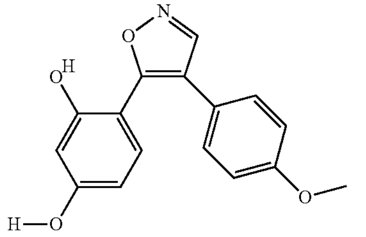 | 4-[4-(4-methoxyphenyl)-1,2-oxazol-5-yl]benzene-1,3-diol | InterBioScreen Ltd. STOCK5S-97821 | IBS821 |

APPENDIX 2'-continued

| SAR Analysis Round 2 Molecules | | | |
|---|---|---|---|
| Structure | IUPAC Name | Vendor Information | Abbreviation |
| 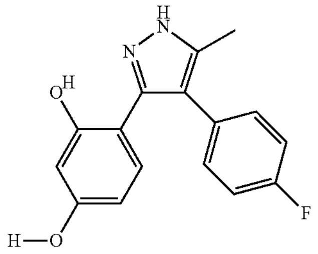 | 4-[4-(4-fluorophenyl)-5-methyl-1H-pyrazol-3-yl]benzene-1,3-diol | InterBioScreen Ltd. STOCK4S-69521 | IBS521 |
| 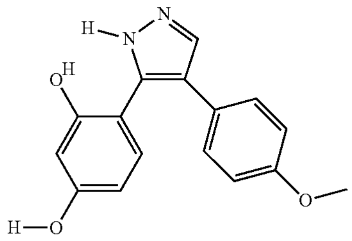 | 4-[4-(4-methoxyphenyl)-1H-pyrazol-5-yl]benzene-1,3-diol | InterBioScreen Ltd. STOCK4S-82525 | IBS525 |
| 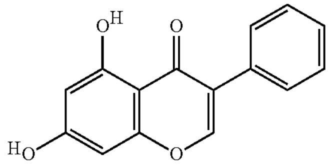 | 5,7-dihydroxy-3-phenylchromen-4-one | InterBioScreen Ltd. STOCK1N-88582 | IBS582 |
| 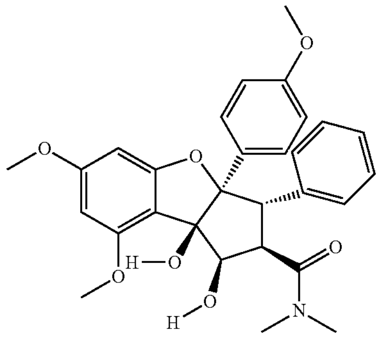 [SMILES: COc1ccc([C@@]23Oc4cc(OC)cc(OC)c4[C@@]2(O)[C@H](O)[C@H](C(=O)N(C)C)[C@H]3c2ccccc2)cc1] | (1R,2R,3S,3aR,8bS)-1,8b-dihydroxy-6,8-dimethoxy-3a-(4-methoxyphenyl)-N,N-dimethyl-3-phenyl-2,3-dihydro-1H-cyclopenta[b][1]benzofuran-2-carboxamide | MedChemExpress Europe HY-19356 | MCE356, roclagamide |

APPENDIX 3

SAR Analysis Round 3 Molecules

| Structure | IUPAC Name | Vendor Information | Abbreviation |
|---|---|---|---|
| 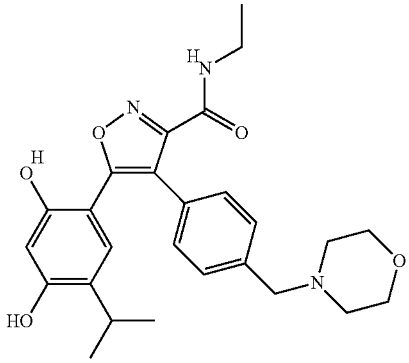 | 5-(2,4-dihydroxy-5-propan-2-ylphenyl)-N-ethyl-4-[4-(morpholin-4-ylmethyl)phenyl]-1,2-oxazole-3-carboxamide | Axon Medchem 1542 | AM542 (AUY-922) |
| 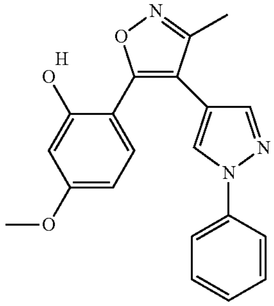 | 5-methoxy-2-[3-methyl-4-(1-phenylpyrazol-4-yl)-1,2-oxazol-5-yl]phenol | ChemBridge Corporation 6873595 | CB595 |
| 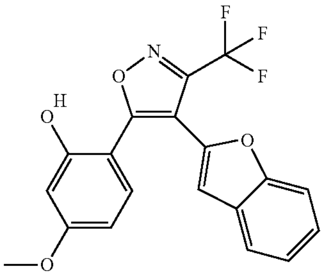 | 2-[4-(1-benzofuran-2-yl)-3-(trifluoromethyl)-1,2-oxazol-5-yl]-5-methoxyphenol | ENAMINE Ltd. Z56793271 | ENA271 |
| 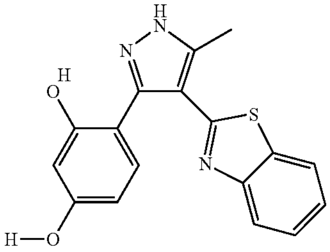 | 4-[4-(1,3-benzothiazol-2-yl)-5-methyl-1H-pyrazol-3-yl]benzene-1,3-diol | InterBioScreen Ltd. STOCK2S-77259 | IBS259 |
| 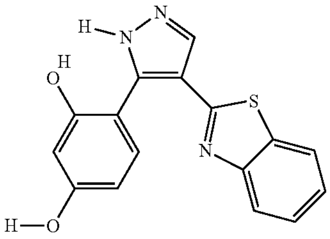 | 4-[4-(1,3-benzothiazol-2-yl)-1H-pyrazol-5-yl]benzene-1,3-diol | InterBioScreen Ltd. STOCK1S-68454 | IBS454 |

APPENDIX 3-continued

| SAR Analysis Round 3 Molecules | | | |
|---|---|---|---|
| Structure | IUPAC Name | Vendor Information | Abbreviation |
| 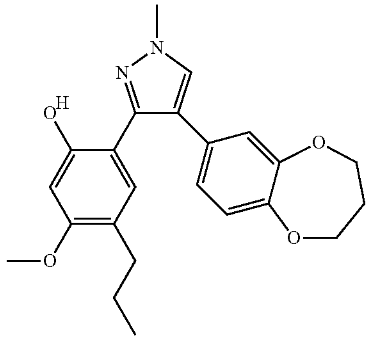 | 2-[4-(3,4-dihydro-2H-1,5-benzodioxepin-7-yl)-1-methylpyrazol-3-yl]-5-methoxy-4 -propylphenol | InterBioScreen Ltd. STOCK1N-06154 | IBS154 |
| 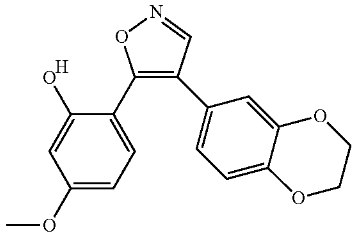 | 2-[4-(2,3-dihydro-1,4-benzodioxin-6-yl)-1,2-oxazol-5-yl]-5-methoxyphenol | InterBioScreen Ltd. STOCK1N-07078 | IBS078 |
| 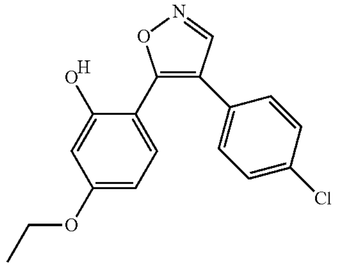 | 2-[4-(4-chlorophenyl)-1,2-oxazol-5-yl]-5-ethoxyphenol | InterBioScreen Ltd. STOCK6S-00206 | IBS206 |
| 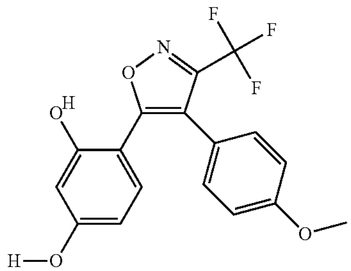 | 4-[4-(4-methoxyphenyl)-3-(trifluoromethyl)-1,2-oxazol-5-yl]benzene-1,3-diol | InterBioScreen Ltd. STOCK5S-98901 | IBS901 |
| 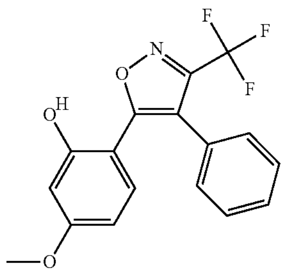 | 5-methoxy-2-[4-phenyl-3-(trifluoromethyl)-1,2-oxazol-5-yl]phenol | InterBioScreen Ltd. STOCK5S-99550 | IBS550 |

APPENDIX 3-continued

| SAR Analysis Round 3 Molecules | | | |
|---|---|---|---|
| Structure | IUPAC Name | Vendor Information | Abbreviation |
| 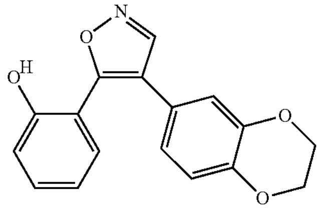 | 2-[4-(2,3-dihydro-1,4-benzodioxin-6-yl)-1,2-oxazol-5-yl]phenol | InterBioScreen Ltd. STOCK1N-01831 | IBS831 |
| 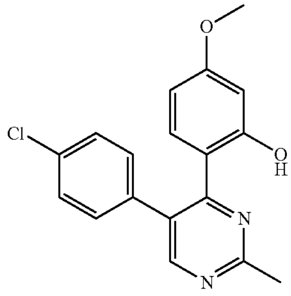 [SMILES: COc1ccc(-c2nc(C)ncc2-c2ccc(Cl)cc2)c(O)c1] | 2-[5-(4-chlorophenyl)-2-methylpyrimidin-4-yl]-5-methoxyphenol | InterBioScreen Ltd. STOCK5S-56524 | IBS524 |
| 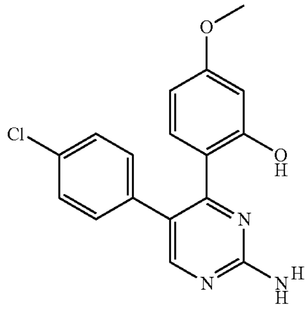 | 2-[2-amino-5-(4-chlorophenyl)pyrimidin-4-yl]-5-methoxyphenol | InterBioScreen Ltd. STOCK5S-16629 | IBS629 |
| 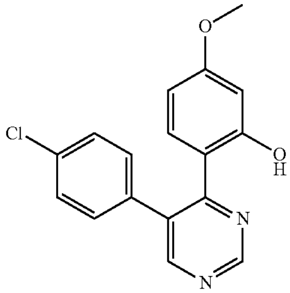 [SMILES: COc1ccc(-c2ncncc2-c2ccc(Cl)cc2)c(O)c1] | 2-[5-(4-chlorophenyl)pyridin-4-yl]-5-methoxyphenol | InterBioScreen Ltd. STOCK5S-09547 | IBS547 |
| 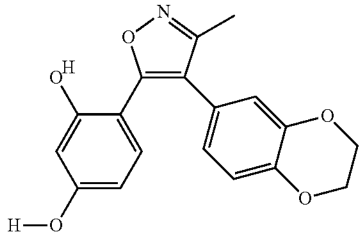 | 4-[4-(2,3-dihydro-1,4-benzodioxin-6-yl)-3-methyl-1,2-oxazol-5-yl]benzene-1,3-diol | InterBioScreen Ltd. STOCK1N-10332 | IBS332 |

APPENDIX 3-continued

SAR Analysis Round 3 Molecules

| Structure | IUPAC Name | Vendor Information | Abbreviation |
|---|---|---|---|
| 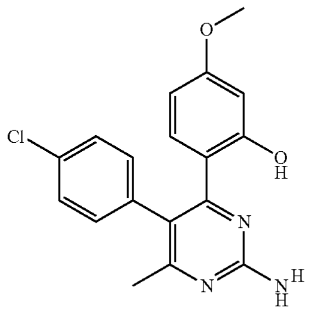 | 2-[2-amino-5-(4-chlorophenyl)-6-methylpyrimidin-4-yl]-5-methoxyphenol | InterBioScreen Ltd. STOCK5S-21266 | IBS266 |
| 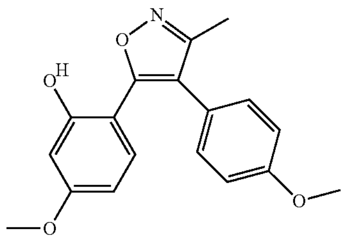 | 5-methoxy-2-[4-(4-methoxyphenyl)-3-methyl-1,2-oxazol-5-yl]phenol | InterBioScreen Ltd. STOCK5S-99516 | IBS516 |
| 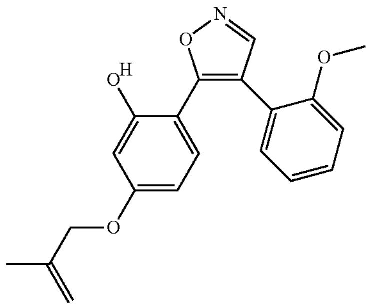 | 2-[4-(2-methoxyphenyl)-1,2-oxazol-5-yl]-5-(2-methylprop-2-enoxy)phenol | InterBioScreen Ltd. STOCK6S-01466 | IBS466 |
| 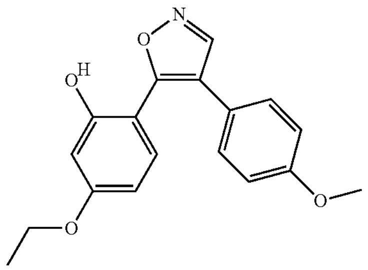 | 5-ethoxy-2-[4-(4-methoxyphenyl)-1,2-oxazol-5-yl]phenol | InterBioScreen Ltd. STOCK6S-02983 | IBS983 |
| 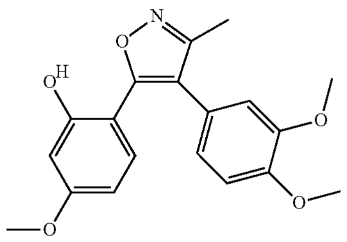 | 2-[4-(3,4-dimethoxyphenyl)-3-methyl-1,2-oxazol-5-yl]-5-methoxyphenol | InterBioScreen Ltd. STOCK6S-04304 | IBS304 |

APPENDIX 3-continued

SAR Analysis Round 3 Molecules

| Structure | IUPAC Name | Vendor Information | Abbreviation |
|---|---|---|---|
| 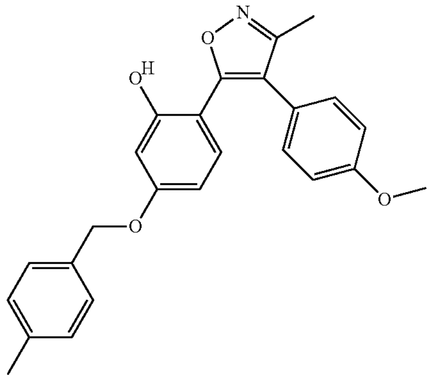 | 2-[4-(4-methoxyphenyl)-3-methyl-1,2-oxazol-5-yl]-5-[(4-methylphenyl)methoxy]phenol | InterBioScreen Ltd. STOCK6S-04330 | IBS330 |
| 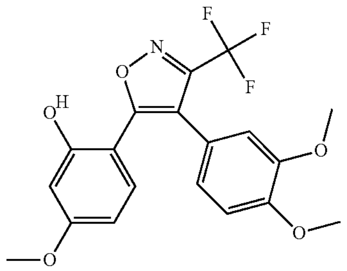 | 2-[4-(3,4-dimethoxyphenyl)-3-(trifluoromethyl)-1,2-oxazol-5-yl]-5-methoxyphenol | InterBioScreen Ltd. STOCK6S-07597 | IBS597 |
| 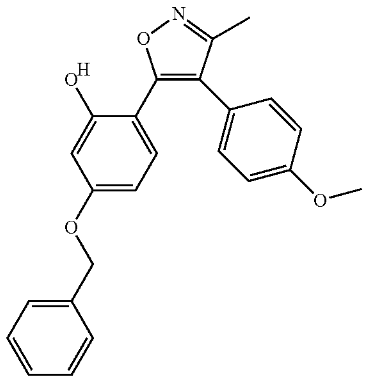 | 2-[4-(4-methoxyphenyl)-3-methyl-1,2-oxazol-5-yl]-5-phenylmethoxyphenol | InterBioScreen Ltd. STOCK6S-09992 | IBS992 |
| 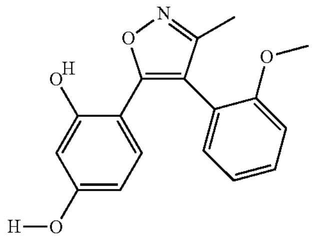 | 4-[4-(2-methoxyphenyl)-3-methyl-1,2-oxazol-5-yl]benzene-1,3-diol | InterBioScreen Ltd. STOCK6S-10451 | IBS451 |

APPENDIX 3-continued

SAR Analysis Round 3 Molecules

| Structure | IUPAC Name | Vendor Information | Abbreviation |
|---|---|---|---|
| 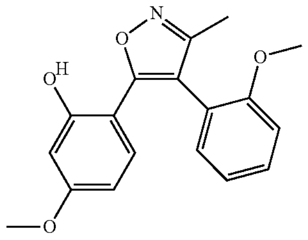 | 5-methoxy-2-[4-(2-methoxyphenyl)-3-methyl-1,2-oxazol-5-yl]phenol | InterBioScreen Ltd. STOCK6S-11060 | IBS060 |
| 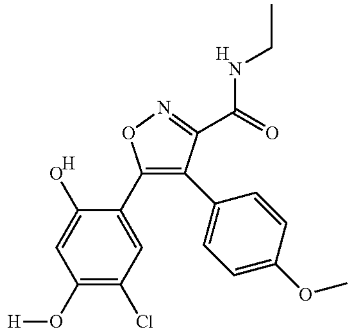 | 5-(5-chloro-2,4-dihydroxyphenyl)-N-ethyl-4-(4-methoxyphenyl)-1,2-oxazole-3-carboxamide | TargetMol T2258 | TM258 (VER-50589) |
| 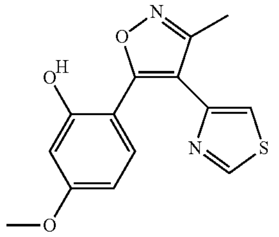 | 5-methoxy-2-[3-methyl-4-(1,3-thiazol-4-yl)-1,2-oxazol-5-yl]phenol | UkrOrgSynthesis Ltd. Stock PB56845823 | UOS823 |

APPENDIX 4

Additional Molecules

| Structure | IUPAC Name | Vendor Information | Abbreviation |
|---|---|---|---|
| 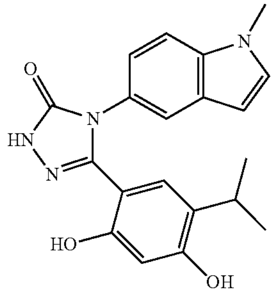 [SMILES: CC(C)c1cc(-c2n[nH]c(=O)n2-c2ccc3c(ccn3C)c2)c(O)cc1O] | 3-(2,4-dihydroxy-5-propan-2-ylphenyl)-4-(1-methylindol-5-yl)-1H-1,2,4-triazol-5-one | Selleck Chem S1159 | STA-9090 |

APPENDIX 4-continued

| Additional Molecules | | | |
|---|---|---|---|
| Structure | IUPAC Name | Vendor Information | Abbreviation |
| 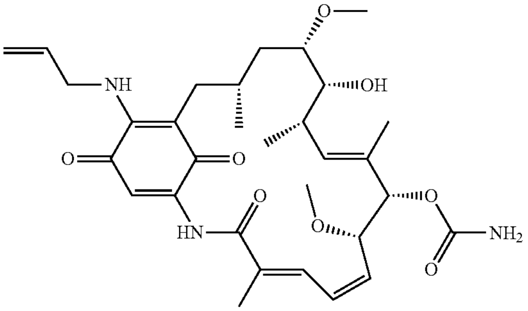 [SMILES: C=CCNC1=C2C[C@@H](C)C[C@H](OC)[C@H](O)[C@@H](C)/C=C(\C)[C@H](OC(N)=O)[C@@H](OC)/C=C\C=C(/C)C(=O)NC(=CC1=O)C2=O] | [(4E,6Z,8S,9S,10E,12S,13R,14S,16R)-13-hydroxy-8,14-dimethoxy-4,10,12,16-tetramethyl-3,20,22-trioxo-19-(prop-2-enylamino)-2-azabicyclo[16.3.1]docosa-1(21),4,6,10,18-pentaen-9-yl] carbamate | Selleck Chem S1141 | 17-AAG |
| 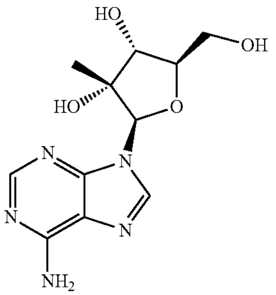 [SMILES: C[C@@]1(O)[C@H](O)[C@@H](CO)O[C@H]1n1cnc2c(N)ncnc21] | (2R,3R,4R,5R)-2-(6-aminopurin-9-yl)-5-(hydroxymethyl)-3-methyloxolane-3,4-diol | Carbosynth 15397-12-3 | 2'CMA |

Generation of liver chimeric mice. Cryopreserved human adult primary hepatocytes were obtained from Bioreclamation (Westbury, NY) and washed with high glucose DMEM. Using isoflurane anesthesia, human cell suspensions were injected intrasplenically into female fah−/−NOD rag1−/−il2rgnull (FNRG) mice that were generated by backcrossing of the fah−/− allele to NOD rag1−/−il2rgnull (NRG) animals obtained from Jackson Labs as described previously. Approximately $1\times10^6$ human adult hepatocytes were transplanted per mouse using protocols previously established in the Ploss lab. Starting on the day of transplantation mice were cycled off the drug NTBC (Yecuris Inc., Tualatin, OR). All mice were maintained at the Laboratory Animal Resource Center at Princeton University.

All animal experiments described in this study were performed in accordance with protocols (number 1930-19) that were reviewed and approved by the Institutional Animal Care and Use and Committee of Princeton University.

Assessment of engraftment by human albumin ELISA. Levels of human albumin in mouse serum were quantified by ELISA; 96-well flat-bottomed plates (Nunc, Thermo Fischer Scientific, Witham, MA) were coated with goat anti-human albumin antibody (1:500, Bethel) in coating buffer (1.59 g $Na_2CO_3$, 2.93 g $NaHCO_3$, 1 L $dH_2O$, pH=9.6) for 1 hour at 37° C. The plates were washed four times with wash buffer (0.05% Tween 20 (Sigma Aldrich, St. Louis, MO) in 1×PBS) then incubated with superblock buffer (Fisher Scientific, Hampton NH) for 1 hour at 37° C. Plates were washed twice. Human serum albumin (Sigma Aldrich, St. Louis MO) was diluted to 1 μg/ml in sample diluent (10% Superblock, 90% wash buffer), then serially diluted 1:2 in 135 μl sample diluent to establish an albumin standard. Mouse serum (5 μl) was used for a 1:10 serial dilution in 135 μl sample diluent. The coated plates were incubated for 1 hour at 37° C., then washed three times. Mouse anti-human albumin (50 μl, 1:2000 in sample diluent, Abcam, Cambridge, UK) was added and plates were incubated for 2 hours at 37° C. Plates were washed four times, and 50 μl of goat anti-mouse-HRP (1:10,000 in sample diluent, LifeTechnologies, Carlsbad, CA) was added and incubated for 1 hour at 37° C. Plates were washed six times. TMB (100 μl) substrate (Sigma Aldrich, St. Louis, MO) was added and the reaction was stopped with 12.5 μl of 2N $H_2SO_4$. Absorbance was read at 450λ on the BertholdTech TriStar (Bad Wildbad, Germany).

Measurement of HEV titers in stool. The mice were separated into individual cages for approximately 15-30 min. Stool pellets were collected from the cages using sterile forceps. The mice were returned to their original cages. Stool samples were either kept on ice and analyzed immediately or kept on ice and transferred to −80° C. until analysis. The Nucleospin RNA Stool kit (TakaraBio USA, Mountain View, CA) was used to extract RNA from the samples. A spiked sample with 1.301E9 copies of Kc1p6 RNA was included as a control for extraction efficiency.

RT-qPCR: The QuantaQ ToughMix RTqPCR kit (QuantaBio, Beverly, MA) was used, with 10 μL reaction volumes.

REFERENCES

[1] Debing Y, Ramière C, Dallmeier K, Piorkowski G, Trabaud M A, Lebossé F, et al. Hepatitis E virus mutations associated with ribavirin treatment failure result in altered viral fitness and ribavirin sensitivity. J Hepatol 2016; 65:499-508.

[2] Lozano R, Naghavi M, Foreman K, Lim S, Shibuya K, Aboyans V, et al. Global and regional mortality from 235 causes of death for 20 age groups in 1990 and 2010: a systematic analysis for the Global Burden of Disease Study 2010. Lancet 2012; 380:2095-2128.

[3] Rein D B, Stevens G A, Theaker J, Wittenborn J S, Wiersma S T. The global burden of hepatitis E virus genotypes 1 and 2 in 2005. Hepatology 2012; 55:988-997.

[4] Asia WHOROfS-E. Viral Hepatitis in the WHO South-East Asia Region. New Delhi, India: World Health Organization; 2011.

[5] Kumar A, Beniwal M, Kar P, Sharma J B, Murthy N S. Hepatitis E in pregnancy. Int J Gynaecol Obstet 2004; 85:240-244.

[6] Tsega E, Krawczynski K, Hansson B G, Nordenfelt E. Hepatitis E virus infection in pregnancy in Ethiopia. Ethiop Med J 1993; 31:173-181.

[7] Gerolami R, Moal V, Colson P. Chronic hepatitis E with cirrhosis in a kidney-transplant recipient. N Engl J Med 2008; 358:859-860.

[8] Kamar N, Selves J, Mansuy J M, Ouezzani L, Peron J M, Guitard J, et al. Hepatitis E virus and chronic hepatitis in organ-transplant recipients. N Engl J Med 2008; 358:811-817.

[9] Kamar N, Lhomme S, Abravanel F, Marion O, Peron J M, Alric L, et al. Treatment of HEV Infection in Patients with a Solid-Organ Transplant and Chronic Hepatitis. Viruses 2016; 8.

[10] Debing Y, Gisa A, Dallmeier K, Pischke S, Bremer B, Manns M, et al. A mutation in the hepatitis E virus RNA polymerase promotes its replication and associates with ribavirin treatment failure in organ transplant recipients. Gastroenterology 2014; 147:1008-1011.e1007; quiz e1015-1006.

[11] Khuroo M S. Discovery of hepatitis E: the epidemic non-A, non-B hepatitis 30 years down the memory lane. Virus Res 2011; 161:3-14.

[12] Khuroo M S, Khuroo N S. Hepatitis E: Discovery, global impact, control and cure. World J Gastroenterol 2016; 22:7030-7045.

[13] Tam A W, Smith M M, Guerra M E, Huang C C, Bradley D W, Fry K E, et al. Hepatitis E virus (HEV): molecular cloning and sequencing of the full-length viral genome. Virology 1991; 185:120-131.

[14] Fry K E, Tam A W, Smith M M, Kim J P, Luk K C, Young L M, et al. Hepatitis E virus (HEV): strain variation in the nonstructural gene region encoding consensus motifs for an RNA-dependent RNA polymerase and an ATP/GTP binding site. Virus Genes 1992; 6:173-185.

[15] Rozanov M N, Koonin E V, Gorbalenya A E. Conservation of the putative methyltransferase domain: a hallmark of the 'Sindbis-like' supergroup of positive-strand RNA viruses. J Gen Virol 1992; 73 (Pt 8):2129-2134.

[16] Magden J, Takeda N, Li T, Auvinen P, Ahola T, Miyamura T, et al. Virus-specific mRNA capping enzyme encoded by hepatitis E virus. J Virol 2001; 75:6249-6255.

[17] Graff J, Torian U, Nguyen H, Emerson S U. A bicistronic subgenomic mRNA encodes both the ORF2 and ORF3 proteins of hepatitis E virus. J Virol 2006; 80:5919-5926.

[18] Ding Q, Heller B, Capuccino J M, Song B, Nimgaonkar I, Hrebikova G, et al. Hepatitis E virus ORF3 is a functional ion channel required for release of infectious particles. Proc Natl Acad Sci USA 2017; 114:1147-1152.

[19] Jameel S, Zafrullah M, Ozdener M H, Panda S K. Expression in animal cells and characterization of the hepatitis E virus structural proteins. J Virol 1996; 70:207-216.

[20] Varma S P, Kumar A, Kapur N, Durgapal H, Acharya S K, Panda S K. Hepatitis E virus replication involves alternating negative- and positive-sense RNA synthesis. J Gen Virol 2011; 92:572-581.

[21] Meng X J. Expanding Host Range and Cross-Species Infection of Hepatitis E Virus. PLoS Pathog 2016; 12:e1005695.

[22] Colson P, Borentain P, Queyriaux B, Kaba M, Moal V, Gallian P, et al. Pig liver sausage as a source of hepatitis E virus transmission to humans. J Infect Dis 2010; 202:825-834.

[23] Lewis H C, Wichmann O, Duizer E. Transmission routes and risk factors for autochthonous hepatitis E virus infection in Europe: a systematic review. Epidemiol Infect 2010; 138:145-166.

[24] Miyamura T. Hepatitis E virus infection in developed countries. Virus Res 2011; 161:40-46.

[25] Kumar S, Subhadra S, Singh B, Panda B K. Hepatitis E virus: the current scenario. Int J Infect Dis 2013; 17:e228-233.

[26] Navaneethan U, Al Mohajer M, Shata M T. Hepatitis E and pregnancy: understanding the pathogenesis. Liver Int 2008; 28:1190-1199.

[27] Perez-Gracía M T, Suay-Garcia B, Mateos-Lindemann M L. Hepatitis E and pregnancy: current state. Rev Med Virol 2017; 27:e1929.

[28] Pischke S, Wedemeyer H. Hepatitis E virus infection: multiple faces of an underestimated problem. J Hepatol 2013; 58:1045-1046.

[29] Colson P, Dhiver C, Poizot-Martin I, Tamalet C, Gérolami R. Acute and chronic hepatitis E in patients infected with human immunodeficiency virus. J Viral Hepat 2011; 18:227-228.

[30] Dalton H R, Bendall R P, Keane F E, Tedder R S, Ijaz S. Persistent carriage of hepatitis E virus in patients with HIV infection. N Engl J Med 2009; 361:1025-1027.

[31] Fujiwara S, Yokokawa Y, Morino K, Hayasaka K, Kawabata M, Shimizu T. Chronic hepatitis E: a review of the literature. J Viral Hepat 2014; 21:78-89.

[32] Kamar N, Abravanel F, Selves J, Garrouste C, Esposito L, Lavayssière L, et al. Influence of immunosuppressive therapy on the natural history of genotype 3 hepatitis-E virus infection after organ transplantation. Transplantation 2010; 89:353-360.

[33] Kamar N, Rostaing L, Abravanel F, Garrouste C, Lhomme S, Esposito L, et al. Ribavirin therapy inhibits viral replication on patients with chronic hepatitis e virus infection. Gastroenterology 2010; 139:1612-1618.

[34] Kamar N, Garrouste C, Haagsma E B, Garrigue V, Pischke S, Chauvet C, et al. Factors associated with chronic hepatitis in patients with hepatitis E virus infection who have received solid organ transplants. Gastroenterology 2011; 140:1481-1489.

[35] Kamar N, Mallet V, Izopet J. Ribavirin for chronic hepatitis E virus infection. N Engl J Med 2014; 370:2447-2448.

[36] Haagsma E B, Riezebos-Brilman A, van den Berg A P, Porte R J, Niesters H G. Treatment of chronic hepatitis E in liver transplant recipients with pegylated interferon alpha-2b. Liver Transpl 2010; 16:474-477.

[37] Kamar N, Abravanel F, Garrouste C, Cardeau-Desangles I, Mansuy J M, Weclawiak H, et al. Three-month pegylated interferon-alpha-2a therapy for chronic hepatitis E virus infection in a haemodialysis patient. Nephrol Dial Transplant 2010; 25:2792-2795.

[38] Behrendt P, Steinmann E, Manns M P, Wedemeyer H. The impact of hepatitis E in the liver transplant setting. J Hepatol 2014; 61:1418-1429.

[39] Todt D, Meister T L, Steinmann E. Hepatitis E virus treatment and ribavirin therapy: viral mechanisms of nonresponse. Curr Opin Virol 2018; 32:80-87.

[40] van der Valk M, Zaaijer H L, Kater A P, Schinkel J. Sofosbuvir shows antiviral activity in a patient with chronic hepatitis E virus infection. J Hepatol 2017; 66:242-243.

[41] van Wezel E M, de Bruijne J, Damman K, Bijmolen M, van den Berg A P, Verschuuren E A M, et al. Sofosbuvir Add-on to Ribavirin Treatment for Chronic Hepatitis E Virus Infection in Solid Organ Transplant Recipients Does Not Result in Sustained Virological Response. Open Forum Infect Dis 2019; 6.

[42] Drinane M, Jing Wang X, Watt K. Sofosbuvir and Ribavirin Eradication of Refractory Hepatitis E in an Immunosuppressed Kidney Transplant Recipient. Hepatology 2019; 69:2297-2299.

[43] Fraga M, Gouttenoire J, Sahli R, Chtioui H, Marcu C, Pascual M, et al. Sofosbuvir add-on to ribavirin for chronic hepatitis E in a cirrhotic liver transplant recipient: a case report. BMC Gastroenterol 2019; 19:76.

[44] Malcolm B A, Liu R, Lahser F, Agrawal S, Belanger B, Butkiewicz N, et al. SCH 503034, a mechanism-based inhibitor of hepatitis C virus NS3 protease, suppresses polyprotein maturation and enhances the antiviral activity of alpha interferon in replicon cells. Antimicrob Agents Chemother 2006; 50:1013-1020.

[45] Lin T I, Lenz O, Fanning G, Verbinnen T, Delouvroy F, Scholliers A, et al. In vitro activity and preclinical profile of TMC435350, a potent hepatitis C virus protease inhibitor. Antimicrob Agents Chemother 2009; 53:1377-1385.

[46] Stedman C. Sofosbuvir, a NS5B polymerase inhibitor in the treatment of hepatitis C: a review of its clinical potential. Therap Adv Gastroenterol 2014; 7:131-140.

[47] Benhamou Y, Tubiana R, Thibault V. Tenofovir disoproxil fumarate in patients with HIV and lamivudine-resistant hepatitis B virus. N Engl J Med 2003; 348:177-178.

[48] Shukla P, Nguyen H T, Torian U, Engle R E, Faulk K, Dalton H R, et al. Cross-species infections of cultured cells by hepatitis E virus and discovery of an infectious virus-host recombinant. Proc Natl Acad Sci USA 2011; 108:2438-2443.

[49] Todt D, Moeller N, Praditya D, Kinast V, Friesland M, Engelmann M, et al. The natural compound silvestrol inhibits hepatitis E virus (HEV) replication in vitro and in vivo. Antiviral Res 2018; 157:151-158.

[50] Sidwell R W, Huffman J H, Khare G P, Allen L B, Witkowski J T, Robins R K. Broad-spectrum antiviral activity of Virazole: 1-beta-D-ribofuranosyl-1,2,4-triazole-3-carboxamide. Science 1972; 177:705-706.

[51] Tsarev S A, Emerson S U, Reyes G R, Tsareva T S, Legters L J, Malik I A, et al. Characterization of a prototype strain of hepatitis E virus. Proc Natl Acad Sci USA 1992; 89:559-563.

[52] Ding Q, Nimgaonkar I, Archer N F, Bram Y, Heller B, Schwartz R E, et al. Identification of the Intragenomic Promoter Controlling Hepatitis E Virus Subgenomic RNA Transcription. MBio 2018; 9.

[53] Marukian S, Jones C T, Andrus L, Evans M J, Ritola K D, Charles E D, et al. Cell culture-produced hepatitis C virus does not infect peripheral blood mononuclear cells. Hepatology 2008; 48:1843-1850.

[54] Savitski M M, Reinhard F B, Franken H, Werner T, Savitski M F, Eberhard D, et al. Tracking cancer drugs in living cells by thermal profiling of the proteome. Science 2014; 346:1255784.

[55] Becher I, Werner T, Doce C, Zaal E A, Tögel I, Khan C A, et al. Thermal profiling reveals phenylalanine hydroxylase as an off-target of panobinostat. Nat Chem Biol 2016; 12:908-910.

[56] Geller R, Taguwa S, Frydman J. Broad action of Hsp90 as a host chaperone required for viral replication. Biochim Biophys Acta 2012; 1823:698-706.

[57] Schopf F H, Biebl M M, Buchner J. The HSP90 chaperone machinery. Nat Rev Mol Cell Biol 2017; 18:345-360.

[58] Burch A D, Weller S K. Nuclear sequestration of cellular chaperone and proteasomal machinery during herpes simplex virus type 1 infection. J Virol 2004; 78:7175-7185.

[59] Miyata Y, Yahara I. p53-independent association between SV40 large T antigen and the major cytosolic heat shock protein, HSP90. Oncogene 2000; 19:1477-1484.

[60] Ujino S, Yamaguchi S, Shimotohno K, Takaku H. Heat-shock protein 90 is essential for stabilization of the hepatitis C virus nonstructural protein NS3. J Biol Chem 2009; 284:6841-6846.

[61] Waxman L, Whitney M, Pollok B A, Kuo L C, Darke P L. Host cell factor requirement for hepatitis C virus enzyme maturation. Proc Natl Acad Sci USA 2001; 98:13931-13935.

[62] Zheng Z Z, Miao J, Zhao M, Tang M, Yeo A E, Yu H, et al. Role of heat-shock protein 90 in hepatitis E virus capsid trafficking. J Gen Virol 2010; 91:1728-1736.

[63] Eccles S A, Massey A, Raynaud F I, Sharp S Y, Box G, Valenti M, et al. NVP-AUY922: a novel heat shock protein 90 inhibitor active against xenograft tumor growth, angiogenesis, and metastasis. Cancer Res 2008; 68:2850-2860.

[64] Sharp S Y, Prodromou C, Boxall K, Powers M V, Holmes J L, Box G, et al. Inhibition of the heat shock protein 90 molecular chaperone in vitro and in vivo by novel, synthetic, potent resorcinylic pyrazole/isoxazole amide analogues. Mol Cancer Ther 2007; 6:1198-1211.

[65] Lin T Y, Bear M, Du Z, Foley K P, Ying W, Barsoum J, et al. The novel HSP90 inhibitor STA-9090 exhibits activity against Kit-dependent and -independent malignant mast cell tumors. Exp Hematol 2008; 36:1266-1277.

[66] Schulte T W, Neckers L M. The benzoquinone ansamycin 17-allylamino-17-demethoxygeldanamycin binds to HSP90 and shares important biologic activities with geldanamycin. Cancer Chemother Pharmacol 1998; 42:273-279.

[67] van de Garde M D, Pas S D, van der Net G, de Man R A, Osterhaus A D, Haagmans B L, et al. Hepatitis E Virus (HEV) Genotype 3 Infection of Human Liver Chimeric Mice as a Model for Chronic HEV Infection. J Virol 2016; 90:4394-4401.

[68] Allweiss L, Gass S, Giersch K, Groth A, Kah J, Volz T, et al. Human liver chimeric mice as a new model of chronic hepatitis E virus infection and preclinical drug evaluation. J Hepatol 2016; 64:1033-1040.

[69] Sayed I M, Verhoye L, Cocquerel L, Abravanel F, Foquet L, Montpellier C, et al. Study of hepatitis E virus infection of genotype 1 and 3 in mice with humanised liver. Gut 2017; 66:920-929.

[70] Vaughan A M, Mikolajczak S A, Wilson E M, Grompe M, Kaushansky A, Camargo N, et al. Complete *Plasmodium falciparum* liver-stage development in liver-chimeric mice. J Clin Invest 2012; 122:3618-3628.

[71] de Jong Y P, Dorner M, Mommersteeg M C, Xiao J W, Balazs A B, Robbins J B, et al. Broadly neutralizing antibodies abrogate established hepatitis C virus infection. Sci Transl Med 2014; 6:254ra129.

[72] Scull M A, Shi C, de Jong Y P, Gerold G, Ries M, von Schaewen M, et al. Hepatitis C virus infects rhesus macaque hepatocytes and simianized mice. Hepatology 2015; 62:57-67.

[73] Winer B Y, Huang T, Low B E, Avery C, Pais M A, Hrebikova G, et al. Recapitulation of treatment response patterns in a novel humanized mouse model for chronic hepatitis B virus infection. Virology 2017; 502:63-72.

[74] Dragovic S M, Agunbiade T A, Freudzon M, Yang J, Hastings A K, Schleicher T R, et al. Immunization with AgTRIO, a Protein in Anopheles Saliva, Contributes to Protection against *Plasmodium* Infection in Mice. Cell Host Microbe 2018; 23:523-535.e525.

[75] He M Y, Xu S B, Qu Z H, Guo Y M, Liu X C, Cong X X, et al. Hsp90P interacts with MDM2 to suppress p53-dependent senescence during skeletal muscle regeneration. Aging Cell 2019; 18:e13003.

[76] Mbofung R M, McKenzie J A, Malu S, Zhang M, Peng W, Liu C, et al. HSP90 inhibition enhances cancer immunotherapy by upregulating interferon response genes. Nat Commun 2017; 8:451.

[77] Mateus A, Maatta T A, Savitski M M. Thermal proteome profiling: unbiased assessment of protein state through heat-induced stability changes. Proteome Sci 2016; 15:13.

[78] Miyata Y, Nakamoto H, Neckers L. The therapeutic target Hsp90 and cancer hallmarks. Curr Pharm Des 2013; 19:347-365.

[79] Koonin E V, Gorbalenya A E, Purdy M A, Rozanov M N, Reyes G R, Bradley D W. Computer-assisted assignment of functional domains in the nonstructural polyprotein of hepatitis E virus: delineation of an additional group of positive-strand RNA plant and animal viruses. Proc Natl Acad Sci USA 1992; 89:8259-8263.

[80] Yuno A, Lee M J, Lee S, Tomita Y, Rekhtman D, Moore B, et al. Clinical Evaluation and Biomarker Profiling of Hsp90 Inhibitors. Methods Mol Biol 2018; 1709:423-441.

[81] Sridharan S, Kurzawa N, Werner T, Gunthner I, Helm D, Huber W, et al. Proteome-wide solubility and thermal stability profiling reveals distinct regulatory roles for ATP. Nat Commun 2019; 10:1155.

[82] Mateus A, Bobonis J, Kurzawa N, Stein F, Helm D, Hevler J, et al. Thermal proteome profiling in bacteria: probing protein state. Mol Syst Biol 2018; 14:e8242.

[83] Hughes C S, Foehr S, Garfield D A, Furlong E E, Steinmetz L M, Krijgsveld J. Ultrasensitive proteome analysis using paramagnetic bead technology. Mol Syst Biol 2014; 10:757.

[84] Hughes C S, Moggridge S, Müller T, Sorensen P H, Morin G B, Krijgsveld J. Single-pot, solid-phase-enhanced sample preparation for proteomics experiments. Nat Protoc 2019; 14:68-85.

[85] Becher I, Andres-Pons A, Romanov N, Stein F, Schramm M, Baudin F, et al. Pervasive Protein Thermal Stability Variation during the Cell Cycle. Cell 2018; 173:1495-1507.e1418.

[86] Franken H, Mathieson T, Childs D, Sweetman G M, Werner T, Tögel I, et al. Thermal proteome profiling for unbiased identification of direct and indirect drug targets using multiplexed quantitative mass spectrometry. Nat Protoc 2015; 10:1567-1593.

[87] Chung H Y, Gu M, Buehler E, MacDonald M R, Rice C M. Seed sequence-matched controls reveal limitations of small interfering RNA knockdown in functional and structural studies of hepatitis C virus NS5A-MOBKL1B interaction. J Virol 2014; 88:11022-11033.

[88] Rueden C T, Schindelin J, Hiner M C, DeZonia B E, Walter A E, Arena E T, et al. ImageJ2: ImageJ for the next generation of scientific image data. BMC Bioinformatics 2017; 18:529.

[89] von Schaewen M, Hrebikova G, Ploss A. Generation of Human Liver Chimeric Mice for the Study of Human Hepatotropic Pathogens. Methods Mol Biol 2016; 1438: 79-101.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. A method of inhibiting replication of a virus, comprising contacting a cell infected with the virus with a compound represented by the following structural formula:

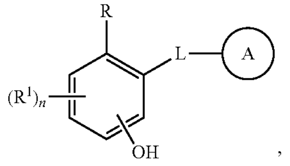

or a pharmaceutically acceptable salt thereof, wherein:

Ring A is aryl or heteroaryl, and is optionally substituted with one or more substituents independently selected from halo, hydroxy, alkyl, haloalkyl, alkoxy, haloalkoxy, $-(CH_2)_{0-2}$-aryl, $-(CH_2)_{0-2}$-heteroaryl, $-(CH_2)_{0-2}$-cycloalkyl, or $-(CH_2)_{0-2}$-heterocyclyl, carboxy or $-O(CH_2)_mO-$;

m is 1, 2, 3, 4 or 5;

L is $-C(O)(CH_2)_p-$, $-C(O)(CH_2)_p-O-$ or heteroarylene, wherein p is 0, 1 or 2, and R is hydrogen, halo, hydroxy, alkyl, haloalkyl, alkoxy, haloalkoxy, alkenoxy, alkynoxy, $-(CH_2)_{0-2}$-aryl, or $-(CH_2)_{0-2}$-heteroaryl, and wherein heteroarylene is monocylic and does not form a fused ring with an adjacent ring in the compound;

$R^1$ is halo, hydroxy, alkyl, haloalkyl, alkoxy, haloalkoxy, alkenoxy, alkynoxy, $-(CH_2)_{0-2}$-aryl, or $-(CH_2)_{0-2}$-heteroaryl; and n is 0, 1, 2 or 3, wherein the aryl and heteroaryl of R and $R^1$, and the heteroarylene of L are each optionally and independently substituted with one or more substituents selected from halo, alkyl, haloalkyl, amino, alkylamino, dialkylamino or carboxamido.

2. The method of claim 1, wherein the virus is a positive-sense, single-stranded RNA virus.

3. The method of claim 2, wherein the virus is a flavivirus.

4. The method of claim 1, wherein the virus is a hepatitis E virus (HEV), hepatitis C virus (HCV) or yellow fever virus (YFV).

5. The method of claim 1, wherein the compound is isocotoin, or a pharmaceutically acceptable salt thereof.

6. The method of claim 1, wherein the compound is represented by the following structural formula:

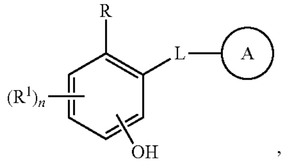

or a pharmaceutically acceptable salt thereof.

7. The method of claim 1, wherein L is $(C_5-C_6)$ heteroarylene.

8. The method of claim 7, wherein L is oxazolylene, pyrazolylene, pyrimidinylene or triazolylene.

9. The method of claim 1, wherein the heteroarylene of L is optionally substituted with one substituent selected from halo, alkyl, haloalkyl, amino, alkylamino, dialkylamino or carboxamido.

10. The method of claim 1, wherein Ring A is phenyl.

11. The method of claim 1, wherein Ring A is heteroaryl.

12. The method of claim 11, wherein Ring A is indolyl, pyrazolyl, benzofuranyl, benzothiazolyl, or thiazolyl.

13. The method of claim 1, wherein the compound is represented by the following structural formula:

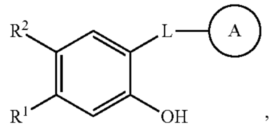

or a pharmaceutically acceptable salt thereof, wherein:

$R^2$ is hydrogen, halo, hydroxy, alkyl, haloalkyl, alkoxy, haloalkoxy, alkenoxy, alkynoxy, $-(CH_2)_{0-2}$-aryl, or $-(CH_2)_{0-2}$-heteroaryl.

14. The method of claim 13, wherein $R^1$ is hydroxy, alkoxy, haloalkoxy, alkenoxy or alkynoxy.

15. The method of claim 13, wherein $R^2$ is hydrogen, halo, alkyl or haloalkyl.

16. The method of claim 1, wherein L is oxazolylene, pyrimidinylene or pyrazolylene.

* * * * *